(12) United States Patent
Van Remoortere et al.

(10) Patent No.: US 12,263,172 B2
(45) Date of Patent: Apr. 1, 2025

(54) TOLL-LIKE RECEPTOR AGONISTS FOR USE IN THE TREATMENT OF HEPATITIS B

(71) Applicant: CHIA TAI TIANQING PHARMACEUTICAL GROUP CO., LTD., Jiangsu (CN)

(72) Inventors: Peter Jozef M Van Remoortere, Raritan, NJ (US); Sean Mark Dalziel, Burlingame, CA (US); Ilham Smyej, Beerse (BE); Joris Jozef Vandenbossche, Beerse (BE); An Martine M De Creus, Beerse (BE); Mina Pastagia, South San Francisco, CA (US); Florence Marie Herschke, Beerse (BE)

(73) Assignee: CHIA TAI TIANQING PHARMECEUTICAL GROUP CO., LTD., Lianyungang (CN)

( * ) Notice: Subject to any disclaimer, the term of this patent is extended or adjusted under 35 U.S.C. 154(b) by 751 days.

(21) Appl. No.: 17/439,280

(22) PCT Filed: Mar. 13, 2020

(86) PCT No.: PCT/IB2020/052328
§ 371 (c)(1),
(2) Date: Sep. 14, 2021

(87) PCT Pub. No.: WO2020/188448
PCT Pub. Date: Sep. 24, 2020

(65) Prior Publication Data
US 2022/0249488 A1    Aug. 11, 2022

Related U.S. Application Data

(60) Provisional application No. 62/819,033, filed on Mar. 15, 2019.

(51) Int. Cl.
*A61K 31/519*    (2006.01)

(52) U.S. Cl.
CPC .................................. *A61K 31/519* (2013.01)

(58) Field of Classification Search
CPC ...................................................... A61K 31/519
See application file for complete search history.

(56) References Cited

U.S. PATENT DOCUMENTS

| | | | |
|---|---|---|---|
| 9,962,388 B2 * | 5/2018 | Ding | C07D 487/04 |
| 10,555,949 B2 * | 2/2020 | Ding | C07D 487/04 |

FOREIGN PATENT DOCUMENTS

| | | |
|---|---|---|
| EP | 3190113 A1 | 7/2017 |
| EP | 3381918 A1 | 10/2018 |
| EP | 3412672 A1 | 12/2018 |

* cited by examiner

*Primary Examiner* — Golam M Shameem
(74) *Attorney, Agent, or Firm* — Maschoff Brennan

(57) ABSTRACT

Provided herein are formulations and methods of using a TLR-7 agonist for the treatment of hepatitis B virus infection.

20 Claims, 9 Drawing Sheets

| Cohort 1 | 0.2 mg | 4-week follow-up |
| Cohort 2 | 0.6 mg | 4-week follow-up |
| Cohort 3 *Optional* | 1.8 mg | 4-week follow-up |
| Cohort 4 *Optional* | 1.25 mg | 4-week follow-up |
| Cohort 6 (Fed) | 1.25 mg | 4-week follow-up |

*Fig. 1*

TOLL-LIKE RECEPTOR AGONISTS FOR USE IN THE TREATMENT OF HEPATITIS B

RELATED APPLICATIONS

This application claims priority to U.S. Provisional Application No. 62/819,033, filed on Mar. 15, 2019, the contents of which is hereby incorporated by reference in its entirety.

BACKGROUND

Chronic hepatitis B virus (HBV) infection is a persistent, potentially progressive necroinflammatory liver disease associated with chronic HBV infection. Worldwide about 240-400 million persons are chronically infected with HBV, and chronic HBV infection is a major global cause of severe liver morbidity and liver-related mortality (Hepatitis B Factsheet, World Health Organization, 2013; Hoofnagle J H, et al., Management of Hepatitis B: Summary of a Clinical Research Workshop, Hepatology, 2007, 45(4):1056-1075; EASL Clinical Practice Guidelines: Management of chronic hepatitis B virus infection, J. Hepatology, 2012, 57:167-185 (EASL 2012); Lesmana L A, et al. Hepatitis B: overview of the burden of disease in the Asia-Pacific region, Liver International, 2006, 26:3-10; Lok A S F and McMahon B J, Chronic Hepatitis B: Update 2009, Hepatology, September 2009:1-36 (Lok 2009)).

With the continued worldwide prevalence of HBV-associated mortality and severe morbidity, there remains a need for improved HBV antiviral therapies that can achieve sustained viral response during and after treatment.

SUMMARY

Provided herein are formulations and methods of using a capsid assembly inhibitor for the treatment of hepatitis B virus infection. In an aspect, provided herein is a pharmaceutical composition for use in a method for the treatment of an HBV infection in a subject in need thereof, the composition comprising at least one TLR-7 agonist and at least one pharmaceutically acceptable excipient;

wherein the TLR-7 agonist is a compound of Formula I:

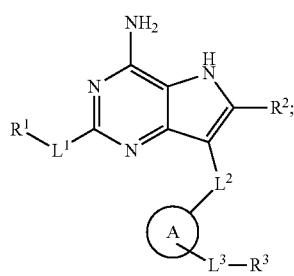

(I)

or a pharmaceutically acceptable salt thereof;
wherein:
$L^1$ is —O—;
$L^2$ is —CH$_2$—;
$R^1$ is selected from the group consisting of —H and —C$_1$-C$_{10}$ alkyl; wherein the alkyl is optionally substituted by one or more $R^4$ groups;
$R^2$ is selected from the group consisting of —H, —COOH, and —CONH$_2$;
ring A is selected from the group consisting of aryl and heteroaryl;
$L^3$ is selected from the group consisting of $C_0$-$C_6$ alkylene and imino; wherein alkylene and imino are optionally substituted by one or more $R^4$ groups;
$R^3$ is selected from the group consisting of —H, amino, $C_1$-$C_{10}$ alkyl, $C_3$-$C_{10}$ cycloalkyl, and 3-10 membered heterocycloalkyl; wherein amino, alkyl, cycloalkyl, and heterocycloalkyl are optionally substituted by one or more $R^4$ groups;
or wherein $R^3$ and $L^3$, together with the atom to which $L^3$ is attached and the adjacent atom in ring A, form a saturated or unsaturated 5-8 membered ring, which is optionally substituted by one or more $R^4$ groups;
$R^4$ is, independently at each occurrence, selected from the group consisting of —R, —OR, and =O; and
R is, independently at each occurrence, selected from the group consisting of H and $C_1$-$C_8$ alkyl;
wherein the method of treatment comprises administering, more particularly orally administering, the pharmaceutical composition to the human subject, and wherein the amount of the compound of Formula I in the composition is from 0.1 to 2.5 mg.

Provided herein are methods of treating an HBV infection in a subject in need thereof, comprising administering to the subject a therapeutically effective amount of the compositions described above.

In an aspect, provided herein are methods of reducing the viral load associated with an HBV infection in a subject in need thereof, comprising administering to the subject a therapeutically effective amount of the compositions described above.

Also provided herein are methods of reducing reoccurrence of an HBV infection in a subject in need thereof, comprising administering to the subject a therapeutically effective amount of the compositions described above.

In an aspect, provided herein are methods of reducing an adverse physiological impact of an HBV infection in a subject in need thereof, comprising administering to the subject a therapeutically effective amount of the compositions described above.

In an aspect, provided herein are methods of inducing remission of hepatic injury from an HBV infection in a subject in need thereof, comprising administering to the subject a therapeutically effective amount of the compositions described above.

Also provided herein are methods of prophylactically treating an HBV infection in a subject in need thereof, wherein the subject is afflicted with a latent HBV infection, comprising administering to the subject a therapeutically effective amount of the compositions described above.

In embodiments, the methods further comprise administering to the subject at least one additional therapeutic agent selected from the group consisting of a HBV polymerase inhibitor, interferon, viral entry inhibitor, viral maturation inhibitor, capsid assembly modulator, reverse transcriptase inhibitor, a TLR-agonist, and a combination thereof.

BRIEF DESCRIPTION OF THE DRAWINGS

FIG. 1 depicts the study design for a Phase 1, Double-Blind, Randomized, Placebo-Controlled, First-in-Human Study of the Safety, Tolerability, Pharmacokinetics and Pharmacodynamics of oral Compound 4, a Toll-like Receptor-7 Agonist, in Healthy Adults. Compound 4 (N=6 for the 0.2, 0.6, and 1.8 mg cohorts; N=8 for the 1.25 mg fasted cohort; N=7 for the 1.25 mg fed cohort) or placebo (N=2 per cohort) administered to healthy volunteers. After a washout period, Cohort 4 (1.25 mg Compound 4, fasted) received a second 1.25 mg dose under fed (standard meal) conditions in Cohort 6. SAD: single-ascending dose.

DETAILED DESCRIPTION

Figure 2:
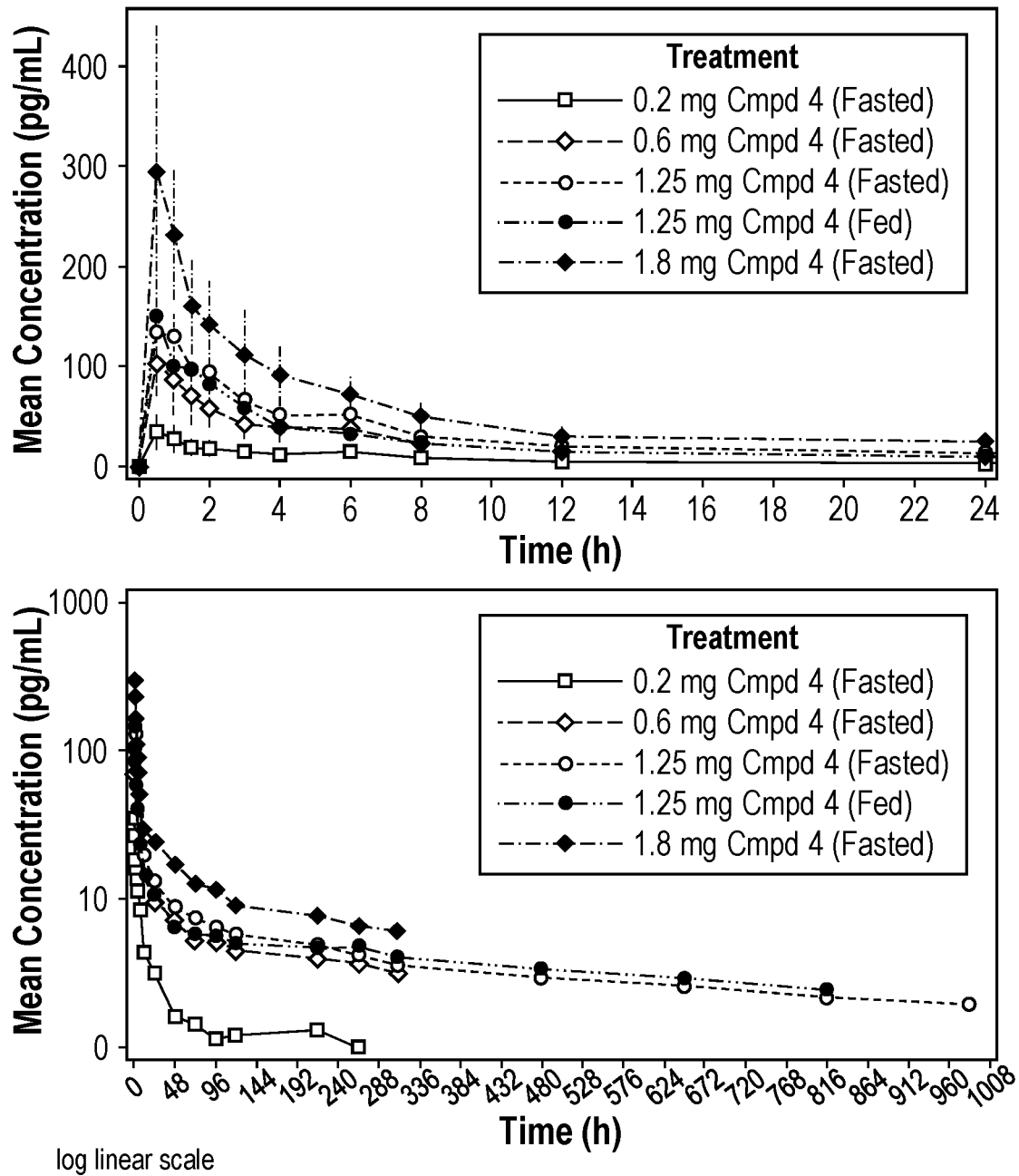
FIG. 2 depicts Compound 4 Plasma Concentrations (Mean±SD) Following Single Doses of Compound 4. N=6 per cohort; except for Compound 4 1.25 mg fasted (N=8) and 1.25 mg fed (N=7); Compound 4 was still detectable in the plasma 40 days after dosing with 1.25 mg (fasted), mean (SD) plasma concentration pre-dosing under fed conditions was 1.85 (0.597) pg/mL. SD: standard deviation.

Provided herein are methods of using a Toll-Like Receptor 7 (TLR-7) agonist for the treatment of hepatitis B virus infection. Provided herein are pharmaceutical compositions, which comprise at least one TLR-7 agonist and at least one pharmaceutically acceptable excipient;

wherein the TLR-7 agonist is a compound of Formula I:

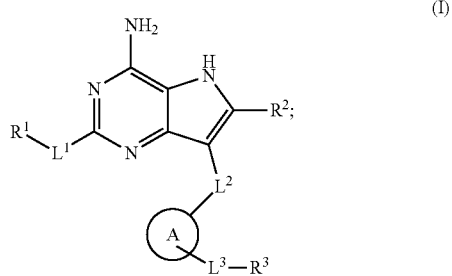

(I)

or a pharmaceutically acceptable salt thereof; wherein the amount of the at least one compound of Formula I in the composition is from 0.1 to 2.5 mg.

Definitions

Listed below are definitions of various terms used herein. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used in the specification and in the claims, the term "comprising" can include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated compounds, which allows the presence of only the named compounds, along with any pharmaceutically acceptable carriers, and excludes other compounds.

All ranges disclosed herein are inclusive of the recited endpoint and independently combinable (for example, the range of "from 0.1 mg to 2.5 mg" is inclusive of the endpoints, 0.1 mg and 2.5 mg, and all the intermediate values). The endpoints of the ranges and any values disclosed herein are not limited to the precise range or value; they are sufficiently imprecise to include values approximating these ranges and/or values.

As used herein, approximating language can be applied to modify any quantitative representation that can vary without resulting in a change in the basic function to which it is related. Accordingly, a value modified by a term or terms, such as "substantially," cannot be limited to the precise value specified, in some cases. In at least some instances, the approximating language can correspond to the precision of an instrument for measuring the value.

As used herein, the term "tablet" refers to a compressed or molded solid dosage form containing the active ingredients with suitable diluents. The tablet can be prepared by compression of mixtures or granulations obtained by wet granulation, dry granulation or by compaction.

The term "alkyl" refers to a straight- or branched-chain alkyl group having from 1 to 12 carbon atoms in the chain. Examples of alkyl groups include methyl (Me, which also may be structurally depicted by the symbol, "/"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. The term $C_{1-4}$alkyl as used here refers to a straight- or branched-chain alkyl group having from 1 to 4 carbon atoms in the chain. The term $C_{1-6}$alkyl as used here refers to a straight- or branched-chain alkyl group having from 1 to 6 carbon atoms in the chain.

The term "alkylene," employed alone or in combination with other terms, refers to a divalent alkyl linking group. An alkylene group formally corresponds to an alkane with two C H bond replaced by points of attachment of the alkylene group to the remainder of the compound. The term "Cn-m alkylene" refers to an alkylene group having n to m carbon atoms. Examples of alkylene groups include, but are not limited to, ethan-1,2-diyl, ethan-1,1-diyl, propan-1,3-diyl, propan-1,2-diyl, propan-1,1-diyl, butan-1,4-diyl, butan-1,3-diyl, butan-1,2-diyl, 2-methyl-propan-1,3-diyl and the like.

The term "aryl" refers to an unsaturated, aromatic monocyclic or bicyclic ring of 6 to 10 carbon members. Examples of aryl rings include phenyl and naphthalenyl.

The term "heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. Examples of heteroaryl groups include furyl, thienyl, pyrrolyl, oxazolyl, thiazolyl, imidazolyl, pyrazolyl, oxazolyl, thiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

The term "heterocycloalkyl," employed alone or in combination with other terms, refers to a non-aromatic ring or ring system, which may optionally contain one or more alkenylene groups as part of the ring structure, which has at least one heteroatom ring member independently selected from nitrogen, sulfur, oxygen and phosphorus, and which has 4-10 ring members, 4-7 ring members, or 4-6 ring members. Included within the term "heterocycloalkyl" are monocyclic 4-, 5-, 6- and 7-membered heterocycloalkyl groups. Heterocycloalkyl groups can include mono- or bicyclic (e.g., having two fused or bridged rings) or spirocyclic ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfido group or other oxidized linkage (e.g., C(O), S(O), C(S) or S(O)2, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring.

The terms "halo" or "halogen," used alone or in combination with other terms, refers to fluoro, chloro, bromo and iodo. In some embodiments, "halo" refers to a halogen atom selected from F, Cl, or Br. In some embodiments, halo groups are F. In some embodiments, halo groups are Cl.

As used herein, the term "treatment" or "treating," is defined as the application or administration of a therapeutic agent, i.e., a compound provided herein (alone or in combination with another pharmaceutical agent), to a patient, or application or administration of a therapeutic agent to an isolated tissue or cell line from a patient (e.g., for diagnosis or ex vivo applications), who has HBV infection, chronic HBV infection, a symptom of HBV infection or the potential to develop HBV infection, with the purpose to cure, heal, alleviate, relieve, alter, remedy, ameliorate, improve or affect HBV infection, the symptoms of HBV infection or the potential to develop HBV infection. Such treatments can be specifically tailored or modified, based on knowledge obtained from the field of pharmacogenomics.

The term "prevent," "preventing," or "prevention" as used herein comprises the prevention of at least one symptom associated with or caused by the state, disease or disorder being prevented.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject, or individual is human.

When used with respect to methods of treatment/prevention and the use of the compounds and pharmaceutical compositions thereof described herein, an individual "in need thereof" may be an individual who has been diagnosed with or previously treated for the condition to be treated. With respect to prevention, the individual in need thereof may also be an individual who is at risk for a condition (e.g., a family history of the condition, life-style factors indicative of risk for the condition, etc.). Typically, when a step of administering a compound provided herein, the method further contemplates a step of identifying an individual or subject in need of the particular treatment to be administered or having the particular condition to be treated.

As used herein, the term "pharmaceutically acceptable" refers to a material, such as a carrier or diluent, which does not abrogate the biological activity or properties of the compound, and is relatively non-toxic, i.e., the material can be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts provided herein include the conventional non-toxic salts of the parent compound formed, for example, from non-toxic inorganic or organic acids. The pharmaceutically acceptable salts provided herein can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound provided herein with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound provided herein within or to the patient such that it can perform its intended function. Typically, such constructs are carried or transported from one organ, or portion of the body, to another organ, or portion of the body. Each carrier must be "acceptable" in the sense of being compatible with the other ingredients of the formulation, including the compound provided herein, and not injurious to the patient. Some examples of materials that can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound provided herein, and are physiologically acceptable to the patient. Supplementary active compounds can also be incorporated into the compositions. The "pharmaceutically acceptable carrier" can further include a pharmaceutically acceptable salt of the compound provided herein. Other additional ingredients that can be included in the pharmaceutical compositions provided herein are known in the art and described, for example in Remington's Pharmaceutical Sciences (Genaro, Ed., Mack Publishing Co., 1985, Easton, PA), which is incorporated herein by reference.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "weight percent" is meant to refer to the quantity by weight of a compound and/or component in a composition as the quantity by weight of a constituent component of the composition as a percentage of the weight of the total composition. The weight percent can also be calculated by multiplying the mass fraction by 100. The "mass fraction" is the ratio of one substance of a mass $m_1$ to the mass of the total composition $m_T$ such that weight percent=$(m_1/m_T)*100$.

The term "combination," "therapeutic combination," "pharmaceutical combination," or "combination product" as used herein refer to a non-fixed combination or a kit of parts for the combined administration where two or more therapeutic agents can be administered independently, at the same time or separately within time intervals, especially where these time intervals allow that the combination partners show a cooperative, e.g., synergistic, effect.

As used herein, "treatment naïve" refers to a patient not having previously received treatment with a drug, investigational or approved, for HBV infection, in particular a nucleos(t)ide drug. "Treatment naïve" also refers to a patient not having been on treatment with HBV antiviral medicines within six months of entering a clinical study.

Alternatively, patients treated according to the methods of the disclosure can be "treatment experienced." As used herein, "treatment experienced" refers to a patient who has had at least one previous course of an HBV antiviral therapy, in particular a nucleos(t)ide. In some embodiments, the last dose in this previous course occurred at least three months prior to implementing a method according to the this disclosure.

HBV infections that may be treated according to the disclosed methods include HBV genotype A, B, C, and/or D infections. However, in embodiments, the methods disclosed may treat any HBV genotype ("pan-genotypic treatment"). HBV genotyping may be performed using methods known in the art, for example, INNO-LIPA® HBV Genotyping, Innogenetics N.V., Ghent, Belgium).

Pharmaceutical Compositions and Kits

The pharmaceutical compositions and dosage forms of this disclosure may be administered by any convenient route, for example, by infusion or bolus injection, by absorption through epithelial or mucocutaneous linings (e.g., oral mucosa, rectal and intestinal mucosa, etc.) and may be administered together with any other therapeutic agent. Administration can be systemic or local.

The therapeutic compositions provided herein will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semisolid gels, and semi-solid mixtures containing carbowax. See also Powell et al. "Compendium of excipients for parenteral formulations" PDA (1998) J Pharm Sci Technol 52:238-311.

The dose may vary depending upon the age and the weight of a subject to be administered, target disease, conditions, route of administration, and the like. Various delivery systems are known and can be used to administer the pharmaceutical composition provided herein, e.g., encapsulation in liposomes, microparticles, microcapsules, receptor mediated endocytosis (see, e.g., Wu et al. (1987) J. Biol. Chem. 262:4429-4432). Methods of introduction include, but are not limited to, intradermal, intramuscular, intraperitoneal, intravenous, transdermal, buccal, sublingual, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum, methyl cellulose, hydroxypropylmethyl-cellulose, sodium carboxymethylcellulose, and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

The injectable preparations may include dosage forms for intravenous, subcutaneous, intracutaneous and intramuscular injections, local injection, drip infusions, etc. These injectable preparations may be prepared by methods publicly known. For example, the injectable preparations may be prepared, e.g., by dissolving, suspending or emulsifying the pharmaceutical composition or dosage form in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared can be filled in an appropriate ampoule.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active components may be dissolved or suspended in suitable liquids, such as fatty oils, liquid paraffin, or liquid polyethylene glycols.

Alternatively, the composition may be in a powder form for constitution before use with a suitable vehicle, e.g., sterile, pyrogen-free water. The exact formulation, route of administration and dosage may be chosen by the physician familiar with the patient's condition. (See for example Fingl, et al., 1975, in "The Pharmacological Basis of Therapeutics", Chapter I, p. 1). Depending on the severity and responsiveness of the condition treated, dosing can also be a single administration of a slow release composition, with course of treatment lasting from several days to several weeks or until cure is effected or diminution of the disease state is achieved.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, chews, etc.

In accordance with the methods disclosed herein, pharmaceutical formulations can be administered to the patient using any acceptable device or mechanism. For example, the administration can be accomplished using a syringe and needle or with a reusable pen and/or autoinjector delivery device. The methods provided herein include the use of numerous reusable pen and/or autoinjector delivery devices to administer a pharmaceutical formulation.

In an aspect, provided herein is a pharmaceutical composition, which comprises at least one TLR-7 agonist and at least one pharmaceutically acceptable excipient; wherein the TLR-7 agonist is a compound of Formula I:

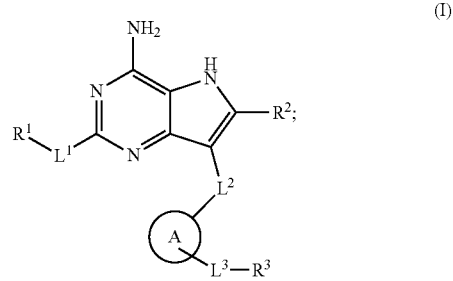

or a pharmaceutically acceptable salt thereof; wherein:
$L^1$ is —O—;
$L^2$ is —CH$_2$—;
$R^1$ is selected from the group consisting of —H and —C$_1$-C$_{10}$ alkyl; wherein the alkyl is optionally substituted by one or more $R^4$ groups;
$R^2$ is selected from the group consisting of —H, —CN, —COOH, and —CONH$_2$; ring A is selected from the group consisting of aryl and heteroaryl;
$L^3$ is selected from the group consisting of C$_0$-C$_6$ alkylene and imino; wherein alkylene and imino are optionally substituted by one or more $R^4$ groups;
$R^3$ is selected from the group consisting of —H, amino, C$_1$-C$_{10}$ alkyl, C$_3$-C$_{10}$ cycloalkyl, and 3-10 membered heterocycloalkyl; wherein amino, alkyl, cycloalkyl, and heterocycloalkyl are optionally substituted by one or more $R^4$ groups;
or wherein $R^3$ and $L^3$, together with the atom to which $L^3$ is attached and the adjacent atom in ring A, form a saturated or unsaturated 5-8 membered ring, which is optionally substituted by one or more $R^4$ groups;
$R^4$ is, independently at each occurrence, selected from the group consisting of —R, —OR, and =O; and
R is, independently at each occurrence, selected from the group consisting of H and C$_1$-C$_8$ alkyl;
wherein the amount of the compound of Formula I in the composition is from 0.1 to 2.5 mg.

In embodiments, $L^1$, $L^2$, $R^1$, $R^2$, and $L^3$ have the definitions provided above, and $R^3$ is selected from the group consisting of —H, amino, C$_1$-C$_{10}$ alkyl, C$_3$-C$_{10}$ cycloalkyl, and 3-10 membered heterocycloalkyl; wherein amino, alkyl, cycloalkyl, and heterocycloalkyl are optionally substituted by one or more $R^4$ groups;

$R^4$ is, independently at each occurrence, selected from the group consisting of —R, —OR, and =O; and R is, independently at each occurrence, selected from the group consisting of H, halo, and $C_1$-$C_8$ alkyl.

In embodiments, $R^3$ is 3-10 membered heterocycloalkyl substituted by halo.

In embodiments of Formula I,
$L^1$ is —O—;
$L^2$ is —$CH_2$—;
$R^1$ is selected from the group consisting of —H and —$C_1$-$C_{10}$ alkyl;
$R^2$ is selected from the group consisting of —H and —$CONH_2$;
ring A is selected from the group consisting of aryl and heteroaryl;
$L^3$ is $C_0$-$C_6$ alkylene; and
$R^3$ is 3-10 membered heterocycloalkyl.

In embodiments, the at least one compound of Formula I is selected from the group consisting of:

Compound 1

Compound 2

Compound 3

Compound 4

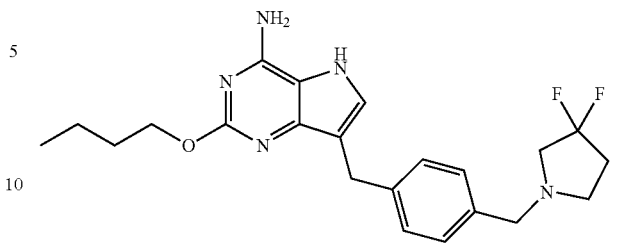

Compound 5

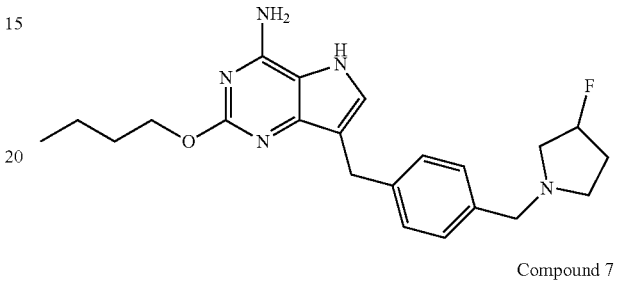

Compound 6

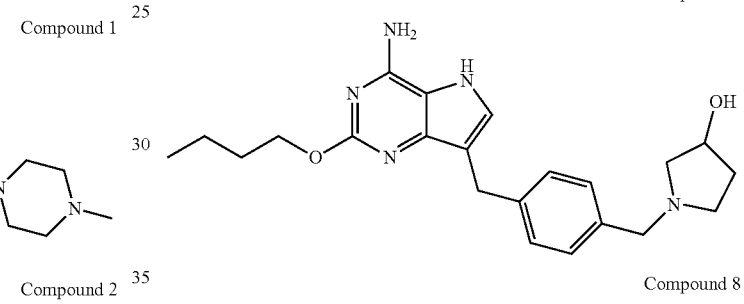

Compound 7

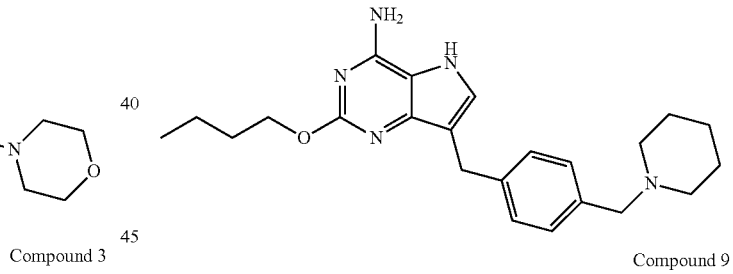

Compound 8

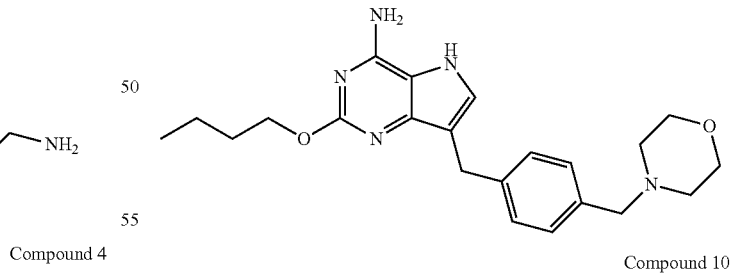

Compound 9

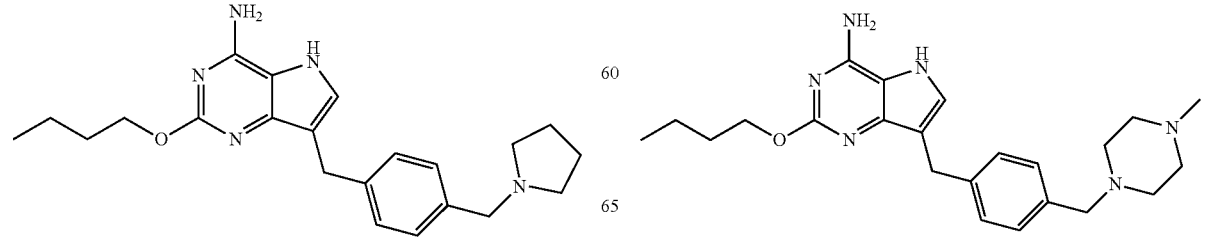

Compound 10

Compound 11
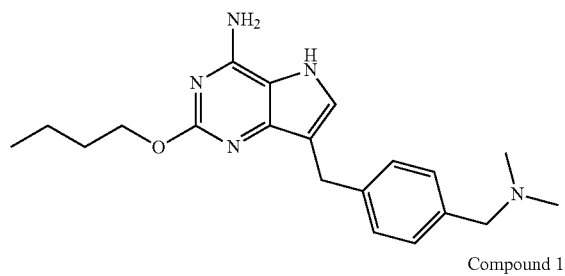
Compound 12
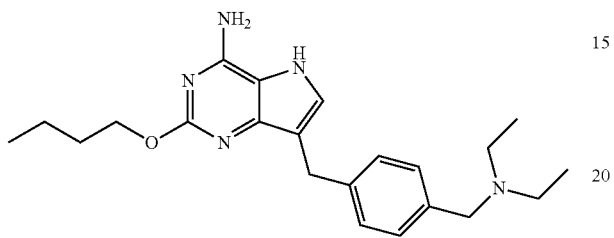
Compound 13
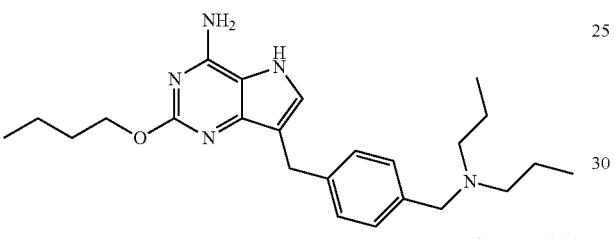
Compound 14
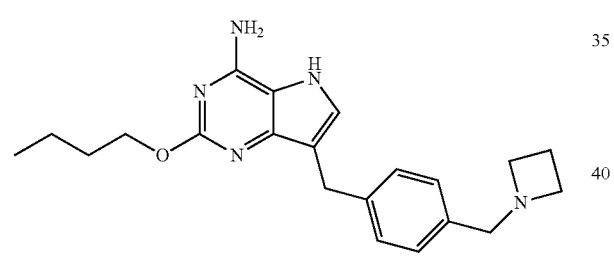
Compound 15
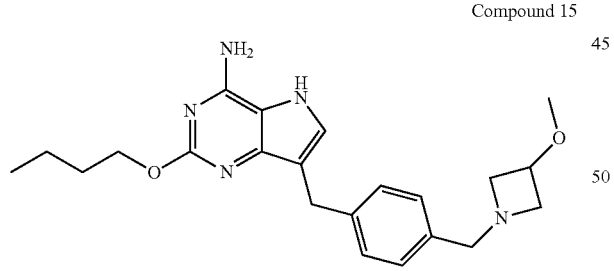
Compound 16
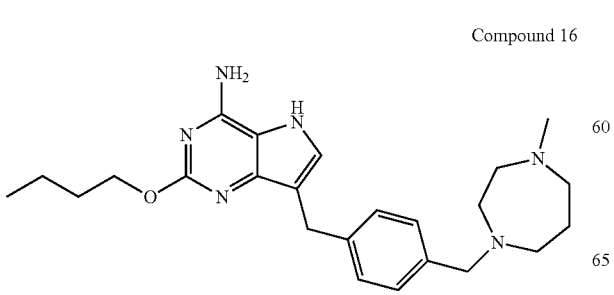
Compound 17
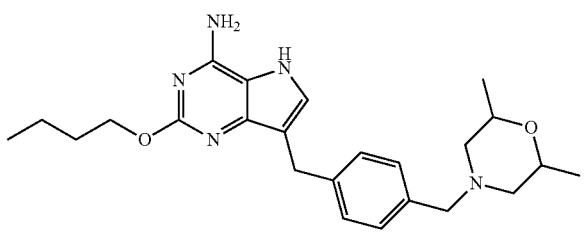
Compound 18
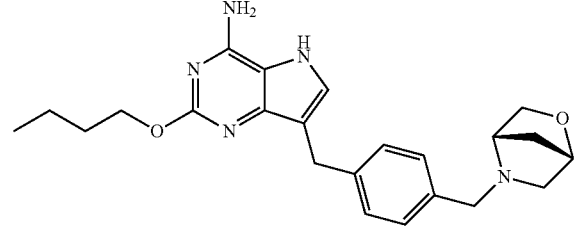
Compound 19
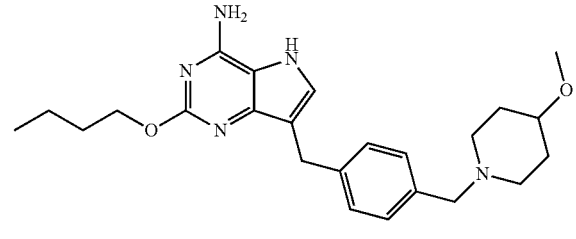
Compound 20
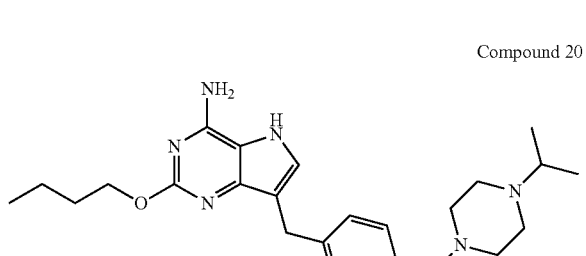
Compound 21
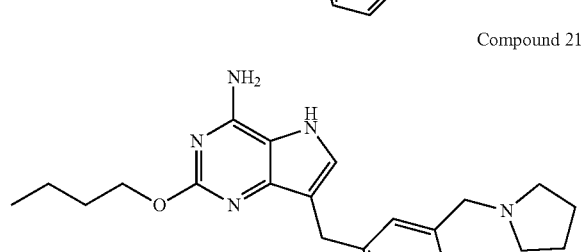
Compound 22
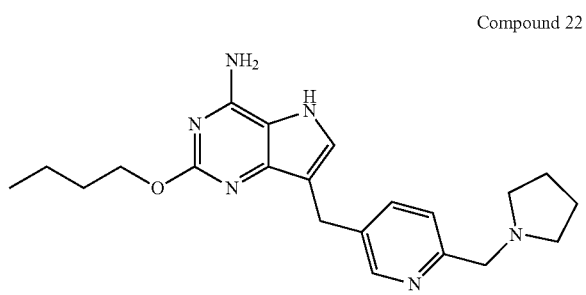

-continued
Compound 23
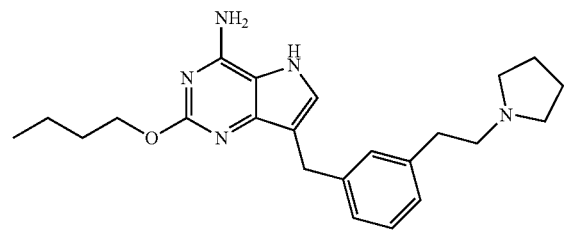
Compound 24
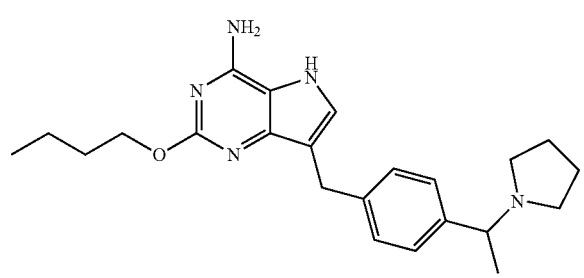
Compound 25
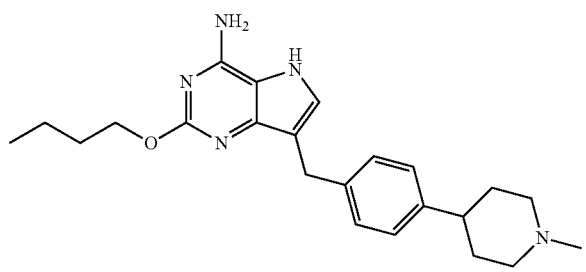
Compound 26
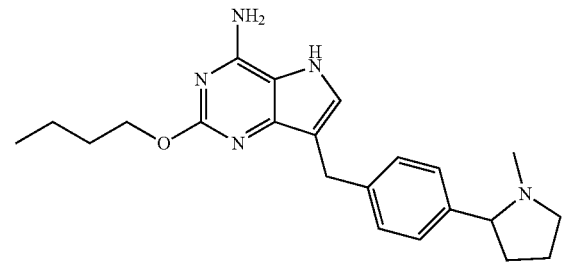
Compound 27
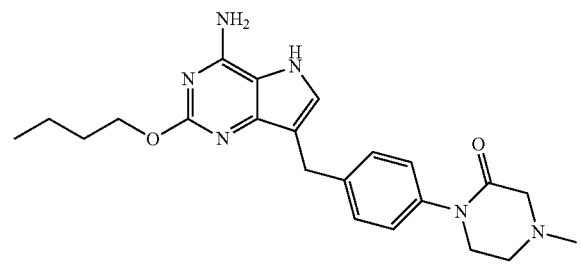
-continued
Compound 28
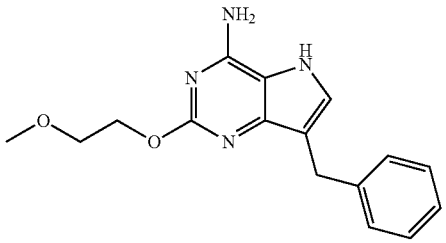
Compound 29
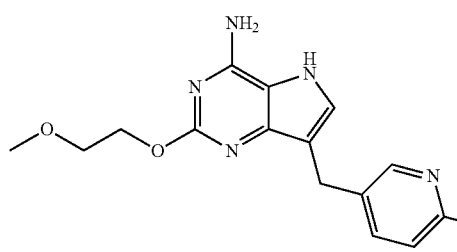
Compound 30
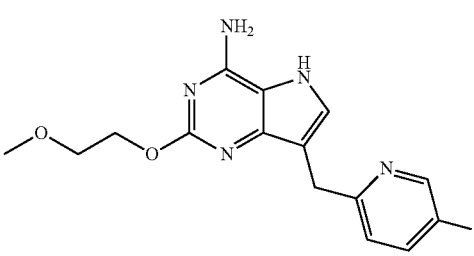
Compound 31
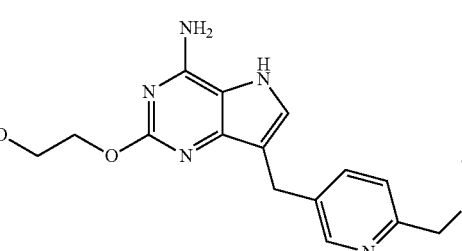
Compound 32
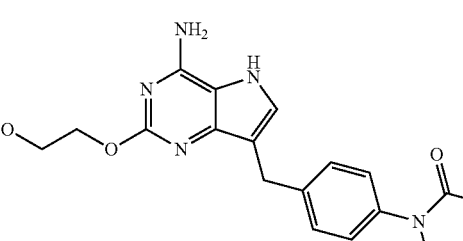
Compound 33
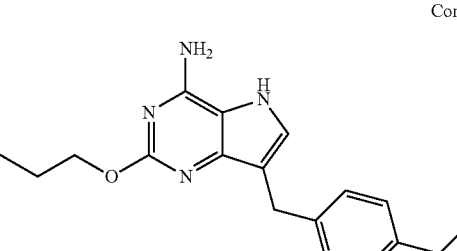

Compound 34
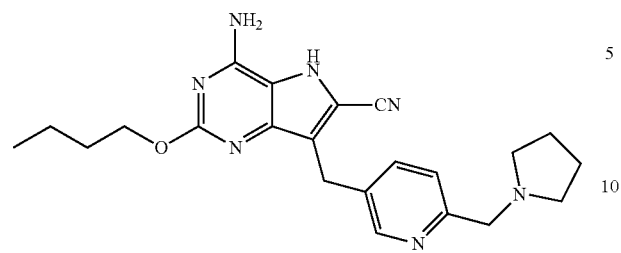
Compound 35
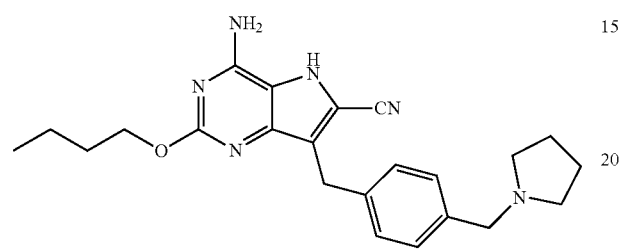
Compound 36
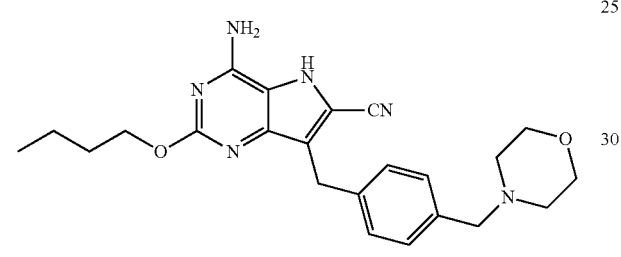
Compound 37
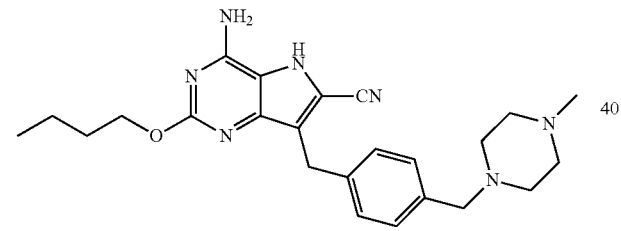
Compound 38
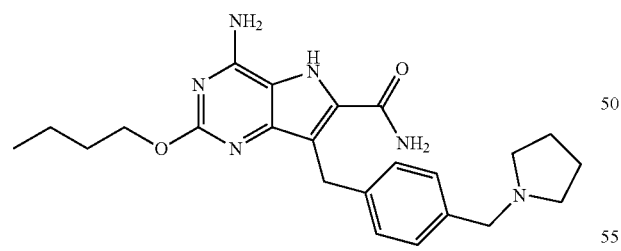
Compound 39
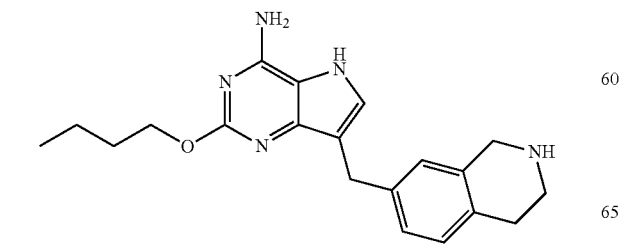
Compound 40
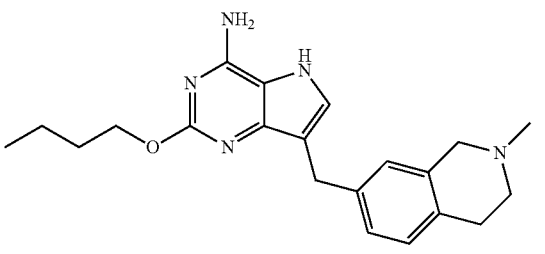
Compound 41
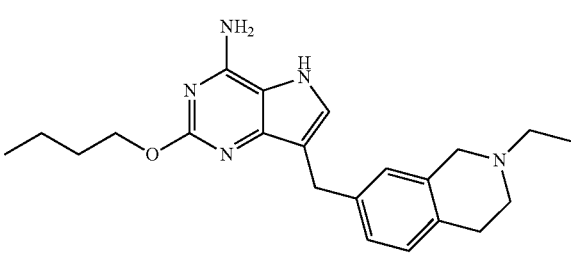
Compound 42
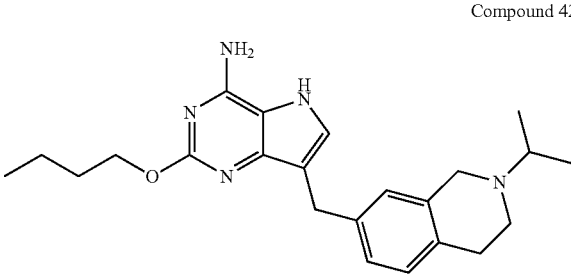
Compound 43
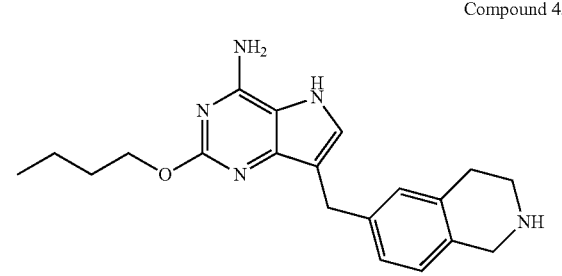
Compound 44
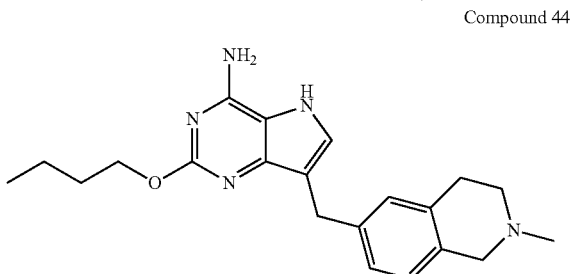
Compound 45
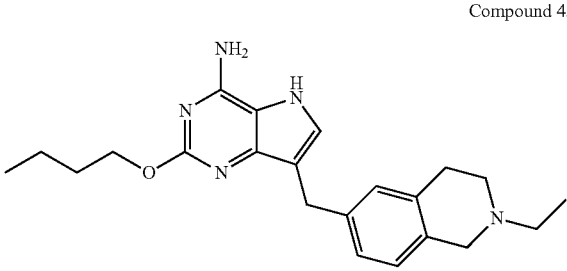
or a pharmaceutically acceptable salt thereof.

In embodiments, the at least one compound of Formula I is Compound 1, or a pharmaceutically acceptable salt thereof. In embodiments, the at least one compound of Formula I is Compound 2, or a pharmaceutically acceptable salt thereof. In other embodiments, the at least one compound of Formula I is Compound 3, or a pharmaceutically acceptable salt thereof. In embodiments, the at least one compound of Formula I is Compound 4, or a pharmaceutically acceptable salt thereof. In embodiments, the at least one compound of Formula I is Compound 5, or a pharmaceutically acceptable salt thereof. In embodiments, the at least one compound of Formula I is Compound 6, or a pharmaceutically acceptable salt thereof. In embodiments, the at least one compound of Formula I is Compound 7, or a pharmaceutically acceptable salt thereof. In embodiments, the at least one compound of Formula I is Compound 8, or a pharmaceutically acceptable salt thereof.

In embodiments of the pharmaceutical compositions and kits provided herein, the at least one compound of Formula I is Compound 9, or a pharmaceutically acceptable salt thereof. In embodiments, the at least one compound of Formula I is Compound 10, or a pharmaceutically acceptable salt thereof. In embodiments, the at least one compound of Formula I is Compound 11, or a pharmaceutically acceptable salt thereof. In embodiments, the at least one compound of Formula I is Compound 12, or a pharmaceutically acceptable salt thereof. In embodiments, the at least one compound of Formula I is Compound 13, or a pharmaceutically acceptable salt thereof. In embodiments, the at least one compound of Formula I is Compound 14, or a pharmaceutically acceptable salt thereof. In embodiments, the at least one compound of Formula I is Compound 15, or a pharmaceutically acceptable salt thereof. In embodiments, the at least one compound of Formula I is Compound 16, or a pharmaceutically acceptable salt thereof.

In embodiments of the pharmaceutical compositions and kits provided herein, the at least one compound of Formula I is Compound 17, or a pharmaceutically acceptable salt thereof. In embodiments, the at least one compound of Formula I is Compound 18, or a pharmaceutically acceptable salt thereof. In embodiments, the at least one compound of Formula I is Compound 19, or a pharmaceutically acceptable salt thereof. In embodiments, the at least one compound of Formula I is Compound 20, or a pharmaceutically acceptable salt thereof. In embodiments, the at least one compound of Formula I is Compound 21, or a pharmaceutically acceptable salt thereof. In embodiments, the at least one compound of Formula I is Compound 22, or a pharmaceutically acceptable salt thereof. In embodiments, the at least one compound of Formula I is Compound 23, or a pharmaceutically acceptable salt thereof. In embodiments, the at least one compound of Formula I is Compound 24, or a pharmaceutically acceptable salt thereof.

In embodiments of the pharmaceutical compositions and kits provided herein, the at least one compound of Formula I is Compound 25, or a pharmaceutically acceptable salt thereof. In embodiments, the at least one compound of Formula I is Compound 26, or a pharmaceutically acceptable salt thereof. In embodiments, the at least one compound of Formula I is Compound 27, or a pharmaceutically acceptable salt thereof. In embodiments, the at least one compound of Formula I is Compound 28, or a pharmaceutically acceptable salt thereof. In embodiments, the at least one compound of Formula I is Compound 29, or a pharmaceutically acceptable salt thereof. In embodiments, the at least one compound of Formula I is Compound 30, or a pharmaceutically acceptable salt thereof. In embodiments, the at least one compound of Formula I is Compound 31, or a pharmaceutically acceptable salt thereof. In embodiments, the at least one compound of Formula I is Compound 32, or a pharmaceutically acceptable salt thereof.

In embodiments of the pharmaceutical compositions and kits provided herein, the at least one compound of Formula I is Compound 33, or a pharmaceutically acceptable salt thereof. In embodiments, the at least one compound of Formula I is Compound 34, or a pharmaceutically acceptable salt thereof. In embodiments, the at least one compound of Formula I is Compound 35, or a pharmaceutically acceptable salt thereof. In embodiments, the at least one compound of Formula I is Compound 36, or a pharmaceutically acceptable salt thereof. In embodiments, the at least one compound of Formula I is Compound 37, or a pharmaceutically acceptable salt thereof. In embodiments, the at least one compound of Formula I is Compound 38, or a pharmaceutically acceptable salt thereof. In embodiments, the at least one compound of Formula I is Compound 39, or a pharmaceutically acceptable salt thereof. In embodiments, the at least one compound of Formula I is Compound 40, or a pharmaceutically acceptable salt thereof.

In embodiments of the pharmaceutical compositions and kits provided herein, the at least one compound of Formula I is Compound 41, or a pharmaceutically acceptable salt thereof. In embodiments, the at least one compound of Formula I is Compound 42, or a pharmaceutically acceptable salt thereof. In embodiments, the at least one compound of Formula I is Compound 43, or a pharmaceutically acceptable salt thereof. In embodiments, the at least one compound of Formula I is Compound 44, or a pharmaceutically acceptable salt thereof. In embodiments, the at least one compound of Formula I is Compound 45, or a pharmaceutically acceptable salt thereof.

In embodiments of the pharmaceutical compositions and kits provided herein, the amount of the at least one compound of Formula I in the composition is from 0.2 to 1.8 mg. In embodiments, the amount of the compound of Formula I in the composition is selected from the group consisting of 0.2 mg, 0.5 mg, 0.6 mg, 1.0 mg, 1.25 mg, and 1.8 mg. In embodiments, the amount of the compound of Formula I in the composition is selected from the group consisting of 0.2 mg, 0.6 mg, 1.25 mg, and 1.8 mg. In embodiments, the amount of the at least one compound of Formula I in the composition is 0.2 mg. In embodiments, the amount of the at least one compound of Formula I in the composition is 0.5 mg. In embodiments, the amount of the at least one compound of Formula I in the composition is 0.6 mg. In embodiments, the amount of the at least one compound of Formula I in the composition is 1.0 mg. In embodiments, the amount of the at least one compound of Formula I in the composition is 1.25 mg. In embodiments, the amount of the at least one compound of Formula I in the composition is 1.8 mg.

In embodiments of the pharmaceutical compositions and kits provided herein, the composition is formulated as an oral solution. In embodiments, the composition is formulated as an aqueous solution in citrate buffer. In embodiments, the concentration of the citrate buffer is 50 mM. In embodiments, the pH of the citrate buffer is 4-5. In embodiments, the pH of the citrate buffer is 4. In embodiments, the pH of the citrate buffer is 5.

In embodiments, the composition comprises:
a compound of Formula I;
citric acid monohydrate;
sodium hydroxide solution; and
water.

In embodiments, the composition comprises:
0.1 mg/mL of a compound of Formula I;
50 mM citric acid monohydrate;
sodium hydroxide solution; and
water.
In embodiments, the composition comprises:
1.0 mg/mL of a compound of Formula I;
50 mM citric acid monohydrate;
sodium hydroxide solution; and
water.
In embodiments, the composition comprises:
0.1-0.3 mg of a compound of Formula I;
50 mM citric acid monohydrate;
sodium hydroxide solution; and
water.
In embodiments, the composition comprises:
0.5-0.7 mg of a compound of Formula I;
50 mM citric acid monohydrate;
sodium hydroxide solution; and
water.
In embodiments, the composition comprises:
1.0-1.4 mg of a compound of Formula I;
50 mM citric acid monohydrate;
sodium hydroxide solution; and
water.
In embodiments, the composition comprises:
1.7-1.9 mg of a compound of Formula I;
50 mM citric acid monohydrate;
sodium hydroxide solution; and
water.
In embodiments, the composition comprises:
0.2 mg of a compound of Formula I;
50 mM citric acid monohydrate;
sodium hydroxide solution; and
water.
In embodiments, the composition comprises:
0.6 mg of a compound of Formula I;
50 mM citric acid monohydrate;
sodium hydroxide solution; and
water.
In embodiments, the composition comprises:
1.25 mg of a compound of Formula I;
50 mM citric acid monohydrate;
sodium hydroxide solution; and
water.
In embodiments, the composition comprises:
1.8 mg of a compound of Formula I;
50 mM citric acid monohydrate;
sodium hydroxide solution; and
water.
In embodiments, the composition comprises:
a compound of Formula I;
silicified microcrystalline cellulose;
croscarmellose sodium;
magnesium stearate;
polyvinyl alcohol;
polyethylene glycol;
titanium dioxide;
and talc.
In embodiments, the composition is a solid, oral tablet and comprises:
0.5 mg of a compound of Formula I;
silicified microcrystalline cellulose;
croscarmellose sodium;
magnesium stearate;
polyvinyl alcohol;
polyethylene glycol;
titanium dioxide;
and talc.
In embodiments, the composition is a solid, oral tablet and comprises:
1.0 mg of a compound of Formula I;
silicified microcrystalline cellulose;
croscarmellose sodium;
magnesium stearate;
polyvinyl alcohol;
polyethylene glycol;
titanium dioxide;
and talc.
In embodiments, the polyvinyl alcohol is USP/Ph.Eur polyvinyl alcohol.
In embodiments, the composition comprises:
Compound 1;
citric acid monohydrate;
sodium hydroxide solution; and
water.
In embodiments, the composition comprises:
0.1 mg/mL of Compound 1;
50 mM citric acid monohydrate;
sodium hydroxide solution; and
water.
In embodiments, the composition comprises:
1.0 mg/mL of Compound 1;
50 mM citric acid monohydrate;
sodium hydroxide solution; and
water.
In embodiments, the composition comprises:
Compound 2;
citric acid monohydrate;
sodium hydroxide solution; and
water.
In embodiments, the composition comprises:
0.1 mg/mL of Compound 2;
50 mM citric acid monohydrate;
sodium hydroxide solution; and
water.
In embodiments, the composition comprises:
1.0 mg/mL of Compound 2;
50 mM citric acid monohydrate;
sodium hydroxide solution; and
water.
In embodiments, the composition comprises:
Compound 3;
citric acid monohydrate;
sodium hydroxide solution; and
water.
In embodiments, the composition comprises:
0.1 mg/mL of Compound 3;
50 mM citric acid monohydrate;
sodium hydroxide solution; and
water.
In embodiments, the composition comprises:
1.0 mg/mL of Compound 3;
50 mM citric acid monohydrate;
sodium hydroxide solution; and
water.
In embodiments, the composition comprises:
Compound 4;
citric acid monohydrate;
sodium hydroxide solution; and
water.

In embodiments, the composition comprises:
0.1 mg/mL of Compound 4;
50 mM citric acid monohydrate;
sodium hydroxide solution; and
water.
In embodiments, the composition comprises:
1.0 mg/mL of Compound 4;
50 mM citric acid monohydrate;
sodium hydroxide solution; and
water.
In embodiments, the composition comprises:
0.1-0.3 mg of Compound 4;
50 mM citric acid monohydrate;
sodium hydroxide solution; and
water.
In embodiments, the composition comprises:
0.5-0.7 mg of Compound 4;
50 mM citric acid monohydrate;
sodium hydroxide solution; and
water.
In embodiments, the composition comprises:
1.0-1.4 mg of Compound 4;
50 mM citric acid monohydrate;
sodium hydroxide solution; and
water.
In embodiments, the composition comprises:
1.7-1.9 mg of Compound 4;
50 mM citric acid monohydrate;
sodium hydroxide solution; and
water.
In embodiments, the composition comprises:
0.2 mg of Compound 4;
50 mM citric acid monohydrate;
sodium hydroxide solution; and
water.
In embodiments, the composition comprises:
0.6 mg of Compound 4;
50 mM citric acid monohydrate;
sodium hydroxide solution; and
water.
In embodiments, the composition comprises:
1.25 mg of Compound 4;
50 mM citric acid monohydrate;
sodium hydroxide solution; and
water.
In embodiments, the composition comprises:
1.8 mg of Compound 4;
50 mM citric acid monohydrate;
sodium hydroxide solution; and
water.
In embodiments, the composition is a solid, oral tablet and comprises:
Compound 4;
silicified microcrystalline cellulose;
croscarmellose sodium;
magnesium stearate;
polyvinyl alcohol;
polyethylene glycol;
titanium dioxide;
and talc.
In embodiments, the composition is a solid, oral tablet and comprises:
0.1-0.3 mg Compound 4;
silicified microcrystalline cellulose;
croscarmellose sodium;
magnesium stearate;
polyvinyl alcohol;
polyethylene glycol;
titanium dioxide;
and talc.
In embodiments, the composition is a solid, oral tablet and comprises:
0.4-0.6 mg Compound 4;
silicified microcrystalline cellulose;
croscarmellose sodium;
magnesium stearate;
polyvinyl alcohol;
polyethylene glycol;
titanium dioxide;
and talc.
In embodiments, the composition is a solid, oral tablet and comprises:
0.9-1.1 mg Compound 4;
silicified microcrystalline cellulose;
croscarmellose sodium;
magnesium stearate;
polyvinyl alcohol;
polyethylene glycol;
titanium dioxide;
and talc.
In embodiments, the composition is a solid, oral tablet and comprises:
0.2 mg Compound 4;
silicified microcrystalline cellulose;
croscarmellose sodium;
magnesium stearate;
polyvinyl alcohol;
polyethylene glycol;
titanium dioxide;
and talc.
In embodiments, the composition is a solid, oral tablet and comprises:
0.5 mg Compound 4;
silicified microcrystalline cellulose;
croscarmellose sodium;
magnesium stearate;
polyvinyl alcohol;
polyethylene glycol;
titanium dioxide;
and talc.
In embodiments, the composition is a solid, oral tablet and comprises:
1.0 mg Compound 4;
silicified microcrystalline cellulose;
croscarmellose sodium;
magnesium stearate;
polyvinyl alcohol;
polyethylene glycol;
titanium dioxide;
and talc.
In embodiments, the polyvinyl alcohol is USP/Ph.Eur polyvinyl alcohol.
In embodiments, the composition comprises:
Compound 5;
citric acid monohydrate;
sodium hydroxide solution; and
water.
In embodiments, the composition comprises:
0.1 mg/mL of Compound 5;
50 mM citric acid monohydrate;
sodium hydroxide solution; and
water.

In embodiments, the composition comprises:
1.0 mg/mL of Compound 5;
50 mM citric acid monohydrate;
sodium hydroxide solution; and
water.
In embodiments, the composition comprises:
Compound 6;
citric acid monohydrate;
sodium hydroxide solution; and
water.
In embodiments, the composition comprises:
0.1 mg/mL of Compound 6;
50 mM citric acid monohydrate;
sodium hydroxide solution; and
water.
In embodiments, the composition comprises:
1.0 mg/mL of Compound 6;
50 mM citric acid monohydrate;
sodium hydroxide solution; and
water.
In embodiments, the composition comprises:
Compound 7;
citric acid monohydrate;
sodium hydroxide solution; and
water.
In embodiments, the composition comprises:
0.1 mg/mL of Compound 7;
50 mM citric acid monohydrate;
sodium hydroxide solution; and
water.
In embodiments, the composition comprises:
1.0 mg/mL of Compound 7;
50 mM citric acid monohydrate;
sodium hydroxide solution; and
water.
In embodiments, the composition comprises:
Compound 8;
citric acid monohydrate;
sodium hydroxide solution; and
water.
In embodiments, the composition comprises:
0.1 mg/mL of Compound 8;
50 mM citric acid monohydrate;
sodium hydroxide solution; and
water.
In embodiments, the composition comprises:
1.0 mg/mL of Compound 8;
50 mM citric acid monohydrate;
sodium hydroxide solution; and
water.
In embodiments, the composition comprises:
Compound 9;
citric acid monohydrate;
sodium hydroxide solution; and
water.
In embodiments, the composition comprises:
0.1 mg/mL of Compound 9;
50 mM citric acid monohydrate;
sodium hydroxide solution; and
water.
In embodiments, the composition comprises:
1.0 mg/mL of Compound 9;
50 mM citric acid monohydrate;
sodium hydroxide solution; and
water.
In embodiments, the composition comprises:
Compound 10;
citric acid monohydrate;
sodium hydroxide solution; and
water.
In embodiments, the composition comprises:
0.1 mg/mL of Compound 10;
50 mM citric acid monohydrate;
sodium hydroxide solution; and
water.
In embodiments, the composition comprises:
1.0 mg/mL of Compound 10;
50 mM citric acid monohydrate;
sodium hydroxide solution; and
water.
In embodiments, the composition comprises:
Compound 11;
citric acid monohydrate;
sodium hydroxide solution; and
water.
In embodiments, the composition comprises:
0.1 mg/mL of Compound 11;
50 mM citric acid monohydrate;
sodium hydroxide solution; and
water.
In embodiments, the composition comprises:
1.0 mg/mL of Compound 11;
50 mM citric acid monohydrate;
sodium hydroxide solution; and
water.
In embodiments, the composition comprises:
Compound 12;
citric acid monohydrate;
sodium hydroxide solution; and
water.
In embodiments, the composition comprises:
0.1 mg/mL of Compound 12;
50 mM citric acid monohydrate;
sodium hydroxide solution; and
water.
In embodiments, the composition comprises:
1.0 mg/mL of Compound 12;
50 mM citric acid monohydrate;
sodium hydroxide solution; and
water.
In embodiments, the composition comprises:
Compound 13;
citric acid monohydrate;
sodium hydroxide solution; and
water.
In embodiments, the composition comprises:
0.1 mg/mL of Compound 13;
50 mM citric acid monohydrate;
sodium hydroxide solution; and
water.
In embodiments, the composition comprises:
1.0 mg/mL of Compound 13;
50 mM citric acid monohydrate;
sodium hydroxide solution; and
water.
In embodiments, the composition comprises:
Compound 14;
citric acid monohydrate;
sodium hydroxide solution; and
water.

In embodiments, the composition comprises:
0.1 mg/mL of Compound 14;
50 mM citric acid monohydrate;
sodium hydroxide solution; and
water.
In embodiments, the composition comprises:
1.0 mg/mL of Compound 14;
50 mM citric acid monohydrate;
sodium hydroxide solution; and
water.
In embodiments, the composition comprises:
Compound 15;
citric acid monohydrate;
sodium hydroxide solution; and
water.
In embodiments, the composition comprises:
0.1 mg/mL of Compound 15;
50 mM citric acid monohydrate;
sodium hydroxide solution; and
water.
In embodiments, the composition comprises:
1.0 mg/mL of Compound 15;
50 mM citric acid monohydrate;
sodium hydroxide solution; and
water.
In embodiments, the composition comprises:
Compound 16;
citric acid monohydrate;
sodium hydroxide solution; and
water.
In embodiments, the composition comprises:
0.1 mg/mL of Compound 16;
50 mM citric acid monohydrate;
sodium hydroxide solution; and
water.
In embodiments, the composition comprises:
1.0 mg/mL of Compound 16;
50 mM citric acid monohydrate;
sodium hydroxide solution; and
water.
In embodiments, the composition comprises:
Compound 17;
citric acid monohydrate;
sodium hydroxide solution; and
water.
In embodiments, the composition comprises:
0.1 mg/mL of Compound 17;
50 mM citric acid monohydrate;
sodium hydroxide solution; and
water.
In embodiments, the composition comprises:
1.0 mg/mL of Compound 17;
50 mM citric acid monohydrate;
sodium hydroxide solution; and
water.
In embodiments, the composition comprises:
Compound 18;
citric acid monohydrate;
sodium hydroxide solution; and
water.
In embodiments, the composition comprises:
0.1 mg/mL of Compound 18;
50 mM citric acid monohydrate;
sodium hydroxide solution; and
water.
In embodiments, the composition comprises:
1.0 mg/mL of Compound 18;
50 mM citric acid monohydrate;
sodium hydroxide solution; and
water.
In embodiments, the composition comprises:
Compound 19;
citric acid monohydrate;
sodium hydroxide solution; and
water.
In embodiments, the composition comprises:
0.1 mg/mL of Compound 19;
50 mM citric acid monohydrate;
sodium hydroxide solution; and
water.
In embodiments, the composition comprises:
1.0 mg/mL of Compound 19;
50 mM citric acid monohydrate;
sodium hydroxide solution; and
water.
In embodiments, the composition comprises:
Compound 20;
citric acid monohydrate;
sodium hydroxide solution; and
water.
In embodiments, the composition comprises:
0.1 mg/mL of Compound 20;
50 mM citric acid monohydrate;
sodium hydroxide solution; and
water.
In embodiments, the composition comprises:
1.0 mg/mL of Compound 20;
50 mM citric acid monohydrate;
sodium hydroxide solution; and
water.
In embodiments, the composition comprises:
Compound 21;
citric acid monohydrate;
sodium hydroxide solution; and
water.
In embodiments, the composition comprises:
0.1 mg/mL of Compound 21;
50 mM citric acid monohydrate;
sodium hydroxide solution; and
water.
In embodiments, the composition comprises:
1.0 mg/mL of Compound 21;
50 mM citric acid monohydrate;
sodium hydroxide solution; and
water.
In embodiments, the composition comprises:
Compound 22;
citric acid monohydrate;
sodium hydroxide solution; and
water.
In embodiments, the composition comprises:
0.1 mg/mL of Compound 22;
50 mM citric acid monohydrate;
sodium hydroxide solution; and
water.
In embodiments, the composition comprises:
1.0 mg/mL of Compound 22;
50 mM citric acid monohydrate;
sodium hydroxide solution; and
water.

In embodiments, the composition comprises:
Compound 23;
citric acid monohydrate;
sodium hydroxide solution; and
water.
In embodiments, the composition comprises:
0.1 mg/mL of Compound 23;
50 mM citric acid monohydrate;
sodium hydroxide solution; and
water.
In embodiments, the composition comprises:
1.0 mg/mL of Compound 23;
50 mM citric acid monohydrate;
sodium hydroxide solution; and
water.
In embodiments, the composition comprises:
Compound 24;
citric acid monohydrate;
sodium hydroxide solution; and
water.
In embodiments, the composition comprises:
0.1 mg/mL of Compound 24;
50 mM citric acid monohydrate;
sodium hydroxide solution; and
water.
In embodiments, the composition comprises:
1.0 mg/mL of Compound 24;
50 mM citric acid monohydrate;
sodium hydroxide solution; and
water.
In embodiments, the composition comprises:
Compound 25;
citric acid monohydrate;
sodium hydroxide solution; and
water.
In embodiments, the composition comprises:
0.1 mg/mL of Compound 25;
50 mM citric acid monohydrate;
sodium hydroxide solution; and
water.
In embodiments, the composition comprises:
1.0 mg/mL of Compound 25;
50 mM citric acid monohydrate;
sodium hydroxide solution; and
water.
In embodiments, the composition comprises:
Compound 26;
citric acid monohydrate;
sodium hydroxide solution; and
water.
In embodiments, the composition comprises:
0.1 mg/mL of Compound 26;
50 mM citric acid monohydrate;
sodium hydroxide solution; and
water.
In embodiments, the composition comprises:
1.0 mg/mL of Compound 26;
50 mM citric acid monohydrate;
sodium hydroxide solution; and
water.
In embodiments, the composition comprises:
Compound 27;
citric acid monohydrate;
sodium hydroxide solution; and
water.
In embodiments, the composition comprises:
0.1 mg/mL of Compound 27;
50 mM citric acid monohydrate;
sodium hydroxide solution; and
water.
In embodiments, the composition comprises:
1.0 mg/mL of Compound 27;
50 mM citric acid monohydrate;
sodium hydroxide solution; and
water.
In embodiments, the composition comprises:
Compound 28;
citric acid monohydrate;
sodium hydroxide solution; and
water.
In embodiments, the composition comprises:
0.1 mg/mL of Compound 28;
50 mM citric acid monohydrate;
sodium hydroxide solution; and
water.
In embodiments, the composition comprises:
1.0 mg/mL of Compound 28;
50 mM citric acid monohydrate;
sodium hydroxide solution; and
water.
In embodiments, the composition comprises:
Compound 29;
citric acid monohydrate;
sodium hydroxide solution; and
water.
In embodiments, the composition comprises:
0.1 mg/mL of Compound 29;
50 mM citric acid monohydrate;
sodium hydroxide solution; and
water.
In embodiments, the composition comprises:
1.0 mg/mL of Compound 29;
50 mM citric acid monohydrate;
sodium hydroxide solution; and
water.
In embodiments, the composition comprises:
Compound 30;
citric acid monohydrate;
sodium hydroxide solution; and
water.
In embodiments, the composition comprises:
0.1 mg/mL of Compound 30;
50 mM citric acid monohydrate;
sodium hydroxide solution; and
water.
In embodiments, the composition comprises:
1.0 mg/mL of Compound 30;
50 mM citric acid monohydrate;
sodium hydroxide solution; and
water.
In embodiments, the composition comprises:
Compound 31;
citric acid monohydrate;
sodium hydroxide solution; and
water.
In embodiments, the composition comprises:
0.1 mg/mL of Compound 31;
50 mM citric acid monohydrate;
sodium hydroxide solution; and
water.

In embodiments, the composition comprises:
1.0 mg/mL of Compound 31;
50 mM citric acid monohydrate;
sodium hydroxide solution; and
water.
In embodiments, the composition comprises:
Compound 32;
citric acid monohydrate;
sodium hydroxide solution; and
water.
In embodiments, the composition comprises:
0.1 mg/mL of Compound 32;
50 mM citric acid monohydrate;
sodium hydroxide solution; and
water.
In embodiments, the composition comprises:
1.0 mg/mL of Compound 32;
50 mM citric acid monohydrate;
sodium hydroxide solution; and
water.
In embodiments, the composition comprises:
Compound 33;
citric acid monohydrate;
sodium hydroxide solution; and
water.
In embodiments, the composition comprises:
0.1 mg/mL of Compound 33;
50 mM citric acid monohydrate;
sodium hydroxide solution; and
water.
In embodiments, the composition comprises:
1.0 mg/mL of Compound 33;
50 mM citric acid monohydrate;
sodium hydroxide solution; and
water.
In embodiments, the composition comprises:
Compound 34;
citric acid monohydrate;
sodium hydroxide solution; and
water.
In embodiments, the composition comprises:
0.1 mg/mL of Compound 34;
50 mM citric acid monohydrate;
sodium hydroxide solution; and
water.
In embodiments, the composition comprises:
1.0 mg/mL of Compound 34;
50 mM citric acid monohydrate;
sodium hydroxide solution; and
water.
In embodiments, the composition comprises:
Compound 35;
citric acid monohydrate;
sodium hydroxide solution; and
water.
In embodiments, the composition comprises:
0.1 mg/mL of Compound 35;
50 mM citric acid monohydrate;
sodium hydroxide solution; and
water.
In embodiments, the composition comprises:
1.0 mg/mL of Compound 35;
50 mM citric acid monohydrate;
sodium hydroxide solution; and
water.
In embodiments, the composition comprises:
Compound 36;
citric acid monohydrate;
sodium hydroxide solution; and
water.
In embodiments, the composition comprises:
0.1 mg/mL of Compound 36;
50 mM citric acid monohydrate;
sodium hydroxide solution; and
water.
In embodiments, the composition comprises:
1.0 mg/mL of Compound 36;
50 mM citric acid monohydrate;
sodium hydroxide solution; and
water.
In embodiments, the composition comprises:
Compound 37;
citric acid monohydrate;
sodium hydroxide solution; and
water.
In embodiments, the composition comprises:
0.1 mg/mL of Compound 37;
50 mM citric acid monohydrate;
sodium hydroxide solution; and
water.
In embodiments, the composition comprises:
1.0 mg/mL of Compound 37;
50 mM citric acid monohydrate;
sodium hydroxide solution; and
water.
In embodiments, the composition comprises:
Compound 38;
citric acid monohydrate;
sodium hydroxide solution; and
water.
In embodiments, the composition comprises:
0.1 mg/mL of Compound 38;
50 mM citric acid monohydrate;
sodium hydroxide solution; and
water.
In embodiments, the composition comprises:
1.0 mg/mL of Compound 38;
50 mM citric acid monohydrate;
sodium hydroxide solution; and
water.
In embodiments, the composition comprises:
Compound 39;
citric acid monohydrate;
sodium hydroxide solution; and
water.
In embodiments, the composition comprises:
0.1 mg/mL of Compound 39;
50 mM citric acid monohydrate;
sodium hydroxide solution; and
water.
In embodiments, the composition comprises:
1.0 mg/mL of Compound 39;
50 mM citric acid monohydrate;
sodium hydroxide solution; and
water.
In embodiments, the composition comprises:
Compound 40;
citric acid monohydrate;
sodium hydroxide solution; and
water.

In embodiments, the composition comprises:
0.1 mg/mL of Compound 40;
50 mM citric acid monohydrate;
sodium hydroxide solution; and
water.
In embodiments, the composition comprises:
1.0 mg/mL of Compound 40;
50 mM citric acid monohydrate;
sodium hydroxide solution; and
water.
In embodiments, the composition comprises:
Compound 41;
citric acid monohydrate;
sodium hydroxide solution; and
water.
In embodiments, the composition comprises:
0.1 mg/mL of Compound 41;
50 mM citric acid monohydrate;
sodium hydroxide solution; and
water.
In embodiments, the composition comprises:
1.0 mg/mL of Compound 41;
50 mM citric acid monohydrate;
sodium hydroxide solution; and
water.
In embodiments, the composition comprises:
Compound 42;
citric acid monohydrate;
sodium hydroxide solution; and
water.
In embodiments, the composition comprises:
0.1 mg/mL of Compound 42;
50 mM citric acid monohydrate;
sodium hydroxide solution; and
water.
In embodiments, the composition comprises:
1.0 mg/mL of Compound 42;
50 mM citric acid monohydrate;
sodium hydroxide solution; and
water.
In embodiments, the composition comprises:
Compound 43;
citric acid monohydrate;
sodium hydroxide solution; and
water.
In embodiments, the composition comprises:
0.1 mg/mL of Compound 43;
50 mM citric acid monohydrate;
sodium hydroxide solution; and
water.
In embodiments, the composition comprises:
1.0 mg/mL of Compound 43;
50 mM citric acid monohydrate;
sodium hydroxide solution; and
water.
In embodiments, the composition comprises:
Compound 44;
citric acid monohydrate;
sodium hydroxide solution; and
water.
In embodiments, the composition comprises:
0.1 mg/mL of Compound 44;
50 mM citric acid monohydrate;
sodium hydroxide solution; and
water.
In embodiments, the composition comprises:
1.0 mg/mL of Compound 44;
50 mM citric acid monohydrate;
sodium hydroxide solution; and
water.
In embodiments, the composition comprises:
Compound 45;
citric acid monohydrate;
sodium hydroxide solution; and
water.
In embodiments, the composition comprises:
0.1 mg/mL of Compound 45;
50 mM citric acid monohydrate;
sodium hydroxide solution; and
water.
In embodiments, the composition comprises:
1.0 mg/mL of Compound 45;
50 mM citric acid monohydrate;
sodium hydroxide solution; and
water.

In additional embodiments, pharmaceutical kits are provided. The kit includes a sealed container approved for the storage of pharmaceutical compositions, the container containing one of the above-described pharmaceutical compositions. In some embodiments, the sealed container minimizes the contact of air with the ingredients, e.g. an airless bottle. In other embodiments, the sealed container is a sealed tube. An instruction for the use of the composition and the information about the composition are to be included in the kit.

Dosing/Administration

In one aspect, provided herein are methods of treating HBV infection in a subject in need thereof, comprising administering to the subject a pharmaceutical composition at least one TLR-7 agonist and at least one pharmaceutically acceptable excipient;

wherein the TLR-7 agonist is a compound of Formula I:

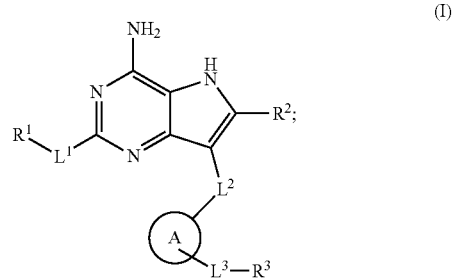

or a pharmaceutically acceptable salt thereof;
wherein:
$L^1$ is —O—;
$L^2$ is —CH$_2$—;
$R^1$ is selected from the group consisting of —H and —C$_1$-C$_{10}$ alkyl; wherein the alkyl is optionally substituted by one or more $R^4$ groups;
$R^2$ is selected from the group consisting of —H, —CN, —COOH, and —CONH$_2$; ring A is selected from the group consisting of aryl and heteroaryl;
$L^3$ is selected from the group consisting of C$_0$-C$_6$ alkylene and imino; wherein alkylene and imino are optionally substituted by one or more $R^4$ groups;
$R^3$ is selected from the group consisting of —H, amino, C$_1$-C$_{10}$ alkyl, C$_3$-C$_{10}$ cycloalkyl, and 3-10 membered heterocycloalkyl; wherein amino, alkyl, cycloalkyl, and heterocycloalkyl are optionally substituted by one or more $R^4$ groups;

or wherein $R^3$ and $L^3$, together with the atom to which $L^3$ is attached and the adjacent atom in ring A, form a saturated or unsaturated 5-8 membered ring, which is optionally substituted by one or more $R^4$ groups;

$R^4$ is, independently at each occurrence, selected from the group consisting of —R, —OR, and =O; and R is, independently at each occurrence, selected from the group consisting of H and $C_1$-$C_8$ alkyl.

In embodiments, $L^1$, $L^2$, $R^1$, $R^2$, and $L^3$ have the definitions provided above, and $R^3$ is selected from the group consisting of —H, amino, $C_1$-$C_{10}$ alkyl, $C_3$-$C_{10}$ cycloalkyl, and 3-10 membered heterocycloalkyl; wherein amino, alkyl, cycloalkyl, and heterocycloalkyl are optionally substituted by one or more $R^4$ groups;

$R^4$ is, independently at each occurrence, selected from the group consisting of —R, —OR, and =O; and R is, independently at each occurrence, selected from the group consisting of H, halo, and $C_1$-$C_8$ alkyl.

In embodiments, $R^3$ is 3-10 membered heterocycloalkyl substituted by halo.

In some embodiments, the amount of the at least one compound of Formula I in the composition is from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of the at least one compound of Formula I in the composition is from 0.2 to 1.8 mg. In embodiments, the amount of the compound of Formula I in the composition is selected from the group consisting of 0.2 mg, 0.6 mg, 1.25 mg, and 1.8 mg. In embodiments, the amount of the compound of Formula I in the composition is selected from the group consisting of 0.2 mg, 0.5 mg, 0.6 mg, 1.0 mg, 1.25 mg, and 1.8 mg. In embodiments, the amount of the at least one compound of Formula I in the composition is 0.2 mg. In embodiments, the amount of the at least one compound of Formula I in the composition is 0.5 mg. In embodiments, the amount of the at least one compound of Formula I in the composition is 0.6 mg. In embodiments, the amount of the at least one compound of Formula I in the composition is 1.0 mg. In embodiments, the amount of the at least one compound of Formula I in the composition is 1.25 mg. In embodiments, the amount of the at least one compound of Formula I in the composition is 1.8 mg.

In embodiments of the methods, the compound of Formula I is administered at a dose of 0.1 to 2.5 mg. In embodiments of the methods, the compound of Formula I is administered at a single dose of 0.1 to 2.5 mg. In embodiments of the methods, the compound of Formula I is administered at multiple doses, wherein each individual dose of said multiple doses is of 0.1 to 2.5 mg. In embodiments, the compound of Formula I is administered once daily (qd), once weekly (qw), or once every two weeks (q2w). In embodiments, the compound of Formula I is administered once daily (qd). In embodiments, the compound of Formula I is administered once weekly (qw). In embodiments, the compound of Formula I is administered once every two weeks (q2w). In embodiments, the compound of Formula I is administered once daily (qd), once weekly (qw), or once every two weeks (q2w) for at least four weeks. In embodiments, the compound of Formula I is administered once daily (qd) for at least four weeks. In embodiments, the compound of Formula I is administered once weekly (qw) for at least four weeks. In embodiments, the compound of Formula I is administered once every two weeks (q2w) for at least four weeks. In embodiments, the compound of Formula I is administered once daily (qd) in an amount selected from the group consisting of 0.2 mg, 0.5 mg, 0.6 mg, 1.0 mg, 1.25 mg, and 1.8 mg. In embodiments, the compound of Formula I is administered once weekly (qw) in an amount selected from the group consisting of 0.2 mg, 0.5 mg, 0.6 mg, 1.0 mg, 1.25 mg, and 1.8 mg. In embodiments, the compound of Formula I is administered once every two weeks (q2w) in an amount selected from the group consisting of 0.2 mg, 0.5 mg, 0.6 mg, 1.0 mg, 1.25 mg, and 1.8 mg.

In embodiments, the compound of Formula I is administered as an oral solution. In embodiments, the compound of Formula I is administered as a solid, oral tablet.

In embodiments of the methods of treating HBV infection in a patient in need thereof provided herein, the compound of Formula I is Compound 1, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 1 in the composition is from 0.2 to 1.8 mg. In embodiments, the amount of Compound 1 in the composition is selected from the group consisting of 0.2 mg, 0.6 mg, 1.25 mg, and 1.8 mg. In embodiments, the amount of Compound 1 in the composition is 0.2 mg. In embodiments, the amount of Compound 1 in the composition is 0.6 mg. In embodiments, the amount of Compound 1 in the composition is 1.25 mg. In embodiments, the amount of Compound 1 in the composition is 1.8 mg.

In embodiments of the methods of treating HBV infection in a patient in need thereof provided herein, the compound of Formula I is Compound 2, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 2 in the composition is from 0.2 to 1.8 mg. In embodiments, the amount of Compound 2 in the composition is selected from the group consisting of 0.2 mg, 0.6 mg, 1.25 mg, and 1.8 mg. In embodiments, the amount of Compound 2 in the composition is 0.2 mg. In embodiments, the amount of Compound 2 in the composition is 0.6 mg. In embodiments, the amount of Compound 2 in the composition is 1.25 mg. In embodiments, the amount of Compound 2 in the composition is 1.8 mg.

In embodiments of the methods of treating HBV infection in a patient in need thereof provided herein, the compound of Formula I is Compound 3, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 3 in the composition is from 0.2 to 1.8 mg. In embodiments, the amount of Compound 3 in the composition is selected from the group consisting of 0.2 mg, 0.6 mg, 1.25 mg, and 1.8 mg. In embodiments, the amount of Compound 3 in the composition is 0.2 mg. In embodiments, the amount of Compound 3 in the composition is 0.6 mg. In embodiments, the amount of Compound 3 in the composition is 1.25 mg. In embodiments, the amount of Compound 3 in the composition is 1.8 mg.

In embodiments of the methods of treating HBV infection in a patient in need thereof provided herein, the compound of Formula I is Compound 4, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 4 in the composition is from 0.2 to 1.8 mg. In embodiments, the amount of Compound 4 in the composition is selected from the group consisting of 0.2 mg, 0.6 mg, 1.25 mg, and 1.8 mg. In embodiments, the amount of Compound 4 in the composition is selected from the group consisting of 0.2 mg, 0.5 mg, 0.6 mg, 1.0 mg, 1.25 mg, and 1.8 mg. In embodiments, the amount of Compound 4 in the composition is 0.2 mg. In embodiments, the amount of Compound 4 in the composition is 0.5 mg. In embodiments, the amount of Compound 4 in the composition is 0.6 mg. In embodiments, the amount of Compound 4 in the composition is 1.0 mg. In embodiments, the amount of Compound 4 in the composition is 1.25 mg. In embodiments, the amount of Compound 4 in the composition is 1.8 mg. In embodiments, Compound 4 is administered once daily (qd), once weekly (qw), or once every two weeks (q2w). In embodiments, Compound 4 is administered once daily (qd). In embodiments, Compound 4 is administered once weekly (qw). In embodiments, Compound 4 is administered once every two weeks (q2w). In embodiments, Compound 4 is administered once daily (qd), once weekly (qw), or once every two weeks (q2w) for at least four weeks. In embodiments, Compound 4 is administered once daily (qd) for at least four weeks. In embodiments, Compound 4 is administered once weekly (qw) for at least four weeks. In embodiments, Compound 4 is administered once every two weeks (q2w) for at least four weeks. In embodiments, Compound 4 is administered once daily (qd) in an amount selected from the group consisting of 0.2 mg, 0.5 mg, 0.6 mg, 1.0 mg, 1.25 mg, and 1.8 mg. In embodiments, Compound 4 is administered once weekly (qw) in an amount selected from the group consisting of 0.2 mg, 0.5 mg, 0.6 mg, 1.0 mg, 1.25 mg, and 1.8 mg. In embodiments, Compound 4 is administered once every two weeks (q2w) in an amount selected from the group consisting of 0.2 mg, 0.5 mg, 0.6 mg, 1.0 mg, 1.25 mg, and 1.8 mg.

In embodiments of the methods of treating HBV infection in a patient in need thereof provided herein, the compound of Formula I is Compound 5, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 5 in the composition is from 0.2 to 1.8 mg. In embodiments, the amount of Compound 5 in the composition is selected from the group consisting of 0.2 mg, 0.6 mg, 1.25 mg, and 1.8 mg. In embodiments, the amount of Compound 5 in the composition is 0.2 mg. In embodiments, the amount of Compound 5 in the composition is 0.6 mg. In embodiments, the amount of Compound 5 in the composition is 1.25 mg. In embodiments, the amount of Compound 5 in the composition is 1.8 mg.

In embodiments of the methods of treating HBV infection in a patient in need thereof provided herein, the compound of Formula I is Compound 6, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 6 in the composition is from 0.2 to 1.8 mg. In embodiments, the amount of Compound 6 in the composition is selected from the group consisting of 0.2 mg, 0.6 mg, 1.25 mg, and 1.8 mg. In embodiments, the amount of Compound 6 in the composition is 0.2 mg. In embodiments, the amount of Compound 6 in the composition is 0.6 mg. In embodiments, the amount of Compound 6 in the composition is 1.25 mg. In embodiments, the amount of Compound 6 in the composition is 1.8 mg.

In embodiments of the methods of treating HBV infection in a patient in need thereof provided herein, the compound of Formula I is Compound 7, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 7 in the composition is from 0.2 to 1.8 mg. In embodiments, the amount of Compound 7 in the composition is selected from the group consisting of 0.2 mg, 0.6 mg, 1.25 mg, and 1.8 mg. In embodiments, the amount of Compound 7 in the composition is 0.2 mg. In embodiments, the amount of Compound 7 in the composition is 0.6 mg. In embodiments, the amount of Compound 7 in the composition is 1.25 mg. In embodiments, the amount of Compound 7 in the composition is 1.8 mg.

In embodiments of the methods of treating HBV infection in a patient in need thereof provided herein, the compound of Formula I is Compound 8, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 8 in the composition is from 0.2 to 1.8 mg. In embodiments, the amount of Compound 8 in the composition is selected from the group consisting of 0.2 mg, 0.6 mg, 1.25 mg, and 1.8 mg. In embodiments, the amount of Compound 8 in the composition is 0.2 mg. In embodiments, the amount of Compound 8 in the composition is 0.6 mg. In embodiments, the amount of Compound 8 in the composition is 1.25 mg. In embodiments, the amount of Compound 8 in the composition is 1.8 mg.

In embodiments of the methods of treating HBV infection in a patient in need thereof provided herein, the compound of Formula I is Compound 9, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 9 in the composition is from 0.2 to 1.8 mg. In embodiments, the amount of Compound 9 in the composition is selected from the group consisting of 0.2 mg, 0.6 mg, 1.25 mg, and 1.8 mg. In embodiments, the amount of Compound 9 in the composition is 0.2 mg. In embodiments, the amount of Compound 9 in the composition is 0.6 mg. In embodiments, the amount of Compound 9 in the composition is 1.25 mg. In embodiments, the amount of Compound 9 in the composition is 1.8 mg.

In embodiments of the methods of treating HBV infection in a patient in need thereof provided herein, the compound of Formula I is Compound 10, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 10 in the composition is from 0.2 to 1.8 mg. In embodiments, the amount of Compound 10 in the composition is selected from the group consisting of 0.2 mg, 0.6 mg, 1.25 mg, and 1.8 mg. In embodiments, the amount of Compound 10 in the composition is 0.2 mg. In embodiments, the amount of Compound 10 in the composition is 0.6 mg. In embodiments, the amount of Compound 10 in the composition is 1.25 mg. In embodiments, the amount of Compound 10 in the composition is 1.8 mg.

In embodiments of the methods of treating HBV infection in a patient in need thereof provided herein, the compound of Formula I is Compound 11, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 11 in the composition is from 0.2 to 1.8 mg. In embodiments, the amount of Compound 11 in the composition is selected from the group consisting of 0.2 mg, 0.6 mg, 1.25 mg, and 1.8 mg. In embodiments, the amount of Compound 11 in the composition is 0.2 mg. In embodiments, the amount of Compound 11 in the composition is 0.6 mg. In embodiments, the amount of Compound 11 in the composition is 1.25 mg. In embodiments, the amount of Compound 11 in the composition is 1.8 mg.

In embodiments of the methods of treating HBV infection in a patient in need thereof provided herein, the compound of Formula I is Compound 12, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 12 in the composition is from 0.2 to 1.8 mg. In embodiments, the amount of Compound 12 in the composition is selected from the group consisting of 0.2 mg, 0.6 mg, 1.25 mg, and 1.8 mg. In embodiments, the amount of Compound 12 in the composition is 0.2 mg. In embodiments, the amount of Compound 12 in the composition is 0.6 mg. In embodiments, the amount of Compound 12 in the composition is 1.25 mg. In embodiments, the amount of Compound 12 in the composition is 1.8 mg.

In embodiments of the methods of treating HBV infection in a patient in need thereof provided herein, the compound of Formula I is Compound 13, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 13 in the composition is from 0.2 to 1.8 mg. In embodiments, the amount of Compound 13 in the composition is selected from the group consisting of 0.2 mg, 0.6 mg, 1.25 mg, and 1.8 mg. In embodiments, the amount of Compound 13 in the composition is 0.2 mg. In embodiments, the amount of Compound 13 in the composition is 0.6 mg. In embodiments, the amount of Compound 13 in the composition is 1.25 mg. In embodiments, the amount of Compound 13 in the composition is 1.8 mg.

In embodiments of the methods of treating HBV infection in a patient in need thereof provided herein, the compound of Formula I is Compound 14, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 14 in the composition is from 0.2 to 1.8 mg. In embodiments, the amount of Compound 14 in the composition is selected from the group consisting of 0.2 mg, 0.6 mg, 1.25 mg, and 1.8 mg. In embodiments, the amount of Compound 14 in the composition is 0.2 mg. In embodiments, the amount of Compound 14 in the composition is 0.6 mg. In embodiments, the amount of Compound 14 in the composition is 1.25 mg. In embodiments, the amount of Compound 14 in the composition is 1.8 mg.

In embodiments of the methods of treating HBV infection in a patient in need thereof provided herein, the compound of Formula I is Compound 15, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 15 in the composition is from 0.2 to 1.8 mg. In embodiments, the amount of Compound 15 in the composition is selected from the group consisting of 0.2 mg, 0.6 mg, 1.25 mg, and 1.8 mg. In embodiments, the amount of Compound 15 in the composition is 0.2 mg. In embodiments, the amount of Compound 15 in the composition is 0.6 mg. In embodiments, the amount of Compound 15 in the composition is 1.25 mg. In embodiments, the amount of Compound 15 in the composition is 1.8 mg.

In embodiments of the methods of treating HBV infection in a patient in need thereof provided herein, the compound of Formula I is Compound 16, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 16 in the composition is from 0.2 to 1.8 mg. In embodiments, the amount of Compound 16 in the composition is selected from the group consisting of 0.2 mg, 0.6 mg, 1.25 mg, and 1.8 mg. In embodiments, the amount of Compound 16 in the composition is 0.2 mg. In embodiments, the amount of Compound 16 in the composition is 0.6 mg. In embodiments, the amount of Compound 16 in the composition is 1.25 mg. In embodiments, the amount of Compound 16 in the composition is 1.8 mg.

In embodiments of the methods of treating HBV infection in a patient in need thereof provided herein, the compound of Formula I is Compound 17, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 17 in the composition is from 0.2 to 1.8 mg. In embodiments, the amount of Compound 17 in the composition is selected from the group consisting of 0.2 mg, 0.6 mg, 1.25 mg, and 1.8 mg. In embodiments, the amount of Compound 17 in the composition is 0.2 mg. In embodiments, the amount of Compound 17 in the composition is 0.6 mg. In embodiments, the amount of Compound 17 in the composition is 1.25 mg. In embodiments, the amount of Compound 17 in the composition is 1.8 mg.

In embodiments of the methods of treating HBV infection in a patient in need thereof provided herein, the compound of Formula I is Compound 18, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 18 in the composition is from 0.2 to 1.8 mg. In embodiments, the amount of Compound 18 in the composition is selected from the group consisting of 0.2 mg, 0.6 mg, 1.25 mg, and 1.8 mg. In embodiments, the amount of Compound 18 in the composition is 0.2 mg. In embodiments, the amount of Compound 18 in the composition is 0.6 mg. In embodiments, the amount of Compound 18 in the composition is 1.25 mg. In embodiments, the amount of Compound 18 in the composition is 1.8 mg.

In embodiments of the methods of treating HBV infection in a patient in need thereof provided herein, the compound of Formula I is Compound 19, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 19 in the composition is from 0.2 to 1.8 mg. In embodiments, the amount of Compound 19 in the composition is selected from the group consisting of 0.2 mg, 0.6 mg, 1.25 mg, and 1.8 mg. In embodiments, the amount of Compound 19 in the composition is 0.2 mg. In embodiments, the amount of Compound 19 in the composition is 0.6 mg. In embodiments, the amount of Compound 19 in the composition is 1.25 mg. In embodiments, the amount of Compound 19 in the composition is 1.8 mg.

In embodiments of the methods of treating HBV infection in a patient in need thereof provided herein, the compound of Formula I is Compound 20, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 20 in the composition is from 0.2 to 1.8 mg. In embodiments, the amount of Compound 20 in the composition is selected from the group consisting of 0.2 mg, 0.6 mg, 1.25 mg, and 1.8 mg. In embodiments, the amount of Compound 20 in the composition is 0.2 mg. In embodiments, the amount of Compound 20 in the composition is 0.6 mg. In embodiments, the amount of Compound 20 in the composition is 1.25 mg. In embodiments, the amount of Compound 20 in the composition is 1.8 mg.

In embodiments of the methods of treating HBV infection in a patient in need thereof provided herein, the compound of Formula I is Compound 21, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 21 in the composition is from 0.2 to 1.8 mg. In embodiments, the amount of Compound 21 in the composition is selected from the group consisting of 0.2 mg, 0.6 mg, 1.25 mg, and 1.8 mg. In embodiments, the amount of Compound 21 in the composition is 0.2 mg. In embodiments, the amount of Compound 21 in the composition is 0.6 mg. In embodiments, the amount of Compound 21 in the composition is 1.25 mg. In embodiments, the amount of Compound 21 in the composition is 1.8 mg.

In embodiments of the methods of treating HBV infection in a patient in need thereof provided herein, the compound of Formula I is Compound 22, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 22 in the composition is from 0.2 to 1.8 mg. In embodiments, the amount of Compound 22 in the composition is selected from the group consisting of 0.2 mg, 0.6 mg, 1.25 mg, and 1.8 mg. In embodiments, the amount of Compound 22 in the composition is 0.2 mg. In embodiments, the amount of Compound 22 in the composition is 0.6 mg. In embodiments, the amount of Compound 22 in the composition is 1.25 mg. In embodiments, the amount of Compound 22 in the composition is 1.8 mg.

In embodiments of the methods of treating HBV infection in a patient in need thereof provided herein, the compound of Formula I is Compound 23, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 23 in the composition is from 0.2 to 1.8 mg. In embodiments, the amount of Compound 23 in the composition is selected from the group consisting of 0.2 mg, 0.6 mg, 1.25 mg, and 1.8 mg. In embodiments, the amount of Compound 23 in the composition is 0.2 mg. In embodiments, the amount of Compound 23 in the composition is 0.6 mg. In embodiments, the amount of Compound 23 in the composition is 1.25 mg. In embodiments, the amount of Compound 23 in the composition is 1.8 mg.

In embodiments of the methods of treating HBV infection in a patient in need thereof provided herein, the compound of Formula I is Compound 24, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 24 in the composition is from 0.2 to 1.8 mg. In embodiments, the amount of Compound 24 in the composition is selected from the group consisting of 0.2 mg, 0.6 mg, 1.25 mg, and 1.8 mg. In embodiments, the amount of Compound 24 in the composition is 0.2 mg. In embodiments, the amount of Compound 24 in the composition is 0.6 mg. In embodiments, the amount of Compound 24 in the composition is 1.25 mg. In embodiments, the amount of Compound 24 in the composition is 1.8 mg.

In embodiments of the methods of treating HBV infection in a patient in need thereof provided herein, the compound of Formula I is Compound 25, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 25 in the composition is from 0.2 to 1.8 mg. In embodiments, the amount of Compound 25 in the composition is selected from the group consisting of 0.2 mg, 0.6 mg, 1.25 mg, and 1.8 mg. In embodiments, the amount of Compound 25 in the composition is 0.2 mg. In embodiments, the amount of Compound 25 in the composition is 0.6 mg. In embodiments, the amount of Compound 25 in the composition is 1.25 mg. In embodiments, the amount of Compound 25 in the composition is 1.8 mg.

In embodiments of the methods of treating HBV infection in a patient in need thereof provided herein, the compound of Formula I is Compound 26, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 26 in the composition is from 0.2 to 1.8 mg. In embodiments, the amount of Compound 26 in the composition is selected from the group consisting of 0.2 mg, 0.6 mg, 1.25 mg, and 1.8 mg. In embodiments, the amount of Compound 26 in the composition is 0.2 mg. In embodiments, the amount of Compound 26 in the composition is 0.6 mg. In embodiments, the amount of Compound 26 in the composition is 1.25 mg. In embodiments, the amount of Compound 26 in the composition is 1.8 mg.

In embodiments of the methods of treating HBV infection in a patient in need thereof provided herein, the compound of Formula I is Compound 27, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 27 in the composition is from 0.2 to 1.8 mg. In embodiments, the amount of Compound 27 in the composition is selected from the group consisting of 0.2 mg, 0.6 mg, 1.25 mg, and 1.8 mg. In embodiments, the amount of Compound 27 in the composition is 0.2 mg. In embodiments, the amount of Compound 27 in the composition is 0.6 mg. In embodiments, the amount of Compound 27 in the composition is 1.25 mg. In embodiments, the amount of Compound 27 in the composition is 1.8 mg.

In embodiments of the methods of treating HBV infection in a patient in need thereof provided herein, the compound of Formula I is Compound 28, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 28 in the composition is from 0.2 to 1.8 mg. In embodiments, the amount of Compound 28 in the composition is selected from the group consisting of 0.2 mg, 0.6 mg, 1.25 mg, and 1.8 mg. In embodiments, the amount of Compound 28 in the composition is 0.2 mg. In embodiments, the amount of Compound 28 in the composition is 0.6 mg. In embodiments, the amount of Compound 28 in the composition is 1.25 mg. In embodiments, the amount of Compound 28 in the composition is 1.8 mg.

In embodiments of the methods of treating HBV infection in a patient in need thereof provided herein, the compound of Formula I is Compound 29, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 29 in the composition is from 0.2 to 1.8 mg. In embodiments, the amount of Compound 29 in the composition is selected from the group consisting of 0.2 mg, 0.6 mg, 1.25 mg, and 1.8 mg. In embodiments, the amount of Compound 29 in the composition is 0.2 mg. In embodiments, the amount of Compound 29 in the composition is 0.6 mg. In embodiments, the amount of Compound 29 in the composition is 1.25 mg. In embodiments, the amount of Compound 29 in the composition is 1.8 mg.

In embodiments of the methods of treating HBV infection in a patient in need thereof provided herein, the compound of Formula I is Compound 30, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 30 in the composition is from 0.2 to 1.8 mg. In embodiments, the amount of Compound 30 in the composition is selected from the group consisting of 0.2 mg, 0.6 mg, 1.25 mg, and 1.8 mg. In embodiments, the amount of Compound 30 in the composition is 0.2 mg. In embodiments, the amount of Compound 30 in the composition is 0.6 mg. In embodiments, the amount of Compound 30 in the composition is 1.25 mg. In embodiments, the amount of Compound 30 in the composition is 1.8 mg.

In embodiments of the methods of treating HBV infection in a patient in need thereof provided herein, the compound of Formula I is Compound 31, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 31 in the composition is from 0.2 to 1.8 mg. In embodiments, the amount of Compound 31 in the composition is selected from the group consisting of 0.2 mg, 0.6 mg, 1.25 mg, and 1.8 mg. In embodiments, the amount of Compound 31 in the composition is 0.2 mg. In embodiments, the amount of Compound 31 in the composition is 0.6 mg. In embodiments, the amount of Compound 31 in the composition is 1.25 mg. In embodiments, the amount of Compound 31 in the composition is 1.8 mg.

In embodiments of the methods of treating HBV infection in a patient in need thereof provided herein, the compound of Formula I is Compound 32, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 32 in the composition is from 0.2 to 1.8 mg. In embodiments, the amount of Compound 32 in the composition is selected from the group consisting of 0.2 mg, 0.6 mg, 1.25 mg, and 1.8 mg. In embodiments, the amount of Compound 32 in the composition is 0.2 mg. In embodiments, the amount of Compound 32 in the composition is 0.6 mg. In embodiments, the amount of Compound 32 in the composition is 1.25 mg. In embodiments, the amount of Compound 32 in the composition is 1.8 mg.

In embodiments of the methods of treating HBV infection in a patient in need thereof provided herein, the compound of Formula I is Compound 33, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 33 in the composition is from 0.2 to 1.8 mg. In embodiments, the amount of Compound 33 in the composition is selected from the group consisting of 0.2 mg, 0.6 mg, 1.25 mg, and 1.8 mg. In embodiments, the amount of Compound 33 in the composition is 0.2 mg. In embodiments, the amount of Compound 33 in the composition is 0.6 mg. In embodiments, the amount of Compound 33 in the composition is 1.25 mg. In embodiments, the amount of Compound 33 in the composition is 1.8 mg.

In embodiments of the methods of treating HBV infection in a patient in need thereof provided herein, the compound of Formula I is Compound 34, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 34 in the composition is from 0.2 to 1.8 mg. In embodiments, the amount of Compound 34 in the composition is selected from the group consisting of 0.2 mg, 0.6 mg, 1.25 mg, and 1.8 mg. In embodiments, the amount of Compound 34 in the composition is 0.2 mg. In embodiments, the amount of Compound 34 in the composition is 0.6 mg. In embodiments, the amount of Compound 34 in the composition is 1.25 mg. In embodiments, the amount of Compound 34 in the composition is 1.8 mg.

In embodiments of the methods of treating HBV infection in a patient in need thereof provided herein, the compound of Formula I is Compound 35, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 35 in the composition is from 0.2 to 1.8 mg. In embodiments, the amount of Compound 35 in the composition is selected from the group consisting of 0.2 mg, 0.6 mg, 1.25 mg, and 1.8 mg. In embodiments, the amount of Compound 35 in the composition is 0.2 mg. In embodiments, the amount of Compound 35 in the composition is 0.6 mg. In embodiments, the amount of Compound 35 in the composition is 1.25 mg. In embodiments, the amount of Compound 35 in the composition is 1.8 mg.

In embodiments of the methods of treating HBV infection in a patient in need thereof provided herein, the compound of Formula I is Compound 36, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 36 in the composition is from 0.2 to 1.8 mg. In embodiments, the amount of Compound 36 in the composition is selected from the group consisting of 0.2 mg, 0.6 mg, 1.25 mg, and 1.8 mg. In embodiments, the amount of Compound 36 in the composition is 0.2 mg. In embodiments, the amount of Compound 36 in the composition is 0.6 mg. In embodiments, the amount of Compound 36 in the composition is 1.25 mg. In embodiments, the amount of Compound 36 in the composition is 1.8 mg.

In embodiments of the methods of treating HBV infection in a patient in need thereof provided herein, the compound of Formula I is Compound 37, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 37 in the composition is from 0.2 to 1.8 mg. In embodiments, the amount of Compound 37 in the composition is selected from the group consisting of 0.2 mg, 0.6 mg, 1.25 mg, and 1.8 mg. In embodiments, the amount of Compound 37 in the composition is 0.2 mg. In embodiments, the amount of Compound 37 in the composition is 0.6 mg. In embodiments, the amount of Compound 37 in the composition is 1.25 mg. In embodiments, the amount of Compound 37 in the composition is 1.8 mg.

In embodiments of the methods of treating HBV infection in a patient in need thereof provided herein, the compound of Formula I is Compound 38, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 38 in the composition is from 0.2 to 1.8 mg. In embodiments, the amount of Compound 38 in the composition is selected from the group consisting of 0.2 mg, 0.6 mg, 1.25 mg, and 1.8 mg. In embodiments, the amount of Compound 38 in the composition is 0.2 mg. In embodiments, the amount of Compound 38 in the composition is 0.6 mg. In embodiments, the amount of Compound 38 in the composition is 1.25 mg. In embodiments, the amount of Compound 38 in the composition is 1.8 mg.

In embodiments of the methods of treating HBV infection in a patient in need thereof provided herein, the compound of Formula I is Compound 39, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 39 in the composition is from 0.2 to 1.8 mg. In embodiments, the amount of Compound 39 in the composition is selected from the group consisting of 0.2 mg, 0.6 mg, 1.25 mg, and 1.8 mg. In embodiments, the amount of Compound 39 in the composition is 0.2 mg. In embodiments, the amount of Compound 39 in the composition is 0.6 mg. In embodiments, the amount of Compound 39 in the composition is 1.25 mg. In embodiments, the amount of Compound 39 in the composition is 1.8 mg.

In embodiments of the methods of treating HBV infection in a patient in need thereof provided herein, the compound of Formula I is Compound 40, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 40 in the composition is from 0.2 to 1.8 mg. In embodiments, the amount of Compound 40 in the composition is selected from the group consisting of 0.2 mg, 0.6 mg, 1.25 mg, and 1.8 mg. In embodiments, the amount of Compound 40 in the composition is 0.2 mg. In embodiments, the amount of Compound 40 in the composition is 0.6 mg. In embodiments, the amount of Compound 40 in the composition is 1.25 mg. In embodiments, the amount of Compound 40 in the composition is 1.8 mg.

In embodiments of the methods of treating HBV infection in a patient in need thereof provided herein, the compound of Formula I is Compound 41, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 41 in the composition is from 0.2 to 1.8 mg. In embodiments, the amount of Compound 41 in the composition is selected from the group consisting of 0.2 mg, 0.6 mg, 1.25 mg, and 1.8 mg. In embodiments, the amount of Compound 41 in the composition is 0.2 mg. In embodiments, the amount of Compound 41 in the composition is 0.6 mg. In embodiments, the amount of Compound 41 in the composition is 1.25 mg. In embodiments, the amount of Compound 41 in the composition is 1.8 mg.

In embodiments of the methods of treating HBV infection in a patient in need thereof provided herein, the compound of Formula I is Compound 42, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 42 in the composition is from 0.2 to 1.8 mg. In embodiments, the amount of Compound 42 in the composition is selected from the group consisting of 0.2 mg, 0.6 mg, 1.25 mg, and 1.8 mg. In embodiments, the amount of Compound 42 in the composition is 0.2 mg. In embodiments, the amount of Compound 42 in the composition is 0.6 mg. In embodiments, the amount of Compound 42 in the composition is 1.25 mg. In embodiments, the amount of Compound 42 in the composition is 1.8 mg.

In embodiments of the methods of treating HBV infection in a patient in need thereof provided herein, the compound of Formula I is Compound 43, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 43 in the composition is from 0.2 to 1.8 mg. In embodiments, the amount of Compound 43 in the composition is selected from the group consisting of 0.2 mg, 0.6 mg, 1.25 mg, and 1.8 mg. In embodiments, the amount of Compound 43 in the composition is 0.2 mg. In embodiments, the amount of Compound 43 in the composition is 0.6 mg. In embodiments, the amount of Compound 43 in the composition is 1.25 mg. In embodiments, the amount of Compound 43 in the composition is 1.8 mg.

In embodiments of the methods of treating HBV infection in a patient in need thereof provided herein, the compound of Formula I is Compound 44, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 44 in the composition is from 0.2 to 1.8 mg. In embodiments, the amount of Compound 44 in the composition is selected from the group consisting of 0.2 mg, 0.6 mg, 1.25 mg, and 1.8 mg. In embodiments, the amount of Compound 44 in the composition is 0.2 mg. In embodiments, the amount of Compound 44 in the composition is 0.6 mg. In embodiments, the amount of Compound 44 in the composition is 1.25 mg. In embodiments, the amount of Compound 44 in the composition is 1.8 mg.

In embodiments of the methods of treating HBV infection in a patient in need thereof provided herein, the compound of Formula I is Compound 45, or a pharmaceutically acceptable salt thereof, in an amount from 0.1 mg to 2.5 mg (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg). In embodiments, the amount of Compound 45 in the composition is from 0.2 to 1.8 mg. In embodiments, the amount of Compound 45 in the composition is selected from the group consisting of 0.2 mg, 0.6 mg, 1.25 mg, and 1.8 mg. In embodiments, the amount of Compound 45 in the composition is 0.2 mg. In embodiments, the amount of Compound 45 in the composition is 0.6 mg. In embodiments, the amount of Compound 45 in the composition is 1.25 mg. In embodiments, the amount of Compound 45 in the composition is 1.8 mg.

The compounds described herein are disclosed in US Patent Application Publication No. US 2017/0273983, which is hereby incorporated by reference in its entirety. The synthesis of the compounds described herein is also disclosed in this publication.

In certain embodiments of the methods of treating HBV infection provided herein, the treatment is curative and the patient does not have to continue treatment after the specified treatment time. In a particular embodiment of the method of treating HBV provided herein, the treatment is finite.

In an aspect, provided herein are methods of reducing the viral load associated with an HBV infection in a subject in need thereof, comprising administering to the subject a therapeutically effective amount of the compositions described above.

In an aspect, provided herein are methods of reducing reoccurrence of an HBV infection in a subject in need thereof, comprising administering to the subject a therapeutically effective amount of the compositions described above.

In an aspect, provided herein are methods of reducing an adverse physiological impact of an HBV infection in a subject in need thereof, comprising administering to the subject a therapeutically effective amount of the compositions described above.

In an aspect, provided herein are methods of inducing remission of hepatic injury from an HBV infection in a subject in need thereof, comprising administering to the subject a therapeutically effective amount of the compositions described above.

In an aspect, provided herein are methods of treating a latent HBV infection in a subject in need thereof, comprising administering to the subject a therapeutically effective amount of the compositions described above.

In embodiments, the methods further comprise administering to the subject at least one additional therapeutic agent selected from the group consisting of HBV polymerase inhibitors, nucleic acid analogs, interferons, viral entry inhibitors, viral maturation inhibitors, capsid assembly modulators, reverse transcriptase inhibitors, TLR-agonists, small interfering RNAs, antisense oligonucleotides, nucleic acid polymers and a combination thereof.

Patients who can be treated using the described methods are in some embodiments human. Other warm-blooded animals can also be treated.

In embodiments of the methods of treating HBV infection provided herein, the patient in need thereof is a chronically HBV-infected patient, with or without evidence of underlying liver inflammation. In some embodiments, the patient has a chronic HBV infection. In other embodiments, the patient is suffering from an HBV-induced disease. In some embodiments, the HBV-induced disease is cirrhosis, liver failure or hepatocellular carcinoma. In other embodiments, the patient is a treatment-naïve patient. More in particular, the patient is a chronically HBV-infected treatment-naïve patient. In a further embodiment, the patient is HBeAg-positive. In still a further embodiment, the patient is treatment-naïve and HBeAg-positive.

HBV infections that can be treated according to the disclosed methods include HBV genotype A, B, C, and/or D infections. However, in embodiments, the methods disclosed can treat any HBV genotype ("pan-genotypic treatment"). HBV genotyping can be performed using methods known in the art, for example, INNO-LIPA® HBV Genotyping, Innogenetics N.V., Ghent, Belgium).

In an additional embodiment, provided herein is a method of reducing serum HBV DNA in a patient comprising administering to the patient in need thereof a compound of Formula I, or a pharmaceutically acceptable salt thereof, in an amount from 0.1 mg to 2.5 mg per day.

In embodiments, provided herein is a method of reducing serum HBV DNA in a patient comprising administering to the patient in need thereof a compound of Formula I, or a pharmaceutically acceptable salt thereof, in an amount from 0.1 mg to 2.5 mg per day.

In further embodiments, the disclosure relates to a method of reducing serum HBV RNA in a patient comprising administering to the patient in need thereof a compound of Formula I, or a pharmaceutically acceptable salt thereof, in an amount from 0.1 mg to 2.5 mg per day.

In additional embodiments, the disclosure relates to a method of reducing serum HBeAg in a patient comprising administering to the patient in need thereof a compound of Formula I, or a pharmaceutically acceptable salt thereof, in an amount from 0.1 mg to 2.5 mg per day.

Serum HBV DNA quantitation can be performed according to methods known in the art, for example, using the polymerase chain reaction (PCR)-based assay COBAS® TAQMAN® HBV Test v2.0 (Roche Diagnostics), which has been validated to quantify HBV DNA from serum samples for diverse HBV genotypes (A-H) including pre-core mutant HBV strains, with a reported lower limit of detection of 35 IU/mL and a linear dynamic range of quantitation of $1.7 \times 10^2$ to $8.5 \times 10^8$ IU/mL IU/mL, using the WHO pooled serum reference standard for quantitation.

Serum HBsAg and HBeAg levels can be measured using for example, the investigational Abbott ARCHITECT™ assays (Abbott Laboratories; Abbott Park, IL, USA).

In an aspect, provided herein is a method of decreasing formation of HBV cccDNA in a subject infected with HBV or at risk of being infected with HBV, said method comprising administering to said subject a compound of Formula I at a daily dose of 0.1 mg to 2.5 mg.

In an aspect, provided herein is a method of decreasing HBsAg in a subject infected with HBV or at risk of being infected with HBV, said method comprising administering to said subject a compound of Formula I at a daily dose of 0.2-1.8 mg.

In embodiments, provided herein is a method of decreasing HBsAg in a subject infected with HBV or at risk of being infected with HBV, said method comprising administering to said subject a compound of Formula I at a daily dose of 0.2 mg.

In embodiments, provided herein is a method of decreasing HBsAg in a subject infected with HBV or at risk of being infected with HBV, said method comprising administering to said subject a compound of Formula I at a daily dose 0.5 mg.

In embodiments, provided herein is a method of decreasing HBsAg in a subject infected with HBV or at risk of being infected with HBV, said method comprising administering to said subject a compound of Formula I at a daily dose 0.6 mg.

In embodiments, provided herein is a method of decreasing HBsAg in a subject infected with HBV or at risk of being infected with HBV, said method comprising administering to said subject a compound of Formula I at a daily dose 1.0 mg.

In embodiments, provided herein is a method of decreasing HBsAg in a subject infected with HBV or at risk of being infected with HBV, said method comprising administering to said subject a compound of Formula I at a daily dose 1.25 mg.

In embodiments, provided herein is a method of decreasing HBsAg in a subject infected with HBV or at risk of being infected with HBV, said method comprising administering to said subject a compound of Formula I at a daily dose 1.8 mg.

In an aspect, provided herein is a method of preventing HBV infection in a subject at risk of being infected with HBV by decreasing formation of HBV cccDNA, said method comprising administering to said subject a compound of Formula I at a daily dose of 0.1-2.5 mg.

In an aspect of the methods provided herein, the particular dosing strategy results in inhibition of DANE particles, RNA-containing particles, and double-stranded DNA particles but does not inhibit subviral particles containing HBsAg.

In an aspect of the methods provided herein, the particular dosing strategy results in the inhibition of cccDNA, which results in inhibition of subviral particles containing HBsAg.

In some embodiments, the administration of a compound of Formula I is performed for an administration period of 24 weeks. In embodiments, the administration of a compound of Formula I is performed for an administration period of longer than 24 weeks. In embodiments, the administration of a compound of Formula I is performed for an administration period shorter than 24 weeks (e.g., 10, 12, 14, 16, 18, 20, or 22 weeks). In embodiments, a compound of Formula I is administered for a duration of 28 days. In embodiments, a compound of Formula I is administered for a duration of 48 weeks. In embodiments, a compound of Formula I is administered for a duration of longer than 48 weeks. In embodiments, a compound of Formula I is administered for a duration of at least four weeks.

In some embodiments, the administration of any of Compounds 1-45 is performed for an administration period of 24 weeks. In embodiments, the administration of any of Compounds 1-45 is performed for an administration period of longer than 24 weeks. In embodiments, the administration any of Compounds 1-45 is performed for an administration period shorter than 24 weeks (e.g., 10, 12, 14, 16, 18, 20, or 22 weeks). In embodiments, any of Compounds 1-45 are administered for a duration of 28 days. In embodiments, any of Compounds 1-45 are administered for a duration of 48 weeks. In embodiments, any of Compounds 1-45 are administered for a duration of longer than 48 weeks. In embodiments, any of Compounds 1-45 are administered for a duration of at least four weeks.

The daily doses described herein are calculated for an average body weight of 60 to 70 kg and should be recalculated in case of paediatric applications, or when used with patients with a substantially diverting body weight.

In an aspect, provided herein is a pharmaceutical composition for use in a method for the treatment of an HBV infection in a subject in need thereof, the composition comprising at least one TLR-7 agonist and at least one pharmaceutically acceptable excipient;

wherein the TLR-7 agonist is a compound of Formula I:

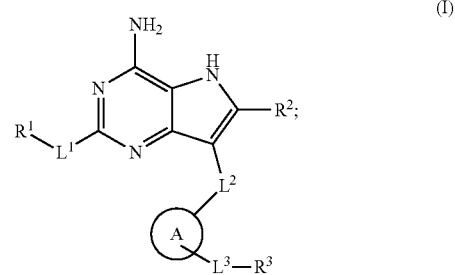

(I)

or a pharmaceutically acceptable salt thereof;
wherein:
$L^1$ is —O—;
$L^2$ is —CH$_2$—;
$R^1$ is selected from the group consisting of —H and —C$_1$-C$_{10}$ alkyl; wherein the alkyl is optionally substituted by one or more $R^4$ groups;
$R^2$ is selected from the group consisting of —H, —CN, —COOH, and —CONH$_2$;
ring A is selected from the group consisting of aryl and heteroaryl;
$L^3$ is selected from the group consisting of C$_0$-C$_6$ alkylene and imino; wherein alkylene and imino are optionally substituted by one or more $R^4$ groups;
$R^3$ is selected from the group consisting of —H, amino, C$_1$-C$_{10}$ alkyl, C$_3$-C$_{10}$ cycloalkyl, and 3-10 membered heterocycloalkyl; wherein amino, alkyl, cycloalkyl, and heterocycloalkyl are optionally substituted by one or more $R^4$ groups;
or wherein $R^3$ and $L^3$, together with the atom to which $L^3$ is attached and the adjacent atom in ring A, form a saturated or unsaturated 5-8 membered ring, which is optionally substituted by one or more $R^4$ groups;
$R^4$ is, independently at each occurrence, selected from the group consisting of —R, —OR, and =O; and
R is, independently at each occurrence, selected from the group consisting of H and C$_1$-C$_8$ alkyl;
wherein the method of treatment comprises administering, more particularly orally administering, the pharmaceutical composition to the human subject, and wherein the amount of the compound of Formula I in the composition is from 0.1 to 2.5 mg.

In embodiments of the use, $L^1$, $L^2$, $R^1$, $R^2$, and $L^3$ have the definitions provided above, and $R^3$ is selected from the group consisting of —H, amino, C$_1$-C$_{10}$ alkyl, C$_3$-C$_{10}$ cycloalkyl, and 3-10 membered heterocycloalkyl; wherein amino, alkyl, cycloalkyl, and heterocycloalkyl are optionally substituted by one or more $R^4$ groups;

R⁴ is, independently at each occurrence, selected from the group consisting of —R, —OR, and =O; and R is, independently at each occurrence, selected from the group consisting of H, halo, and $C_1$-$C_8$ alkyl.

In embodiments of the use, $R^3$ is 3-10 membered heterocycloalkyl substituted by halo.

In embodiments of the use, $L^1$ is —O—;

$L^2$ is —CH₂—;

$R^1$ is selected from the group consisting of —H and —$C_1$-$C_{10}$ alkyl;

$R^2$ is selected from the group consisting of —H and —CONH₂;

ring A is selected from the group consisting of aryl and heteroaryl;

$L^3$ is $C_0$-$C_6$ alkylene; and $R^3$ is 3-10 membered heterocycloalkyl.

In embodiments of the use, the at least one compound of Formula I is Compound 1, or a pharmaceutically acceptable salt thereof. In embodiments of the use, the at least one compound of Formula I is Compound 2, or a pharmaceutically acceptable salt thereof. In embodiments of the use, the at least one compound of Formula I is Compound 3, or a pharmaceutically acceptable salt thereof. In embodiments of the use, the at least one compound of Formula I is Compound 4, or a pharmaceutically acceptable salt thereof. In embodiments of the use, the at least one compound of Formula I is Compound 5, or a pharmaceutically acceptable salt thereof. In embodiments of the use, the at least one compound of Formula I is Compound 6, or a pharmaceutically acceptable salt thereof. In embodiments of the use, the at least one compound of Formula I is Compound 7, or a pharmaceutically acceptable salt thereof. In embodiments of the use, the at least one compound of Formula I is Compound 8, or a pharmaceutically acceptable salt thereof.

In embodiments of the use, the at least one compound of Formula I is Compound 9, or a pharmaceutically acceptable salt thereof. In embodiments of the use, the at least one compound of Formula I is Compound 10, or a pharmaceutically acceptable salt thereof. In embodiments of the use, the at least one compound of Formula I is Compound 11, or a pharmaceutically acceptable salt thereof. In embodiments of the use, the at least one compound of Formula I is Compound 12, or a pharmaceutically acceptable salt thereof. In embodiments of the use, the at least one compound of Formula I is Compound 13, or a pharmaceutically acceptable salt thereof. In embodiments of the use, the at least one compound of Formula I is Compound 14, or a pharmaceutically acceptable salt thereof. In embodiments of the use, the at least one compound of Formula I is Compound 15, or a pharmaceutically acceptable salt thereof. In embodiments of the use, the at least one compound of Formula I is Compound 16, or a pharmaceutically acceptable salt thereof.

In embodiments of the use, the at least one compound of Formula I is Compound 17, or a pharmaceutically acceptable salt thereof. In embodiments of the use, the at least one compound of Formula I is Compound 18, or a pharmaceutically acceptable salt thereof. In embodiments of the use, the at least one compound of Formula I is Compound 19, or a pharmaceutically acceptable salt thereof. In embodiments of the use, the at least one compound of Formula I is Compound 20, or a pharmaceutically acceptable salt thereof. In embodiments of the use, the at least one compound of Formula I is Compound 21, or a pharmaceutically acceptable salt thereof. In embodiments of the use, the at least one compound of Formula I is Compound 22, or a pharmaceutically acceptable salt thereof. In embodiments of the use, the at least one compound of Formula I is Compound 23, or a pharmaceutically acceptable salt thereof. In embodiments of the use, the at least one compound of Formula I is Compound 24, or a pharmaceutically acceptable salt thereof.

In embodiments of the use, the at least one compound of Formula I is Compound 25, or a pharmaceutically acceptable salt thereof. In embodiments of the use, the at least one compound of Formula I is Compound 26, or a pharmaceutically acceptable salt thereof. In embodiments of the use, the at least one compound of Formula I is Compound 27, or a pharmaceutically acceptable salt thereof. In embodiments of the use, the at least one compound of Formula I is Compound 28, or a pharmaceutically acceptable salt thereof. In embodiments of the use, the at least one compound of Formula I is Compound 29, or a pharmaceutically acceptable salt thereof. In embodiments of the use, the at least one compound of Formula I is Compound 30, or a pharmaceutically acceptable salt thereof. In embodiments of the use, the at least one compound of Formula I is Compound 31, or a pharmaceutically acceptable salt thereof. In embodiments of the use, the at least one compound of Formula I is Compound 32, or a pharmaceutically acceptable salt thereof.

In embodiments of the use, the at least one compound of Formula I is Compound 33, or a pharmaceutically acceptable salt thereof. In embodiments of the use, the at least one compound of Formula I is Compound 34, or a pharmaceutically acceptable salt thereof. In embodiments of the use, the at least one compound of Formula I is Compound 35, or a pharmaceutically acceptable salt thereof. In embodiments of the use, the at least one compound of Formula I is Compound 36, or a pharmaceutically acceptable salt thereof. In embodiments of the use, the at least one compound of Formula I is Compound 37, or a pharmaceutically acceptable salt thereof. In embodiments of the use, the at least one compound of Formula I is Compound 38, or a pharmaceutically acceptable salt thereof. In embodiments of the use, the at least one compound of Formula I is Compound 39, or a pharmaceutically acceptable salt thereof. In embodiments of the use, the at least one compound of Formula I is Compound 40, or a pharmaceutically acceptable salt thereof.

In embodiments of the use, the at least one compound of Formula I is Compound 41, or a pharmaceutically acceptable salt thereof. In embodiments of the use, the at least one compound of Formula I is Compound 42, or a pharmaceutically acceptable salt thereof. In embodiments of the use, the at least one compound of Formula I is Compound 43, or a pharmaceutically acceptable salt thereof. In embodiments of the use, the at least one compound of Formula I is Compound 44, or a pharmaceutically acceptable salt thereof. In embodiments of the use, the at least one compound of Formula I is Compound 45, or a pharmaceutically acceptable salt thereof.

In embodiments of the use, the amount of the at least one compound of Formula I in the composition is from 0.2 to 1.8 mg. In embodiments, the amount of Compound 4 in the composition is selected from the group consisting of 0.2 mg, 0.6 mg, 1.25 mg, and 1.8 mg. In embodiments of the use, the amount of the compound of Formula I in the composition is selected from the group consisting of 0.2 mg, 0.5 mg, 0.6 mg, 1.0 mg, 1.25 mg, and 1.8 mg, more particularly 0.2 mg, 0.6 mg, 1.25 mg, and 1.8 mg. In embodiments of the use, the amount of the at least one compound of Formula I in the composition is 0.2 mg. In embodiments of the use, the amount of the at least one compound of Formula I in the composition is 0.5 mg. In embodiments of the use, the amount of the at least one compound of Formula I in the composition is 0.6 mg. In embodiments of the use, the amount of the at least one compound of Formula I in the composition is 1.0 mg. In embodiments of the use, the amount of the at least one compound of Formula I in the composition is 1.25 mg. In embodiments of the use, the amount of the at least one compound of Formula I in the composition is 1.8 mg.

In embodiments of the use, the compound of Formula I is administered at a dose of 0.1 to 2.5 mg. In embodiments of the use, the compound of Formula I is administered at a single dose of 0.1 to 2.5 mg. In embodiments of the use, the compound of Formula I is administered at multiple doses, wherein each individual dose of said multiple doses is of 0.1 to 2.5 mg. In embodiments of the use, the compound of Formula I is administered once daily (qd), once weekly (qw), or once every two weeks (q2w). In embodiments of the use, the compound of Formula I is administered once daily (qd). In embodiments of the use, the compound of Formula I is administered once weekly (qw). In embodiments of the use, the compound of Formula I is administered once every two weeks (q2w). In embodiments of the use, the compound of Formula I is administered once daily (qd), once weekly (qw), or once every two weeks (q2w) for at least four weeks. In embodiments of the use, the compound of Formula I is administered once daily (qd) for at least four weeks. In embodiments of the use, the compound of Formula I is administered once weekly (qw) for at least four weeks. In embodiments of the use, the compound of Formula I is administered once every two weeks (q2w) for at least four weeks. In embodiments of the use, the compound of Formula I is administered once daily (qd) in an amount selected from the group consisting of 0.2 mg, 0.5 mg, 0.6 mg, 1.0 mg, 1.25 mg, and 1.8 mg. In embodiments of the use, the compound of Formula I is administered once weekly (qw) in an amount selected from the group consisting of 0.2 mg, 0.5 mg, 0.6 mg, 1.0 mg, 1.25 mg, and 1.8 mg. In embodiments of the use, the compound of Formula I is administered once every two weeks (q2w) in an amount selected from the group consisting of 0.2 mg, 0.5 mg, 0.6 mg, 1.0 mg, 1.25 mg, and 1.8 mg.

In embodiments of the use, the composition is formulated as an oral solution. In embodiments of the use, the composition is formulated as a solid, oral tablet. In embodiments of the use, the composition is formulated as an aqueous solution in citrate buffer. In embodiments of the use, the concentration of the citrate buffer is 50 mM. In embodiments of the use, the pH of the citrate buffer is 4-5. In embodiments of the use, the pH of the citrate buffer is 4. In embodiments, the pH of the citrate buffer is 5.

In embodiments of the use, the composition comprises:
a compound of Formula I;
citric acid monohydrate;
sodium hydroxide solution; and
water.

In embodiments of the use, the composition comprises:
0.05-0.2 mg/mL of a compound of Formula I;
50 mM citric acid monohydrate;
sodium hydroxide solution; and
water. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
0.9-1.1 mg/mL of a compound of Formula I;
50 mM citric acid monohydrate;
sodium hydroxide solution; and
water. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
0.1-0.3 mg of a compound of Formula I;
50 mM citric acid monohydrate;
sodium hydroxide solution; and
water. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
0.5-0.7 mg of a compound of Formula I;
50 mM citric acid monohydrate;
sodium hydroxide solution; and
water. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
1.0-1.4 mg of a compound of Formula I;
50 mM citric acid monohydrate;
sodium hydroxide solution; and
water. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
1.7-1.9 mg of a compound of Formula I;
50 mM citric acid monohydrate;
sodium hydroxide solution; and
water. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
0.2 mg of a compound of Formula I;
50 mM citric acid monohydrate;
sodium hydroxide solution; and
water. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
0.5 mg of a compound of Formula I;
50 mM citric acid monohydrate;
sodium hydroxide solution; and
water. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
0.6 mg of a compound of Formula I;
50 mM citric acid monohydrate;
sodium hydroxide solution; and
water. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
1.0 mg of a compound of Formula I;
50 mM citric acid monohydrate;
sodium hydroxide solution; and
water. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
1.25 mg of a compound of Formula I;
50 mM citric acid monohydrate;
sodium hydroxide solution; and
water. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
1.8 mg of a compound of Formula I;
50 mM citric acid monohydrate;
sodium hydroxide solution; and
water. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
a compound of Formula I;
silicified microcrystalline cellulose;
croscarmellose sodium;
magnesium stearate;
polyvinyl alcohol;
polyethylene glycol;
titanium dioxide;
and talc. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
0.5 mg of a compound of Formula I;
silicified microcrystalline cellulose;
croscarmellose sodium;
magnesium stearate;
polyvinyl alcohol;
polyethylene glycol;
titanium dioxide;
and talc. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
1.0 mg of a compound of Formula I;
silicified microcrystalline cellulose;
croscarmellose sodium;
magnesium stearate;
polyvinyl alcohol;
polyethylene glycol;
titanium dioxide;
and talc. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w). In embodiments of the use, the polyvinyl alcohol is USP/Ph.Eur polyvinyl alcohol.

In embodiments of the use, the composition comprises:
0.1 mg/mL of a compound of Formula I;
50 mM citric acid monohydrate;
sodium hydroxide solution; and
water.

In embodiments of the use, the composition comprises:
1.0 mg/mL of a compound of Formula I;
50 mM citric acid monohydrate;
sodium hydroxide solution; and
water.

In embodiments of the use, the composition comprises:
Compound 1;
citric acid monohydrate;
sodium hydroxide solution; and
water.

In embodiments of the use, the composition comprises:
0.1 mg/mL of Compound 1;
50 mM citric acid monohydrate;
sodium hydroxide solution; and
water.

In embodiments of the use, the composition comprises:
1.0 mg/mL of Compound 1;
50 mM citric acid monohydrate;
sodium hydroxide solution; and
water.

In embodiments of the use, the composition comprises:
Compound 2;
citric acid monohydrate;
sodium hydroxide solution; and
water.

In embodiments of the use, the composition comprises:
0.1 mg/mL of Compound 2;
50 mM citric acid monohydrate;
sodium hydroxide solution; and
water.

In embodiments of the use, the composition comprises:
1.0 mg/mL of Compound 2;
50 mM citric acid monohydrate;
sodium hydroxide solution; and
water.

In embodiments of the use, the composition comprises:
Compound 3;
citric acid monohydrate;
sodium hydroxide solution; and
water.

In embodiments of the use, the composition comprises:
0.1 mg/mL of Compound 3;
50 mM citric acid monohydrate;
sodium hydroxide solution; and
water.

In embodiments of the use, the composition comprises:
1.0 mg/mL of Compound 3;
50 mM citric acid monohydrate;
sodium hydroxide solution; and
water.

In embodiments of the use, the composition comprises:
Compound 4;
citric acid monohydrate;
sodium hydroxide solution; and
water. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
0.05-0.2 mg/mL of Compound 4;
50 mM citric acid monohydrate;
sodium hydroxide solution; and
water. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
0.9-1.1 mg/mL of Compound 4;
50 mM citric acid monohydrate;
sodium hydroxide solution; and
water. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
0.1 mg/mL of Compound 4;
50 mM citric acid monohydrate;
sodium hydroxide solution; and
water. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
1.0 mg/mL of Compound 4;
50 mM citric acid monohydrate;
sodium hydroxide solution; and
water. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
0.1-0.3 mg of Compound 4;
50 mM citric acid monohydrate;
sodium hydroxide solution; and
water. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
0.5-0.7 mg of Compound 4;
50 mM citric acid monohydrate;
sodium hydroxide solution; and
water. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
1.0-1.4 mg of Compound 4;
50 mM citric acid monohydrate;
sodium hydroxide solution; and
water. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
1.7-1.9 mg of Compound 4;
50 mM citric acid monohydrate;
sodium hydroxide solution; and
water. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
0.2 mg of Compound 4;
50 mM citric acid monohydrate;
sodium hydroxide solution; and
water. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
0.5 mg of Compound 4;
50 mM citric acid monohydrate;
sodium hydroxide solution; and
water. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w)

In embodiments of the use, the composition comprises:
0.6 mg of Compound 4;
50 mM citric acid monohydrate;
sodium hydroxide solution; and
water. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
1.0 mg of Compound 4;
50 mM citric acid monohydrate;
sodium hydroxide solution; and
water. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
1.25 mg of Compound 4;
50 mM citric acid monohydrate;
sodium hydroxide solution; and
water. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
1.8 mg Compound 4;
50 mM citric acid monohydrate;
sodium hydroxide solution; and
water. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w). In embodiments of the use, the composition comprises: Compound 4;
silicified microcrystalline cellulose;
croscarmellose sodium;
magnesium stearate;
polyvinyl alcohol;
polyethylene glycol;
titanium dioxide;
and talc. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
0.5 mg of Compound 4;
silicified microcrystalline cellulose;
croscarmellose sodium;
magnesium stearate;
polyvinyl alcohol;
polyethylene glycol;
titanium dioxide;
and talc. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w).

In embodiments of the use, the composition comprises:
1.0 mg of Compound 4;
silicified microcrystalline cellulose;
croscarmellose sodium;
magnesium stearate;
polyvinyl alcohol;
polyethylene glycol;
titanium dioxide;
and talc. In embodiments of the use, the composition is administered once daily (qd), once weekly (qw), or once every two weeks (q2w). In embodiments of the use, the composition is administered once daily (qd). In embodiments of the use, the composition is administered once weekly (qw). In embodiments of the use, the composition is administered once every two weeks (q2w). In embodiments of the use, the polyvinyl alcohol is
USP/Ph.Eur polyvinyl alcohol.

In embodiments of the use, the composition comprises:
Compound 5;
citric acid monohydrate;
sodium hydroxide solution; and
water.
In embodiments of the use, the composition comprises:
0.1 mg/mL of Compound 5;
50 mM citric acid monohydrate;
sodium hydroxide solution; and
water.
In embodiments of the use, the composition comprises:
1.0 mg/mL of Compound 5;
50 mM citric acid monohydrate;
sodium hydroxide solution; and
water.
In embodiments of the use, the composition comprises:
Compound 6;
citric acid monohydrate;
sodium hydroxide solution; and
water.
In embodiments of the use, the composition comprises:
0.1 mg/mL of Compound 6;
50 mM citric acid monohydrate;
sodium hydroxide solution; and
water.
In embodiments of the use, the composition comprises:
1.0 mg/mL of Compound 6;
50 mM citric acid monohydrate;
sodium hydroxide solution; and
water.
In embodiments of the use, the composition comprises:
Compound 7;
citric acid monohydrate;
sodium hydroxide solution; and
water.
In embodiments of the use, the composition comprises:
0.1 mg/mL of Compound 7;
50 mM citric acid monohydrate;
sodium hydroxide solution; and
water.
In embodiments of the use, the composition comprises:
1.0 mg/mL of Compound 7;
50 mM citric acid monohydrate;
sodium hydroxide solution; and
water.
In embodiments of the use, the composition comprises:
Compound 8;
citric acid monohydrate;
sodium hydroxide solution; and
water.
In embodiments of the use, the composition comprises:
0.1 mg/mL of Compound 8;
50 mM citric acid monohydrate;
sodium hydroxide solution; and
water.
In embodiments of the use, the composition comprises:
1.0 mg/mL of Compound 8;
50 mM citric acid monohydrate;
sodium hydroxide solution; and
water.
In embodiments of the use, the composition comprises:
Compound 9;
citric acid monohydrate;
sodium hydroxide solution; and
water.
In embodiments of the use, the composition comprises:
0.1 mg/mL of Compound 9;
50 mM citric acid monohydrate;
sodium hydroxide solution; and
water.
In embodiments of the use, the composition comprises:
1.0 mg/mL of Compound 9;
50 mM citric acid monohydrate;
sodium hydroxide solution; and
water.
In embodiments of the use, the composition comprises:
Compound 10;
citric acid monohydrate;
sodium hydroxide solution; and
water.
In embodiments of the use, the composition comprises:
0.1 mg/mL of Compound 10;
50 mM citric acid monohydrate;
sodium hydroxide solution; and
water.
In embodiments of the use, the composition comprises:
1.0 mg/mL of Compound 10;
50 mM citric acid monohydrate;
sodium hydroxide solution; and
water.
In embodiments of the use, the composition comprises:
Compound 11;
citric acid monohydrate;
sodium hydroxide solution; and
water.
In embodiments of the use, the composition comprises:
0.1 mg/mL of Compound 11;
50 mM citric acid monohydrate;
sodium hydroxide solution; and
water.
In embodiments of the use, the composition comprises:
1.0 mg/mL of Compound 11;
50 mM citric acid monohydrate;
sodium hydroxide solution; and
water.
In embodiments of the use, the composition comprises:
Compound 12;
citric acid monohydrate;
sodium hydroxide solution; and
water.
In embodiments of the use, the composition comprises:
0.1 mg/mL of Compound 12;
50 mM citric acid monohydrate;
sodium hydroxide solution; and
water.
In embodiments of the use, the composition comprises:
1.0 mg/mL of Compound 12;
50 mM citric acid monohydrate;
sodium hydroxide solution; and
water.
In embodiments of the use, the composition comprises:
Compound 13;
citric acid monohydrate;
sodium hydroxide solution; and
water.
In embodiments of the use, the composition comprises:
0.1 mg/mL of Compound 13;
50 mM citric acid monohydrate;
sodium hydroxide solution; and
water.

In embodiments of the use, the composition comprises:
1.0 mg/mL of Compound 13;
50 mM citric acid monohydrate;
sodium hydroxide solution; and
water.
In embodiments of the use, the composition comprises:
Compound 14;
citric acid monohydrate;
sodium hydroxide solution; and
water.
In embodiments of the use, the composition comprises:
0.1 mg/mL of Compound 14;
50 mM citric acid monohydrate;
sodium hydroxide solution; and
water.
In embodiments of the use, the composition comprises:
1.0 mg/mL of Compound 14;
50 mM citric acid monohydrate;
sodium hydroxide solution; and
water.
In embodiments of the use, the composition comprises:
Compound 15;
citric acid monohydrate;
sodium hydroxide solution; and
water.
In embodiments of the use, the composition comprises:
0.1 mg/mL of Compound 15;
50 mM citric acid monohydrate;
sodium hydroxide solution; and
water.
In embodiments of the use, the composition comprises:
1.0 mg/mL of Compound 15;
50 mM citric acid monohydrate;
sodium hydroxide solution; and
water.
In embodiments of the use, the composition comprises:
Compound 16;
citric acid monohydrate;
sodium hydroxide solution; and
water.
In embodiments of the use, the composition comprises:
0.1 mg/mL of Compound 16;
50 mM citric acid monohydrate;
sodium hydroxide solution; and
water.
In embodiments of the use, the composition comprises:
1.0 mg/mL of Compound 16;
50 mM citric acid monohydrate;
sodium hydroxide solution; and
water.
In embodiments of the use, the composition comprises:
Compound 17;
citric acid monohydrate;
sodium hydroxide solution; and
water.
In embodiments of the use, the composition comprises:
0.1 mg/mL of Compound 17;
50 mM citric acid monohydrate;
sodium hydroxide solution; and
water.
In embodiments of the use, the composition comprises:
1.0 mg/mL of Compound 17;
50 mM citric acid monohydrate;
sodium hydroxide solution; and
water.
In embodiments of the use, the composition comprises:
Compound 18;
citric acid monohydrate;
sodium hydroxide solution; and
water.
In embodiments of the use, the composition comprises:
0.1 mg/mL of Compound 18;
50 mM citric acid monohydrate;
sodium hydroxide solution; and
water.
In embodiments of the use, the composition comprises:
1.0 mg/mL of Compound 18;
50 mM citric acid monohydrate;
sodium hydroxide solution; and
water.
In embodiments of the use, the composition comprises:
Compound 19;
citric acid monohydrate;
sodium hydroxide solution; and
water.
In embodiments of the use, the composition comprises:
0.1 mg/mL of Compound 19;
50 mM citric acid monohydrate;
sodium hydroxide solution; and
water.
In embodiments of the use, the composition comprises:
1.0 mg/mL of Compound 19;
50 mM citric acid monohydrate;
sodium hydroxide solution; and
water.
In embodiments of the use, the composition comprises:
Compound 20;
citric acid monohydrate;
sodium hydroxide solution; and
water.
In embodiments of the use, the composition comprises:
0.1 mg/mL of Compound 20;
50 mM citric acid monohydrate;
sodium hydroxide solution; and
water.
In embodiments of the use, the composition comprises:
1.0 mg/mL of Compound 20;
50 mM citric acid monohydrate;
sodium hydroxide solution; and
water.
In embodiments of the use, the composition comprises:
Compound 21;
citric acid monohydrate;
sodium hydroxide solution; and
water.
In embodiments of the use, the composition comprises:
0.1 mg/mL of Compound 21;
50 mM citric acid monohydrate;
sodium hydroxide solution; and
water.
In embodiments of the use, the composition comprises:
1.0 mg/mL of Compound 21;
50 mM citric acid monohydrate;
sodium hydroxide solution; and
water.
In embodiments of the use, the composition comprises:
Compound 22;
citric acid monohydrate;
sodium hydroxide solution; and
water.

In embodiments of the use, the composition comprises:
0.1 mg/mL of Compound 22;
50 mM citric acid monohydrate;
sodium hydroxide solution; and
water.
In embodiments of the use, the composition comprises:
1.0 mg/mL of Compound 22;
50 mM citric acid monohydrate;
sodium hydroxide solution; and
water.
In embodiments of the use, the composition comprises:
Compound 23;
citric acid monohydrate;
sodium hydroxide solution; and
water.
In embodiments of the use, the composition comprises:
0.1 mg/mL of Compound 23;
50 mM citric acid monohydrate;
sodium hydroxide solution; and
water.
In embodiments of the use, the composition comprises:
1.0 mg/mL of Compound 23;
50 mM citric acid monohydrate;
sodium hydroxide solution; and
water.
In embodiments of the use, the composition comprises:
Compound 24;
citric acid monohydrate;
sodium hydroxide solution; and
water.
In embodiments of the use, the composition comprises:
0.1 mg/mL of Compound 24;
50 mM citric acid monohydrate;
sodium hydroxide solution; and
water.
In embodiments of the use, the composition comprises:
1.0 mg/mL of Compound 24;
50 mM citric acid monohydrate;
sodium hydroxide solution; and
water.
In embodiments of the use, the composition comprises:
Compound 25;
citric acid monohydrate;
sodium hydroxide solution; and
water.
In embodiments of the use, the composition comprises:
0.1 mg/mL of Compound 25;
50 mM citric acid monohydrate;
sodium hydroxide solution; and
water.
In embodiments of the use, the composition comprises:
1.0 mg/mL of Compound 25;
50 mM citric acid monohydrate;
sodium hydroxide solution; and
water.
In embodiments of the use, the composition comprises:
Compound 26;
citric acid monohydrate;
sodium hydroxide solution; and
water.
In embodiments of the use, the composition comprises:
0.1 mg/mL of Compound 26;
50 mM citric acid monohydrate;
sodium hydroxide solution; and
water.
In embodiments of the use, the composition comprises:
1.0 mg/mL of Compound 26;
50 mM citric acid monohydrate;
sodium hydroxide solution; and
water.
In embodiments of the use, the composition comprises:
Compound 27;
citric acid monohydrate;
sodium hydroxide solution; and
water.
In embodiments of the use, the composition comprises:
0.1 mg/mL of Compound 27;
50 mM citric acid monohydrate;
sodium hydroxide solution; and
water.
In embodiments of the use, the composition comprises:
1.0 mg/mL of Compound 27;
50 mM citric acid monohydrate;
sodium hydroxide solution; and
water.
In embodiments of the use, the composition comprises:
Compound 28;
citric acid monohydrate;
sodium hydroxide solution; and
water.
In embodiments of the use, the composition comprises:
0.1 mg/mL of Compound 28;
50 mM citric acid monohydrate;
sodium hydroxide solution; and
water.
In embodiments of the use, the composition comprises:
1.0 mg/mL of Compound 28;
50 mM citric acid monohydrate;
sodium hydroxide solution; and
water.
In embodiments of the use, the composition comprises:
Compound 29;
citric acid monohydrate;
sodium hydroxide solution; and
water.
In embodiments of the use, the composition comprises:
0.1 mg/mL of Compound 29;
50 mM citric acid monohydrate;
sodium hydroxide solution; and
water.
In embodiments of the use, the composition comprises:
1.0 mg/mL of Compound 29;
50 mM citric acid monohydrate;
sodium hydroxide solution; and
water.
In embodiments of the use, the composition comprises:
Compound 30;
citric acid monohydrate;
sodium hydroxide solution; and
water.
In embodiments of the use, the composition comprises:
0.1 mg/mL of Compound 30;
50 mM citric acid monohydrate;
sodium hydroxide solution; and
water.
In embodiments of the use, the composition comprises:
1.0 mg/mL of Compound 30;
50 mM citric acid monohydrate;
sodium hydroxide solution; and
water.

In embodiments of the use, the composition comprises:
Compound 31;
citric acid monohydrate;
sodium hydroxide solution; and
water.
In embodiments of the use, the composition comprises:
0.1 mg/mL of Compound 31;
50 mM citric acid monohydrate;
sodium hydroxide solution; and
water.
In embodiments of the use, the composition comprises:
1.0 mg/mL of Compound 31;
50 mM citric acid monohydrate;
sodium hydroxide solution; and
water.
In embodiments of the use, the composition comprises:
Compound 32;
citric acid monohydrate;
sodium hydroxide solution; and
water.
In embodiments of the use, the composition comprises:
0.1 mg/mL of Compound 32;
50 mM citric acid monohydrate;
sodium hydroxide solution; and
water.
In embodiments of the use, the composition comprises:
1.0 mg/mL of Compound 32;
50 mM citric acid monohydrate;
sodium hydroxide solution; and
water.
In embodiments of the use, the composition comprises:
Compound 33;
citric acid monohydrate;
sodium hydroxide solution; and
water.
In embodiments of the use, the composition comprises:
0.1 mg/mL of Compound 33;
50 mM citric acid monohydrate;
sodium hydroxide solution; and
water.
In embodiments of the use, the composition comprises:
1.0 mg/mL of Compound 33;
50 mM citric acid monohydrate;
sodium hydroxide solution; and
water.
In embodiments of the use, the composition comprises:
Compound 34;
citric acid monohydrate;
sodium hydroxide solution; and
water.
In embodiments of the use, the composition comprises:
0.1 mg/mL of Compound 34;
50 mM citric acid monohydrate;
sodium hydroxide solution; and
water.
In embodiments of the use, the composition comprises:
1.0 mg/mL of Compound 34;
50 mM citric acid monohydrate;
sodium hydroxide solution; and
water.
In embodiments of the use, the composition comprises:
Compound 35;
citric acid monohydrate;
sodium hydroxide solution; and
water.
In embodiments of the use, the composition comprises:
0.1 mg/mL of Compound 35;
50 mM citric acid monohydrate;
sodium hydroxide solution; and
water.
In embodiments of the use, the composition comprises:
1.0 mg/mL of Compound 35;
50 mM citric acid monohydrate;
sodium hydroxide solution; and
water.
In embodiments of the use, the composition comprises:
Compound 36;
citric acid monohydrate;
sodium hydroxide solution; and
water.
In embodiments of the use, the composition comprises:
0.1 mg/mL of Compound 36;
50 mM citric acid monohydrate;
sodium hydroxide solution; and
water.
In embodiments of the use, the composition comprises:
1.0 mg/mL of Compound 36;
50 mM citric acid monohydrate;
sodium hydroxide solution; and
water.
In embodiments of the use, the composition comprises:
Compound 37;
citric acid monohydrate;
sodium hydroxide solution; and
water.
In embodiments of the use, the composition comprises:
0.1 mg/mL of Compound 37;
50 mM citric acid monohydrate;
sodium hydroxide solution; and
water.
In embodiments of the use, the composition comprises:
1.0 mg/mL of Compound 37;
50 mM citric acid monohydrate;
sodium hydroxide solution; and
water.
In embodiments of the use, the composition comprises:
Compound 38;
citric acid monohydrate;
sodium hydroxide solution; and
water.
In embodiments of the use, the composition comprises:
0.1 mg/mL of Compound 38;
50 mM citric acid monohydrate;
sodium hydroxide solution; and
water.
In embodiments of the use, the composition comprises:
1.0 mg/mL of Compound 38;
50 mM citric acid monohydrate;
sodium hydroxide solution; and
water.
In embodiments of the use, the composition comprises:
Compound 39;
citric acid monohydrate;
sodium hydroxide solution; and
water.
In embodiments of the use, the composition comprises:
0.1 mg/mL of Compound 39;
50 mM citric acid monohydrate;
sodium hydroxide solution; and
water.

In embodiments of the use, the composition comprises:
1.0 mg/mL of Compound 39;
50 mM citric acid monohydrate;
sodium hydroxide solution; and
water.

In embodiments of the use, the composition comprises:
Compound 40;
citric acid monohydrate;
sodium hydroxide solution; and
water.

In embodiments of the use, the composition comprises:
0.1 mg/mL of Compound 40;
50 mM citric acid monohydrate;
sodium hydroxide solution; and
water.

In embodiments of the use, the composition comprises:
1.0 mg/mL of Compound 40;
50 mM citric acid monohydrate;
sodium hydroxide solution; and
water.

In embodiments of the use, the composition comprises:
Compound 41;
citric acid monohydrate;
sodium hydroxide solution; and
water.

In embodiments of the use, the composition comprises:
0.1 mg/mL of Compound 41;
50 mM citric acid monohydrate;
sodium hydroxide solution; and
water.

In embodiments of the use, the composition comprises:
1.0 mg/mL of Compound 41;
50 mM citric acid monohydrate;
sodium hydroxide solution; and
water.

In embodiments of the use, the composition comprises:
Compound 42;
citric acid monohydrate;
sodium hydroxide solution; and
water.

In embodiments of the use, the composition comprises:
0.1 mg/mL of Compound 42;
50 mM citric acid monohydrate;
sodium hydroxide solution; and
water.

In embodiments of the use, the composition comprises:
1.0 mg/mL of Compound 42;
50 mM citric acid monohydrate;
sodium hydroxide solution; and
water.

In embodiments of the use, the composition comprises:
Compound 43;
citric acid monohydrate;
sodium hydroxide solution; and
water.

In embodiments of the use, the composition comprises:
0.1 mg/mL of Compound 43;
50 mM citric acid monohydrate;
sodium hydroxide solution; and
water.

In embodiments of the use, the composition comprises:
1.0 mg/mL of Compound 43;
50 mM citric acid monohydrate;
sodium hydroxide solution; and
water.

In embodiments of the use, the composition comprises:
Compound 44;
citric acid monohydrate;
sodium hydroxide solution; and
water.

In embodiments of the use, the composition comprises:
0.1 mg/mL of Compound 44;
50 mM citric acid monohydrate;
sodium hydroxide solution; and
water.

In embodiments of the use, the composition comprises:
1.0 mg/mL of Compound 44;
50 mM citric acid monohydrate;
sodium hydroxide solution; and
water.

In embodiments of the use, the composition comprises:
Compound 45;
citric acid monohydrate;
sodium hydroxide solution; and
water.

In embodiments of the use, the composition comprises:
0.1 mg/mL of Compound 45;
50 mM citric acid monohydrate;
sodium hydroxide solution; and
water.

In embodiments of the use, the composition comprises:
1.0 mg/mL of Compound 45;
50 mM citric acid monohydrate;
sodium hydroxide solution; and
water.

In an aspect, the pharmaceutical compositions are used for reducing the viral load associated with an HBV infection in a subject in need thereof, comprising administering to the subject a therapeutically effective amount of the compositions described above.

In an aspect, the pharmaceutical compositions are used for reducing reoccurrence of an HBV infection in a subject in need thereof, comprising administering to the subject a therapeutically effective amount of the compositions described above.

In an aspect, the pharmaceutical compositions are used for reducing an adverse physiological impact of an HBV infection in a subject in need thereof, comprising administering to the subject a therapeutically effective amount of the compositions described above.

In an aspect, the pharmaceutical compositions are used for inducing remission of hepatic injury from an HBV infection in a subject in need thereof, comprising administering to the subject a therapeutically effective amount of the compositions described above.

In an aspect, the pharmaceutical compositions are used for treating a latent HBV infection in a subject in need thereof, comprising administering to the subject a therapeutically effective amount of the compositions described above.

In embodiments, the use further comprises administering to the subject at least one additional therapeutic agent selected from the group consisting of HBV polymerase inhibitors, nucleic acid analogs, interferons, viral entry inhibitors, viral maturation inhibitors, capsid assembly modulators, reverse transcriptase inhibitors, TLR-agonists, small interfering RNAs, antisense oligonucleotides, nucleic acid polymers and a combination thereof.

The following examples are merely illustrative and are not intended to limit the disclosure to the materials, conditions, or process parameters set forth therein.

EXAMPLES

Example 1: Formulations of Compound 4

The quantitative and qualitative composition of the Compound 4, 0.1 mg/mL oral solution is provided in Table 1 below.

TABLE 1

Quantitative and Qualitative Composition of the Compound 4, 0.1 mg/mL oral solution

| Component | Quality Reference | Function | Quantity |
|---|---|---|---|
| Compound 4 | In-house | Active | 0.1 mg/mL |
| Citric Acid Monohydrate | PhEur, USP, JP | Buffer | 50 mM |
| Sodium Hydroxide Solution | PhEur, USP, JP | pH Adjustment | As required[a] |
| Water | PhEur, USP, JP | Solubilizing Medium | QS to Volume |
| Volume per Bottle | | | 12 mL |

NF: National Formulary;
PhEur: European Pharmacopeia;
USP: United States Pharmacopeia;
JP: Japanese Pharmacopeia
mM: millimolar concentration
M: molar concentration
QS: quantum sufficit
[a]The actual quantity of sodium hydroxide solution is determined based on pH adjustment to the target range of pH 4-5 during manufacture by using a 2M stock solution of sodium hydroxide in water for injection and a calibrated pH probe.

The quantitative and qualitative composition of the Compound 4, 1.0 mg/mL oral solution is provided in Table 2 below.

TABLE 2

Quantitative and Qualitative Composition of the Compound 4, 1.0 mg/mL oral solution

| Component | Quality Reference | Function | Quantity |
|---|---|---|---|
| Compound 4 | In-house | Active | 1.0 mg/mL |
| Citric Acid Monohydrate | PhEur, USP, JP | Buffer | 50 mM |
| Sodium Hydroxide Solution | PhEur, USP, JP | pH Adjustment | As required[a] |
| Water | PhEur, USP, JP | Solubilizing Medium | QS to Volume |
| Volume per Bottle | | | 12 mL |

NF: National Formulary;
PhEur: European Pharmacopeia;
USP: United States Pharmacopeia;
JP: Japanese Pharmacopeia
mM: millimolar concentration
M: molar concentration
QS: quantum sufficit
[a]The actual quantity of sodium hydroxide solution is determined based on pH adjustment to the target range of pH 4-5 during manufacture by using a 2M stock solution of sodium hydroxide in water for injection and a calibrated pH probe.

The qualitative compositions of the Compound 4 and placebo tablets are provided in Table 3 and Table 4 below.

TABLE 3

Qualitative Composition of Compound 4 Tablets: 0.2 mg, 0.5 mg, 1.0 mg Strengths

| Component | Function |
|---|---|
| Compound 4 | Active |
| Silicified microcrystalline cellulose | Filler |
| Croscarmellose sodium | Disintegrant |
| Magnesium stearate | Lubricant |
| Opadry II White 85F18422[a] | Film coating system |

[a]Opadry ® II by Colorcon Inc., immediate release coating system contains USP/Ph.Eur polyvinyl alcohol, polyethylene glycol, titanium dioxide, and talc

TABLE 4

Qualitative Composition of Placebo Tablet to Match 0.2 mg, 0.5 mg, 1.0 mg Compound 4 Strengths

| Component | Function |
|---|---|
| Silicified microcrystalline cellulose | Filler |
| Croscarmellose sodium | Disintegrant |
| Magnesium stearate | Lubricant |
| Opadry II White 85F18422[a] | Film coating system |

[a]Opadry ® II by Colorcon Inc., immediate release coating system contains USP/Ph.Eur polyvinyl alcohol, polyethylene glycol, titanium dioxide, and talc Example 2: Phase 1, Double-Blind, Randomized, Placebo-Controlled, First-In-Human Study of the Safety, Tolerability, Pharmacokinetics and Pharmacodynamics of Oral Compound 4, a Toll-Like Receptor-7 Agonist, in Healthy Adults 1. Introduction Current treatments for chronic hepatitis B virus (HBV) infection rarely result in a functional cure hence life-long therapy is required for the majority of patients. Thus, novel, therapeutic approaches to improve current care by providing a finite treatment, resulting in a functional HBV cure, are required. Compound 4 is an oral toll-like receptor-7 agonist currently in clinical development to treat chronic HBV. Toll-like receptors (TLR) have a well-recognized role as the first line of antiviral immunity. Compound 4 is a potent and selective TLR-7 agonist in vitro, and induces antiviral (interferons [IFNs]), pro-inflammatory and anti-inflammatory cytokines and chemokines in human whole blood cells.3 In turn, IFNs induce expression of IFN-stimulated genes (ISGs). Known/expected safety profile for TLR7 agonists include transient flu-like symptoms and lymphocyte decrease. Compound 4 also has demonstrated potent anti-HBV activity and HBsAg seroconversion in preclinical studies. This first-in-human study (NCT03285620, AL-0134-1201) assessed the safety, tolerability, pharmacokinetics (PK) and pharmacodynamics (PD) of single- and multiple doses of Compound 4 in healthy adults with/without food. Results of the single-ascending dose (SAD) part of this study are presented herein.

Compound 4 is a butoxy-pyrrolopyrimidine amine; it is a white to slightly colored solid with molecular formula $C_{22}H_{29}N_5O$ and a molecular weight of 379.50 Dalton.

The drug products for Phase 1 clinical studies are supplied as oral solutions filled in amber glass bottles with a screw cap closure. Two concentrations of Compound 4 solution drug products are available including 0.1 mg/mL and 1.0 mg/mL concentrations, and one common placebo to match. For long-term storage, the drug product bottles should be stored at frozen conditions.

The tablet drug products for Phase 1 and 2 clinical studies were supplied in 3 strengths of Compound 4 active: 0.2 mg, 0.5 mg, and 1.0 mg.

Nonclinical Pharmacology

Compound 4 activated human TLR7 at lowest effective concentration (LEC)=70 nM and monkey TLR7 at LEC<119 nM.

The overall LEC for Compound 4-induced cytokine release in vitro was determined to be 2 nM.

Compound 4 at a dose of 20 mg/kg showed potent anti-HBV activity in vivo in AAV/HBV mice with undetectable hepatitis B surface antigen (HBsAg) serum levels and HBsAg seroconversion in all animals. Post-treatment reductions in HBsAg levels were sustained up to 3 weeks whereas anti-HBsAg antibodies gradually decreased.

Single oral administration (0.05, 0.1, 0.15, and 0.6 mg/kg) of Compound 4 in monkeys was well tolerated and an increase in all 3 major interferon-stimulated genes (ISGs) (ISG15, MX1, and OAS1) was observed for each dose in peripheral blood between 12 and 24 hours postdose. At the highest dose of 0.6 mg/kg, an induction of 4 of the 14 cytokines tested was observed: IFN-α, IP-10, IL-1 RA, and MCP-1. At doses of 0.1 and 0.15 mg/kg, only increases in IP-10 were detected. Maximum cytokine levels were observed between 8 and 24 hours postdose and all cytokines returned to predose levels within 24 and 72 hours.

A positive non-linear relationship between the maximal absolute levels of IFN-α, IP-10, and all 3 ISGs and the maximum exposure of Compound 4 in monkey peripheral blood was observed.

0.1 mg/kg: dose for which the LEC was observed showing minimal target engagement of Compound 4 in monkeys, i.e., induction of ISG expression with minimal induction of systemic cytokines.

Expression of ISGs in the monkey liver showed a similar expression pattern as in peripheral blood.

Pharmacokinetics and Metabolism in Animals

Absorption after oral dosing was fast ($t_{max}$=0.8-2 hours) with low oral bioavailability (15% in rat and 1.5% in monkey). Exposure increased more than dose-proportionally at low doses. Variability in exposure was high.

In vitro plasma protein binding was between 79.6% and 94.2% in animals and humans. Volume of distribution after intravenous dosing was high. Compound 4 extensively distributed in tissues after oral dosing in rats and monkeys with highest levels in liver, small intestines and brain.

Blood clearance was moderate and elimination was slow ($t_{1/2}$=5-14 hours). Main metabolic pathways were oxygenation, hydrogenation, dehydrogenation, dealkylation, acetylation, glucuronidation, and/or glutathione conjugation.

In rats, >80% of drug-related material was found in feces, 11% to 20% in bile, and <4% in urine. Elimination occurred mainly via metabolism.

Compound 4 has low in vitro permeability and is a P-glycoprotein substrate. Compound 4 is a substrate and moderate to strong inhibitor of CYP3A4 ($IC_{50}$=0.59 µM). Compound 4 is not an in vitro inducer of CYP1A2, 2B6, and 3A4 (up to 10 µM). Compound 4 is an organic ion transporter 2 (OCT2) inhibitor in vitro ($IC_{50}$=4.97 µM).

Toxicology

Compound 4 showed no relevant off-target liabilities in vitro (lowest $IC_{50} \geq 1.97$ µM).

Compound 4 is free of genotoxic potential.

A transient increase in heart rate and arterial blood pressure was observed in monkeys secondary to an increase in body temperature. Compound 4 had no relevant effects on respiratory or central nervous system parameters in rats.

The no-observed-adverse-effect-level (NOAEL) in the 6-month toxicity study in rats was 1.0 mg/kg qw or q2w ($C_{max}$=3.32-7.88 ng/mL; $AUC_{24h}$=16.6-27.3 ng·h/mL). The NOAEL in the 6-month toxicity study in Cynomolgus monkeys was 3.0 mg/kg qw or 4.5 mg/kg q2w ($C_{max}$=2.56-16.4 ng/mL; $AUC_{24h}$=13.2-44.8 ng·h/mL). Clinical pathology and histopathology findings were related to anticipated and exaggerated immunostimulation.

Brain inflammation occurred at high doses and exposure levels in a 14-week rat study (5 mg/kg biw) and a 14- and 28-day study in monkeys (3, 15, and 100 mg/kg biw).

Post-implantation loss and fetal weights effects were noted in pregnant rats at 3 mg/kg biw. There were no effects on embryofetal development up to 1 mg/kg/dose in rats and 30 mg/kg/dose in rabbits.

2. Study Design

This ongoing trial is a Phase 1 randomized, double-blind, placebo-controlled study in male and female healthy adult volunteers aged 18-55 years. All volunteers provided written, informed consent. For the SAD phase, 8-10 volunteers per cohort were randomized 6-8:2 to receive a single oral dose of either Compound 4 0.2 (N=6), 0.6 (N=6), 1.25 (N=8) or 1.8 mg (N=6) or placebo (N=2/dose group) under fasted conditions; following an ~6-week washout period, the cohort subjects which had received 1.25 mg under fasted conditions in Cohort 4 were given the same 1.25 mg dose (N=7) under fed conditions (a standard meal consumed before dosing), in Cohort 6 (FIG. 1). Escalation of the Compound 4 dose was only permitted following a review of the safety and PK data from the previous cohort.

3. Safety Assessments

All volunteers were followed up for 4 weeks and safety and tolerability were continuously assessed throughout the study. All adverse events (AEs) were recorded from the time of consent to the completion visit and were graded using the DAIDS toxicity grading scale. Volunteers also underwent physical examinations, electrocardiograms, vital sign checks and clinical laboratory parameters (chemistry, haematology, urinalysis).

4. Pharmacokinetic Assessments

Following a single dose of Compound 4, intensive blood samples were collected over the first 24 hours, samples were then collected daily through Day 7, and weekly samples were collected through Day 35. Plasma concentrations of Compound 4 were evaluated using a validated liquid chromatography with tandem mass spectrometry method; the lower limit of quantification was 1 pg/mL. PK parameters were estimated using non-compartmental analysis (WinNonlin®, Certara, Princeton, NJ, USA). Descriptive statistics were used to summarize plasma concentrations and derived PK parameters of Compound 4. The impact of food on PK parameters was analyzed using geometric least square mean point estimates (mixed-effects model on log-transformed values with treatment as fixed effect and subject as a random effect).

5. Pharmacodynamic Assessments

Serum samples were collected at baseline and post-dosing on Days 1 (1.5, 6 and 12 h post-dosing), 2, 3, 5 and at follow-up, Day 14 week 2. IFN-α was assessed by an enzyme-linked immunosorbent assay; 13 other cytokines (granulocyte colony stimulating factor [GCSF], granulocyte macrophage colony stimulating factor [GMCSF], IFN-γ, IFN-γ-induced protein 10 [IP-10], interleukin [IL] 1β, IL-1 receptor antagonist [IL-1 RA], IL-10, IL-12 subunit P40, IL-6, IL-8, macrophage inflammatory protein 1β [MIP-1β], monocyte chemotactic protein 1 [MCP-1], and tumour necrosis factor [TNF]) were analysed by the appropriate Luminex assays. ISG expression analysis was conducted for three genes, ISG15, MX1 and OAS1 using quantitative polymerase chain reaction. Descriptive statistics were used to summarise PD parameters over time, and relative fold-changes from baseline values were calculated.

6. Volunteers

Eighty-seven volunteers were screened, and 34 met the eligibility criteria for the study and were randomized. Single oral dosing of Compound 4 has been completed for all randomized healthy volunteers, and baseline demographics are listed in Table 5.

Single Dose

The majority of subjects in Part 1 were male (30 [88.2%] subjects) and had a mean age of 31.4 years, ranging from 20 to 55 years old. Mean age was similar across cohorts. The mean BMI was 24.38 kg/m$^2$ (range: 18.6 to 29.3 kg/m$^2$) and was equally distributed. Most of the subjects were White (21 [61.8%] subjects), 7 (20.6%) subjects were Asian, 4 (11.8%) subjects were native Hawaiian (or other Pacific Islander), 1 (2.9%) subject was Black or African American and 1 (2.9%) subject was from mixed descent.

Note that the subjects evaluated for food effect in Cohorts 4 and 6 were enriched for females by the site to include the minimum of 3 female subjects.

Multiple Dose

Most subjects were male (7 [87.5%] subjects) and had a mean age of 31.9 years, with range between 20 and 54 years old. The mean BMI was 25.60 kg/m$^2$ (range: 18.9 to 29.9 kg/m$^2$). Six (75.0%) subjects were White, whereas 1 (12.5%) subject was native Hawaiian (or other Pacific Islander) and 1 (12.5%) subject was Asian.

TABLE 5

Baseline Demographics

| | Compound 4 SAD | | | | | |
|---|---|---|---|---|---|---|
| | 0.2 mg fasted N = 6 | 0.6 mg fasted N = 6 | 1.25 mg fasted* N = 8 | 1.25 mg fed* N = 7 | 1.8 mg fasted N = 6 | All placebo N = 8 |
| Age, years; median (range) | 23.5 (20-48) | 25.5 (21-31) | 33.0 (23-55) | 34.0 (29-55) | 30.5 (25-48) | 28.5 (21-44) |
| Male, n (%) | 6 (100) | 6 (100) | 5 (63) | 4 (57) | 5 (83) | 8 (100) |
| Race, n (%) | | | | | | |
| White | 3 (50) | 4 (67) | 3 (38) | 2 (29) | 5 (83) | 6 (75) |
| Native Hawaiian/other | 0 | 0 | 3 (38) | 3 (43) | 0 | 1 (13) |
| Asian | 2 (33) | 2 (33) | 2 (25) | 2 (29) | 1 (17) | 0 |
| Black/AA | 0 | 0 | 0 | 0 | 0 | 1 (13) |
| Multiple | 1 (17) | 0 | 0 | 0 | 0 | 0 |
| BMI, kg/m$^2$; median (range) | 22.9 (19-28) | 24.0 (23-26) | 23.4 (22-29) | 23.4 (22-29) | 25.2 (21-28) | 25.7 (21-29) |
| Weight, kg; median (range) | 75.6 (58-92) | 76.0 (68-86) | 73.5 (64-78) | 72.3 (64-77) | 73.0 (62-88) | 77.4 (65-101) |

*Volunteers who received 1.25 mg Compound 4 under fasted conditions then received the same dose under fed conditions after an ~6-week washout period (one of the subjects randomized to receive Compound 4 under fasted conditions dropped out of the study for personal reasons prior to receiving the 2$^{nd}$ dose of Compound 4 under fed conditions)

AA: African American;

BMI: body mass index;

SAD: single-ascending dose

7. Compound 4 Safety

All tested single doses of Compound 4 were well tolerated with no major safety concerns. There were no serious AEs or dose-limiting toxicities. One volunteer (1.25 mg fasted cohort) had Grade 2 seasonal allergy, which was considered not related to Compound 4 by the investigator, and the subject decided to discontinue their participation in the study. All AEs were mild (Grade 1) or moderate (Grade 2) in severity. The most common treatment-emergent AEs in all cohorts (≥2 volunteers) were headache, oropharyngeal pain, and contact dermatitis (Table 6). 10/34 volunteers reported mild (≤Grade 2), transient and reversible AEs at least possibly related to study drug: 5 (n=3, 1.25 mg fasted; n=2, 1.8 mg fasted) had fever and flu-like symptoms that resolved within 24-48 hours. Treatment-related Grade 2 AEs were noted in the following two treatment groups: 1.25 mg (fasted): one volunteer with pyrexia; 1.8 mg (fasted): two volunteers (n=1: pyrexia and headache; n=1: hypertension). Most laboratory abnormalities were Grade 1 in severity; Table 7 lists those values that were ≥Grade 2 in severity. No clinically significant changes in physical examination, vital signs or electrocardiograms were observed.

TABLE 6

Summary of Treatment-emergent AEs Following Administration of Compound 4.

| | n (%) | | | | | |
|---|---|---|---|---|---|---|
| | Compound 4 SAD | | | | | |
| | 0.2 mg fasted N = 6 | 0.6 mg fasted N = 6 | 1.25 mg fasted* N = 8 | 1.25 mg fed* N = 7 | 1.8 mg fasted N = 6 | All placebo N = 8 |
| Any AE | 4 (67) | 3 (50) | 8 (100) | 6 (86) | 5 (83) | 3 (38) |
| Most common AEs (n ≥ 2 in any one group) | | | | | | |
| Headache | | | | | | |
| Grade 1 | 1 (17) | 0 | 4 (50) | 1 (14) | 0 | 1 (13) |
| Grade 2 | 0 | 0 | 0 | 0 | 1 (17) | 0 |
| Oropharyngeal pain | | | | | | |
| Grade 1 | 0 | 1 (17) | 2 (25) | 2 (29) | 1 (17) | 0 |
| Contact dermatitis | | | | | | |
| Grade 1 | 2 (33) | 0 | 0 | 0 | 3 (50) | 1 (13) |
| URTI | | | | | | |
| Grade 1 | 0 | 0 | 2 (25) | 1 (14) | 1 (17) | 2 (25) |
| Pyrexia | | | | | | |
| Grade 1 | 0 | 0 | 2 (25) | 0 | 1 (17) | 0 |
| Grade 2 | 0 | 0 | 1 (13) | 0 | 1 (17) | 0 |
| Myalgia | | | | | | |
| Grade 1 | 0 | 0 | 3 (38) | 0 | 1 (17) | 0 |
| Back pain | | | | | | |
| Grade 1 | 0 | 0 | 1 (13) | 0 | 2 (33) | 0 |
| Dizziness | | | | | | |
| Grade 1 | 1 (17) | 0 | 0 | 0 | 2 (33) | 0 |
| Chills | | | | | | |
| Grade 1 | 0 | 0 | 0 | 0 | 2 (33) | 0 |
| Hypertension | | | | | | |
| Grade 1 | 0 | 0 | 0 | 0 | 1 (17) | 0 |
| Grade 2 | 0 | 0 | 0 | 0 | 1 (17) | 0 |

*Volunteers receiving 1.25 mg Compound 4 under fasted conditions then received the same dose under fed conditions after an ~6-week washout period AE: adverse event;

SAD: single-ascending dose;

URTI: upper respiratory tract infection

TABLE 7

Incidence of Grade ≥2 Treatment-emergent Laboratory Abnormalities Following Administration of Compound 4.

| | n (%) | | | | | |
|---|---|---|---|---|---|---|
| | Compound 4 SAD | | | | | |
| | 0.2 mg fasted N = 6 | 0.6 mg fasted N = 6 | 1.25 mg fasted* N = 8 | 1.25 mg fed* N = 7 | 1.8 mg fasted N = 6 | All placebo N = 8 |
| ↑ Amylase | | | | | | |
| Grade 2 | 1 (17) | 0 | 0 | 0 | 0 | 1 (13) |
| ↑ Pancreatic amylase | | | | | | |
| Grade 2 | 0 | 0 | 0 | 0 | 1/2 (50) | 0 |
| ↑ AST | | | | | | |
| Grade 3 | 0 | 0 | 0 | 0 | 0 | 1 (13) |
| ↓ Bicarbonate | | | | | | |
| Grade 2 | 1 (17) | 0 | 0 | 0 | 1 (17) | 0 |
| ↑ Cholesterol | | | | | | |
| Grade 2 | 1 (17) | 0 | 1 (17) | 1 (14) | 1/5 (20) | 0 |
| ↑ Creatine kinase | | | | | | |
| Grade 2 | 0 | 1 (17) | 0 | 0 | 1 (17) | 0 |
| Grade 4 | 0 | 0 | 0 | 0 | 0 | 1 (13 |
| ↓ GFR | | | | | | |
| Grade 2 | 0 | 0 | 6/7 (86) | 0 | 0 | 0 |
| ↑ Glucose | | | | | | |
| Grade 2 | 0 | 1 (17) | 1 (13) | 0 | 0 | 0 |
| ↑ LDL cholesterol | | | | | | |
| Grade 2 | 1 (17) | 1 (17) | 0 | 1 (14) | 0 | 0 |
| Grade 3 | 0 | 0 | 1 (13) | 0 | 0 | 0 |
| ↑ Lipase | | | | | | |
| Grade 2 | 0 | 0 | 0 | 0 | 1/5 (20) | 0 |
| ↓ Phosphate | | | | | | |
| Grade 2 | 0 | 0 | 0 | 1 (14) | 0 | 0 |
| ↑ Sodium | | | | | | |
| Grade 2 | 0 | 1 (17) | 1 (13) | 0 | 1 (17) | 1 (13) |
| ↑ Triglycerides | | | | | | |
| Grade 2 | 2 (33) | 0 | 4 (50) | 1 (14) | 0 | 1 (13) |
| Grade 3 | 0 | 0 | 0 | 0 | 1 (17) | 0 |
| ↓ Lymphocytes | | | | | | |
| Grade 2 | 0 | 0 | 1 (13) | 0 | 0 | 0 |
| Grade 4 | 0 | 0 | 0 | 0 | 2 (33) | 0 |
| ↓ Neutrophils | | | | | | |
| Grade 2 | 0 | 0 | 0 | 0 | 1 (17) | 0 |
| ↑ Potassium | | | | | | |
| Grade 2 | 0 | 0 | 0 | 0 | 1/5 (20) | 0 |

Denominator shows number of volunteers with data; ↓ = decrease; ↑ = increase

*Volunteers receiving 1.25 mg Compound 4 under fasted conditions then received the same dose under fed conditions after an ~6-week washout period AST: aspartate aminotransferase;

GFR: glomerular filtration rate (from creatinine adjusted for body surface area);

LDL: low-density lipoprotein;

SAD: single-ascending dose

8. Single Oral Dose Pharmacokinetics of Compound 4

Following single oral doses from 0.2 to 1.8 mg in fasted conditions, exposure to Compound 4 increased in proportion with the dose (FIG. 2). Compound 4 uptake was rapid, with a $t_{max}$ ranging from 0.5 to 1 hours (Table 8), followed by a rapid distribution phase (FIG. 2), with a variable and long median $t_{1/2}$ term ranging from 126 to 868 hours (Table 8). The $AUC_{48h}$ for Compound 4 was ~17%, lower in the 1.25-mg fed state than in the fasted state; least square mean ratio point estimate (90% CI) for fed vs fasted states was 83.45 (90% CI 65.89-105.71), p=0.0297. The observed decrease in exposure in fed state may be blunted due to the current study design whereby the dose was administered ~6 weeks after the first dose in fasted state and the drug was not completely washed out (mean $C_{predose}$ 1.85 pg/mL).

TABLE 8

Summary of Compound 4 Pharmacokinetic Parameters

| Compound 4 Dose (mg)[a] | Predose Level[c] (pg/mL) | $C_{max}$ (pg/mL) | $t_{max}$ (h) | $AUC_{24\,h}$ (pg · h/mL) | CL/F (L/h)[d] | $t_{1/2term}$ (h)[e] |
|---|---|---|---|---|---|---|
| 0.2 | — | 34.4 ± 17.9 | 0.50 (0.50-0.50) | 190 ± 97.2 | 149 | 150 (126-212) |
| 0.6 | — | 109 ± 28.1 | 0.50 (0.50-1.00) | 594 ± 210 | 244 | 284 (104-479) |
| 1.8 | — | 309 ± 136 | 0.50 (0.50-1.00) | 1,369 ± 357 | — | 194 (185-205) |
| 1.25 | — | 143 ± 65.9 | 0.75 (0.50-1.00) | 815 ± 251 | 254 | 448 (372-502) |
| 1.25 (Fed) | 1.85 ± 0.597 | 152 ± 76.4 | 0.50 (0.50-1.50) | 659 ± 194 | — | 591 (448-868) |

[a] n = 6 for all doses except for 1.25 mg fasted (n = 8) and 1.25 mg fed (n = 7).
[b] Median (range) for $t_{max}$ and $t_{1/2term}$.
[c] 1.25 mg dose was administered in fed condition on average 41 days (or 984 hours) after first 1.25 mg dose that was administered under fasted condition.
[d] CL/F: n = 1 for 0.2 mg and 0.6 mg; n = 3 for 1.25 mg (fasted).
[e] $t_{1/2term}$: n = 3 for 0.2 mg, 0.6 mg and 1.8 mg; n = 5 for 1.25 mg (fasted and fed).

During the SAD dose phase the sampling time period was extended from 14 days post dosing up to 35 days post dosing in order to better characterize the elimination of the compound.

Terminal elimination was long (median range: 150 to 591 hours), however, the sampling schedule was not long enough to have it reliably estimated for most subjects.

Among the subjects with estimable total apparent oral clearance, the values were 149, 244, and 254 L/hour after a single oral dose of 0.2 mg, 0.6 mg, and 1.25 mg of Compound 4 under fasted condition, respectively.

After a single 1.25 mg dose administered in fasted condition less than 0.2% was excreted as unchanged drug in urine within the first 24 hours after dosing. Mean renal clearance was 2.57 L/hour (range 1.86-3.81 L/hour).

9. Multiple Dose Pharmacokinetics of Compound 4

Figure 3:
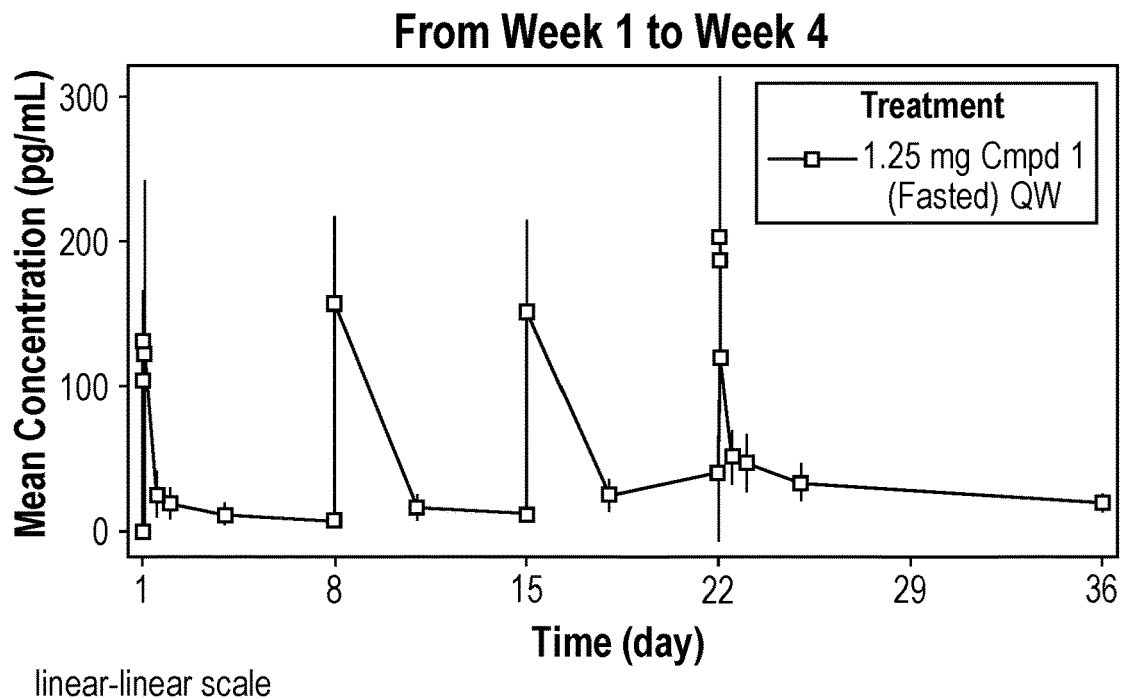
FIG. 3 depicts the mean plasma concentration-time profile of Compound 4 after qw dosing.

Compound 4 was administered every week for 4 weeks in fasted condition at a dose of 1.25 mg. Mean plasma concentration-time profile is presented in FIG. 3.

After repeated once weekly dosing in fasted condition $C_{trough}$ concentrations increased in all subjects with repeated dosing. Before the second dose, mean $C_{trough}$ was 7.17±3.2 pg/mL and increased to 40.8±48.9 pg/mL before the fourth dose.

Median $t_{max}$ was similar after single and multiple dose administrations. After the first dose, mean $C_{max}$ and $AUC_{24h}$ were 186 pg/mL (SD 88.4) and 1,209 pg·h/mL (SD 874) and increased to 235 pg/mL (SD 67.2) and 1,764 pg·h/mL (SD 591), respectively, after the fourth dose.

Accumulation was observed after 4 weeks of qw dosing, with mean accumulation ratios of 1.83, 2.27, and 2.75 for $AUC_{24h}$, $AUC_{72h}$, and $AUC_T$, respectively.

Terminal elimination was long (median value: 244 hours), however, the sampling schedule was not long enough to have it estimated reliably for most subjects.

Less than 0.22% of Compound 4 was excreted as unchanged drug in urine within the first 24 hours after the first and second dosing.

10. Food-Interaction

In a sequential design all subjects received 1.25 mg of Compound 4 in fasted condition and 1.25 mg in fed condition after a wash-out period of approximately 41 days. Predose levels of Compound 4 in fed condition were measurable in all subjects and ranged from 1.16 to 2.59 pg/mL.

Statistical comparison of fasted versus fed condition subjects suggested a similar $C_{max}$ but a lower exposure in fed condition. $AUC_{48h}$ was approximately 17% (95% CI: 65.89-105.71%) lower in fed condition compared with fasted. These differences are aligned with BCS Class 3 (high solubility, low permeability) compound properties.

11. Compound 4 Pharmacodynamics

Serum levels of IFN-α were measured by ELISA. Serum levels of IP-10, IFN-γ, TNF-α, IL-12 (subunit P40), IL-6, IL-1β, IL-1RA, IL-18, MCP-1, MIP-1β, G-CSF, GM-CSF, IL-10, IL-15 were measured by Luminex xMAP technology. The LLOQ for IFN-α was determined at 12.5 pg/mL and at 25 pg/mL for all other cytokines measured. Fold changes for each of the cytokines were calculated compared to predose values or LLOQ-1 values if predose values were below LLOQ.

IFN-stimulated gene (ISG) expression analysis was conducted for 3 genes, ISG15, MX1, and OAS1, using quantitative polymerase chain reaction (qPCR) on collected whole blood samples. For the ISGs, relative fold changes from baseline were calculated according to the delta delta Cycle threshold (Ct) method (2^[Delta Delta Ct]). Assessments were done for Part 1 predose and postdose: 1.5 hours, 6 hours, 12 hours (Day 1), 24 hours (day 2), 48 hours (Day 3), 96 hours (Day 5), follow-up Week 2. For the Part 2, assessments were done predose and post the first and fourth dose: 2 hours, 4 hours, 12 hours, 24 hours, 48 hours, 96 hours and one week follow-up; and post the second and third doses: 12 hours and 48 hours.

12. Pharmacodynamics Following Single Oral Dosing in Healthy Volunteers

No relevant induction of ISGs or cytokines was observed in the 0.2 mg Compound 4 treated group.

Figure 4:
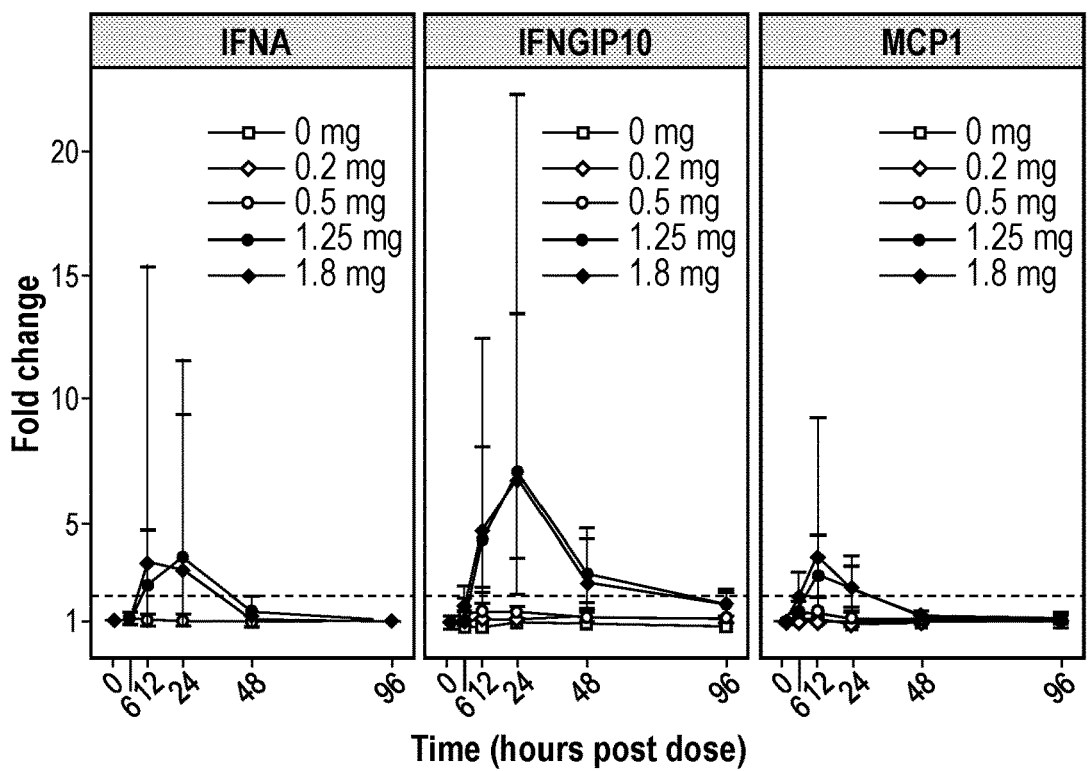
FIG. 4 depicts the Dose-dependent and Transient Increase (≥2-fold Change from Baseline) of IFNα, IP-10 and MCP-1 following Single Oral administration of Compound 4 in fasted conditions. N=6 per cohort; except for placebo (N=8, 0 mg), Compound 4 1.25 mg fasted (N=8) and 1.25 mg fed (N=7). IFN: interferon; IP-10: IFNα-induced protein 10; MCP: monocyte chemotactic protein.
Figure 5A:
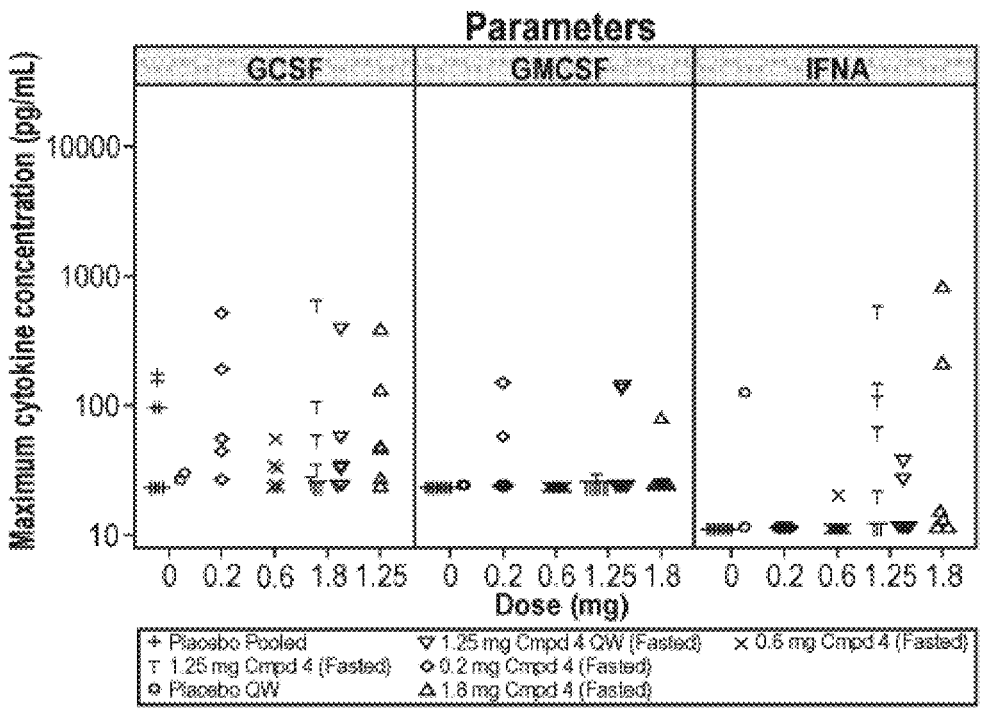
FIGS. 5A-5E depict pharmacodynamics of Compound 4 following single oral dosing in healthy volunteers. The maximum cytokine expression for the first 96 hours is shown in relation to dose of Compound 4. LLOQ IFN-α=12.5 pg/mL; LLOQ all other cytokines=25 pg/mL.
Figure 5B:
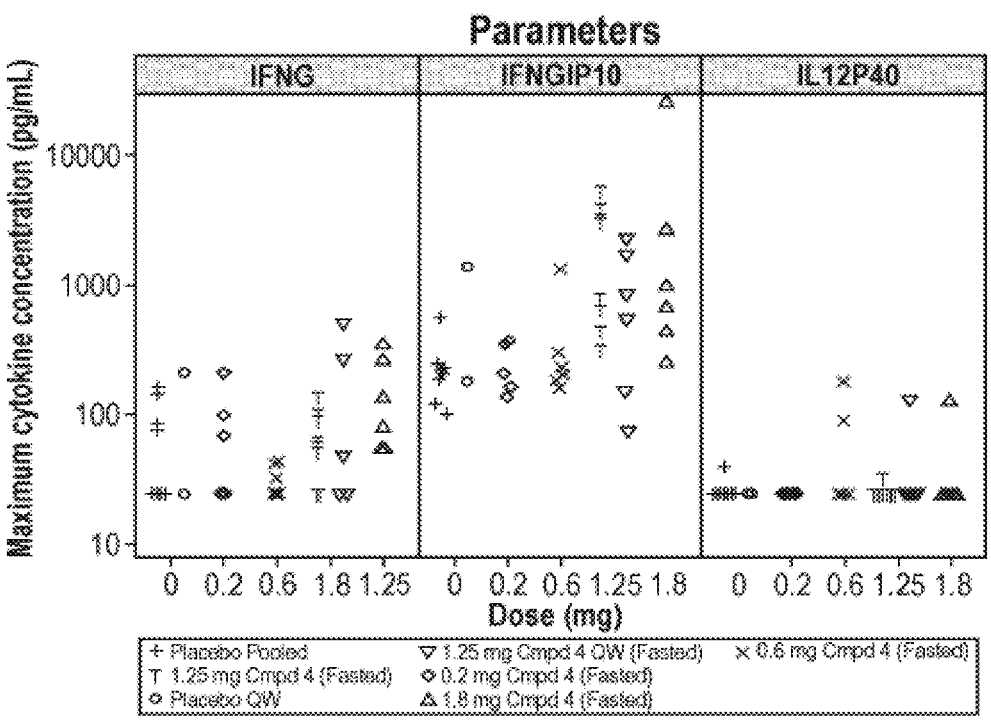
Figure 5C:
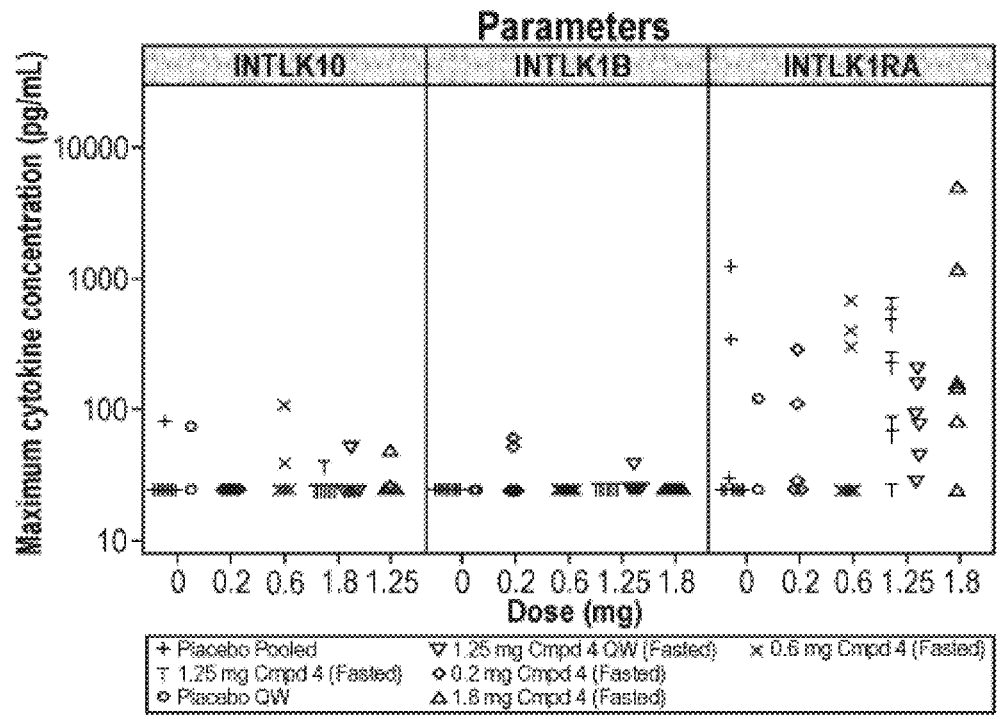
Figure 5D:
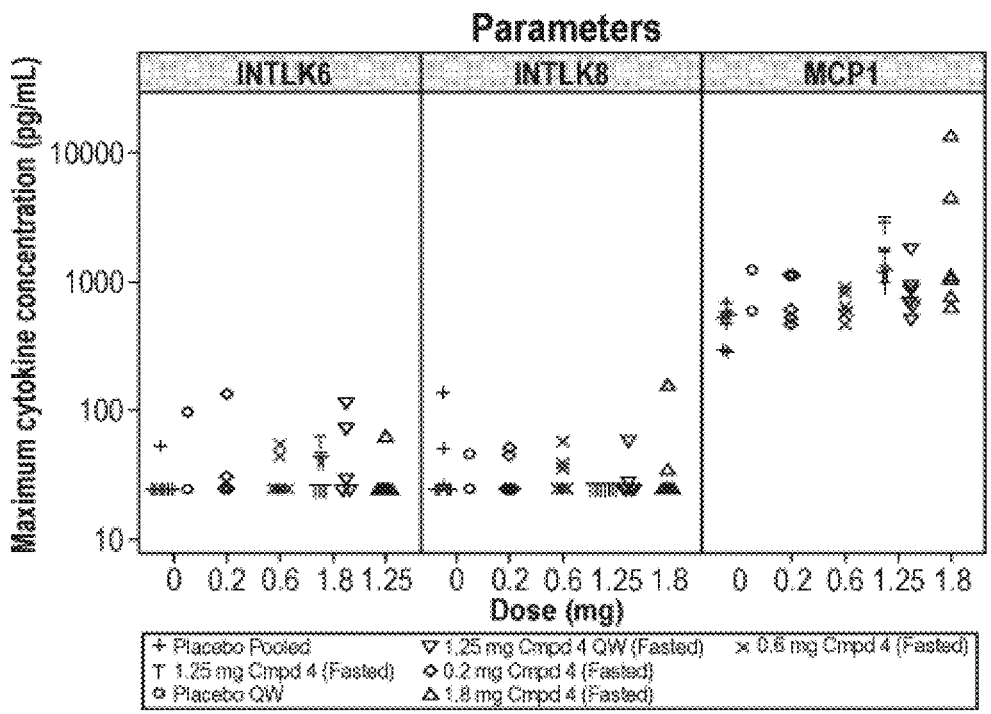
Figure 5E:
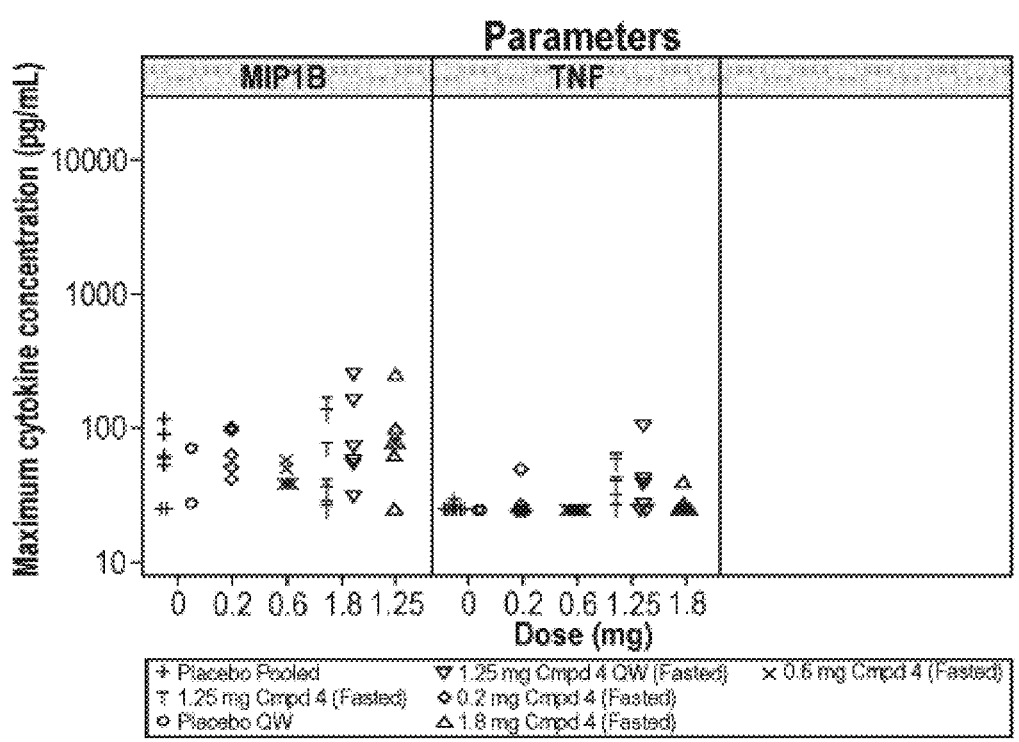

Induction of all three ISGs was observed in the 1.25 mg and 1.8 mg Compound 4 dose groups (Table 9). Of the 14 cytokines evaluated, 5 cytokines, IFN-α, IP-10, IL-1 RA, MCP-1, IL-6, increased ≥2-fold versus baseline levels following a single dose of Compound 4 but not with placebo (Table 9). Increased expression of IP-10, MCP-1 and/or IL-1 RA was observed in subjects in the 0.6, 1.25 and 1.8 mg dose groups (FIG. 4). Increased expression of IFNα was only observed in subjects with an increased expression in IP-10, MCP-1 and/or IL-1RA. IFNα was increased in the 1.25 and 1.8 mg dose groups in 4/8 (range 63-533 pg/mL) and 2/6 (214 and 815 pg/ml) subjects, respectively. Cytokine levels and ISG expression peaked within 12-24 hours of a single dose of Compound 4 and returned to baseline levels within 48-96 hours post-administration (FIG. 5). Cytokine and ISG expression were less frequently observed in the 1.25 mg fed group compared with the fasted state.

Of note, IL-6 induction was observed in one subject in all but 1 of the dose groups (i.e., not in the 0.6 mg Compound 4 dose group), and hence not found to be dose-dependent. The aforementioned dose-dependent increase in fold change was confirmed by a dose-dependent increase in absolute expression levels of these cytokines (FIG. 5).

TABLE 9

Number of Subjects with a ≥2-fold Change from Baseline in Cytokine expression, or ISG Expression within 96 hours Post-dosing with Compound 4.

| | Pooled placebo | 0.2 mg Compound 4 (Fasted) | 0.6 mg Compound 4 (Fasted) | 1.25 mg Compound 4 (Fasted) | 1.8 mg Compound 4 (Fasted) |
|---|---|---|---|---|---|
| Full Analysis Set, N | 8 | 5 | 6 | 8 | 6 |
| GCSF | 2 (25.0%) | 0 | 1 (16.7%) | 1 (12.5%) | 0 |
| GMCSF | 0 | 0 | 0 | 0 | 0 |
| IFN-α | 0 | 0 | 0 | 4 (50.0%) | 2 (33.3%) |
| IFN-γ | 2 (25.0%) | 0 | 0 | 2 (25.0%) | 2 (33.3%) |
| IP-10 | 0 | 0 | 1 (16.7%) | 7 (87.5%) | 5 (83.3%) |
| IL-1β | 0 | 0 | 0 | 0 | 0 |
| IL-1RA | 0 | 0 | 0 | 6 (75.0%) | 5 (83.3%) |
| IL-10 | 0 | 0 | 0 | 0 | 0 |
| IL-12 subunit P40 | 0 | 0 | 0 | 0 | 0 |
| IL-6 | 0 | 1 (20.0%) | 0 | 1 (12.5%) | 1 (16.7%) |
| IL-8 | 0 | 0 | 0 | 0 | 0 |
| MIP-1β | 1 (12.5%) | 0 | 0 | 0 | 0 |
| MCP-1 | 0 | 0 | 1 (16.7%) | 6 (75.0%) | 3 (50.0%) |
| TNF-α | 0 | 0 | 0 | 0 | 0 |

Subjects who discontinued prior to the 96 hours visit were excluded from the analysis Subjects who discontinued prior to the 96 hours visit were excluded from the analysis In the 0.6 mg group, 1 out of the 6 treated subjects showed 2-fold increase of IP-10 and MCP-1. A maximum concentration of IP-10 (1,322.0 pg/mL) and MCP-1 (878.2 pg/mL) was observed 12 hours post dosing. In the 1.25 mg group, 3 out of the 8 treated subjects showed ≥2-fold increase of IFN-α, 7 out of the 8 treated subjects showed ≥2-fold increase of IP-10 and 6 out of 8 treated subjects showed 2-fold increase of MCP-1 and/or IL-1 RA. A maximum concentration of IFN-α (137.5 to 553.0 pg/mL), IP-10 (435.5 to 5,388.0 pg/mL), IL-1RA (203.9 to 641.9 pg/mL) and MCP-1 (1093.0 to 2,866.0 pg/mL) was observed 12 to 24 hours post dosing. In the 1.8 mg group, 2 out of the 6 treated subjects showed ≥2-fold increase of IFN-α, 5 out of the 6 treated subjects showed ≥2-fold increase of IP-10 and IL-1RA, and 4 out of 6 treated subjects showed ≥2-fold increase of MCP-1. A maximum concentration of IFN-α (214.0 to 815.0 pg/mL), IP-10 (438.4 to 7,186.0 pg/mL), IL-1 RA (80.7 to 5,004.0 pg/mL), and MCP-1 (1,065.0 to 13,055.0 pg/mL) was observed 12 to 24 hours post dosing. Increased expression of IFNα was observed only among subjects who also showed an increased expression in IP-10, MCP-1 and/or IL-1 RA in the 1.25 and 1.8 mg dose groups (FIG. 5). Cytokine levels returned to baseline levels within 48 to 96 hours post-administration.

In the fasted 1.25 mg group, 2 of the 3 treated females had a 2-fold increase in IFN-α compared to 2 out of 5 treated male subjects. In the 1.8 mg dose group, the single treated female had a ≥2-fold increase in IFN-α compared to 1 of the 5 treated male subjects.

Figure 6:
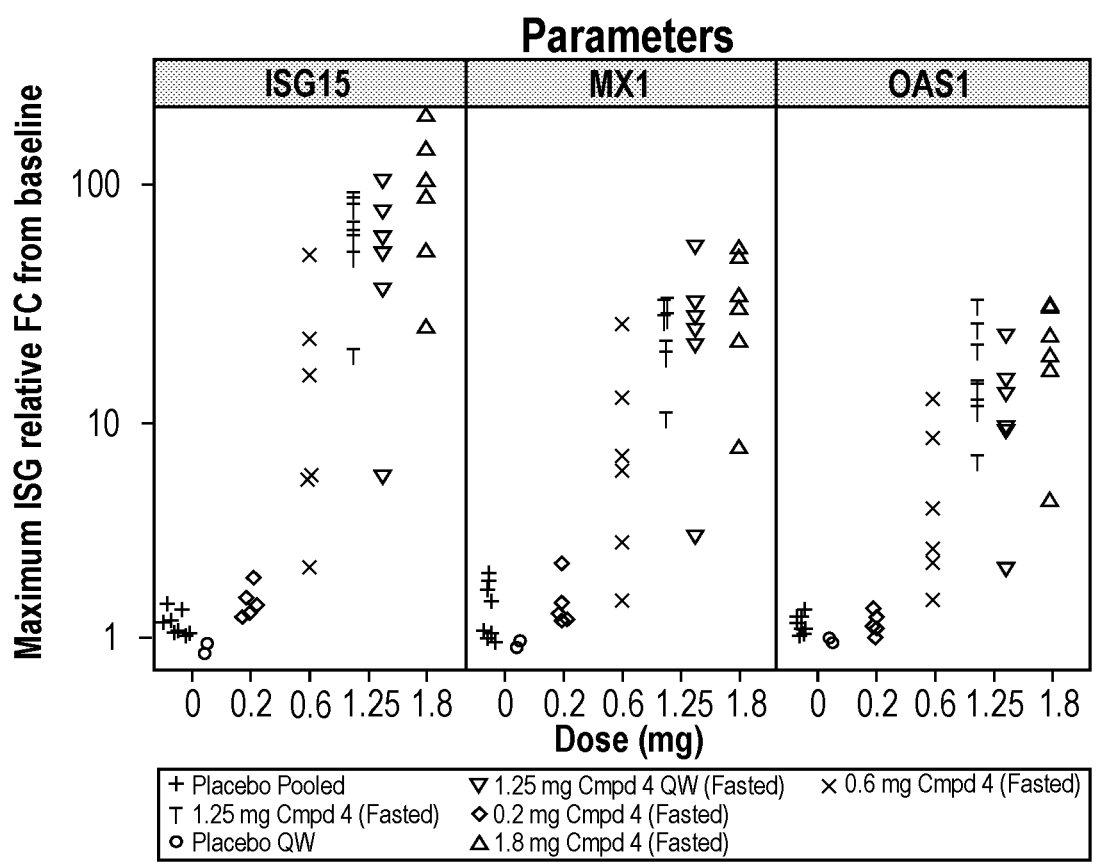
FIG. 6 depicts the maximum interferon-stimulated gene (ISG) relative fold changes from baseline on the first 96 hours post-administration in relation to dosage of Compound 4. FC: Fold change

Five of 6 treated subjects in the 0.6 mg dose group and all treated subjects of the 1.8 mg and 1.25 mg dose groups showed a ≥2-fold increase from baseline for all 3 ISGs (ISG15, MX-1, and OAS1) within the first 96 hours post dosing. No ISG induction was observed in the respective placebo groups (Table 10 and FIG. 6).

TABLE 10

Number of Participants With ≥2 Relative Fold Increase in ISG Expression Levels From Baseline in the First 96 Hours, Full Analysis Set - Part 1

|  | Pooled Placebo | 0.2 mg Compound 4 (Fasted) | 0.6 mg Compound 4 (Fasted) | 1.25 mg Compound 4 (Fasted) | 1.8 mg Compound 4 (Fasted) |
| --- | --- | --- | --- | --- | --- |
| Full Analysis Set, N | 8 | 5 | 6 | 8 | 6 |
| ISG15 | 0 | 0 | 5 (83.3%) | 8 (100%) | 6 (100%) |
| MX1 | 0 | 1 (20.0%) | 5 (83.3%) | 8 (100%) | 6 (100%) |
| OAS1 | 0 | 0 | 5 (83.3%) | 8 (100%) | 6 (100%) |

Subjects who discontinued prior to the 96 hours visit were excluded from the analysis Subjects who discontinued prior to the 96 hours visit have been excluded from the analysis ISG expression peaked within 12 to 24 hours of a single dose of Compound 4 and returned to baseline levels within 48 to 96 hours post-administration.

Increased expression of cytokines and ISGs was less frequently observed in the 1.25 mg fed state than in the fasted state. Of the 3 subjects that showed a 2-fold increased expression of IFN-α in the fasted state after single dosing, none showed an increase in IFN-α in the fed state.

13. PD Following Multiple Oral Dosing in Healthy Volunteers (Part 2)

Multiple Dose Administration (Part 2)

In the multiple dosing 1.25 mg group, an increase in the similar cytokines and ISGs was observed compared to the single dosing 1.25 mg group. No enhanced induction of PD responses as well as no evidence for tachyphylaxis (e.g., no reduced cytokine and ISG responses after the last dose compared to the first dose of Compound 4) were observed in the multiple dosing cohort.

Figure 7:
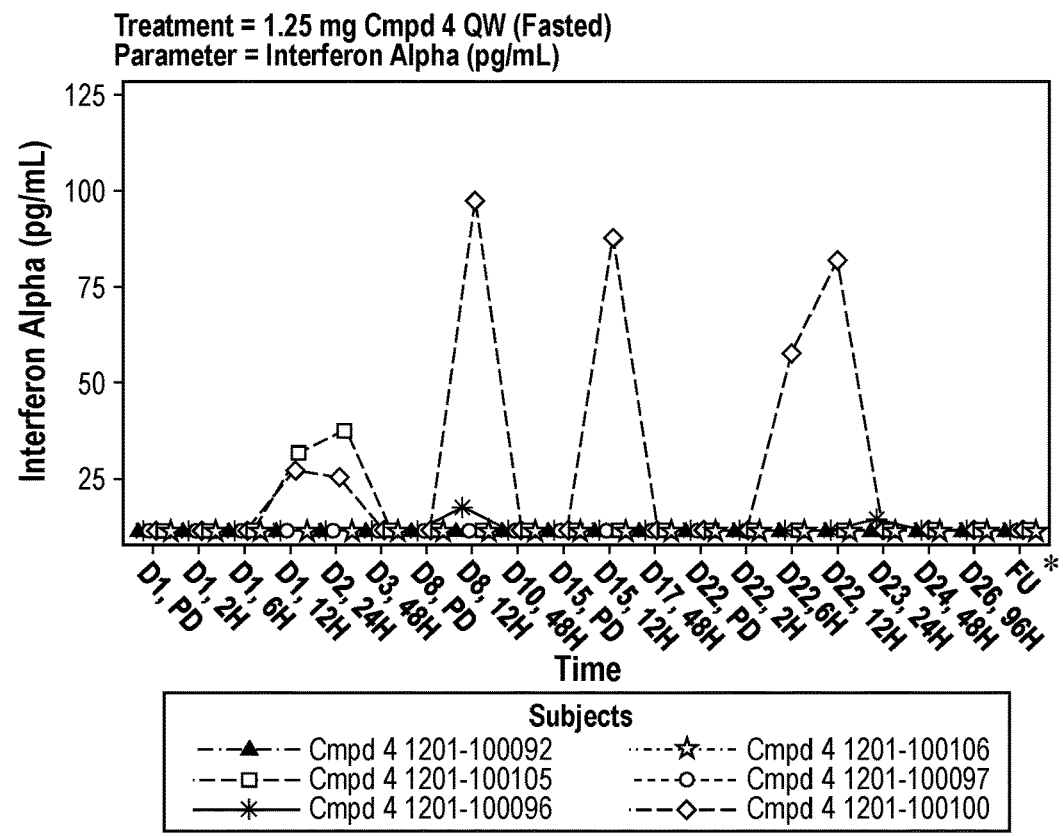
FIG. 7 depicts serum levels of INF-α and IP-10 induction following multiple oral dosing of Compound 4 in healthy volunteers. D: Day, H: Hour, PD: predose, FU: Follow-up; LLOQ IFN-α=12.5 pg/mL; LLOQ IP-10=25 pg/mL; *1-week FU visit (Day 29, ±2 days)
Figure 7:
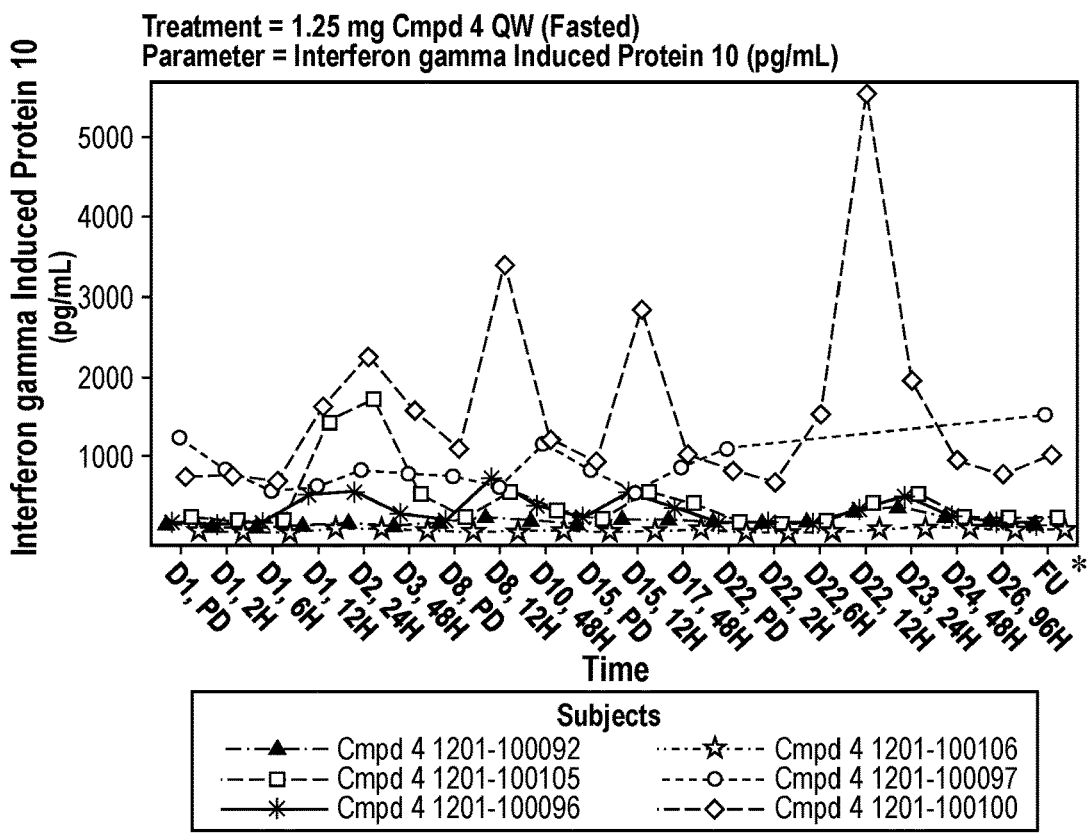

Absolute values for IFN-α and IP-10 are shown in FIG. 7, respectively. In subjects with an increase in IFN-α or IP-10 cytokine levels, values returned to baseline before administration of the subsequent dose suggesting that there is no sustained induction of PD responses despite observed accumulation of Compound 4.

14. Relationship Between PD and Safety Parameters: Expression of Systemic IFN-α TEAE Profile A positive sigmoidal relationship was observed between transient increases of systemic IFNα and the transient appearance of on-target flu-like symptoms and transient reduction in lymphocytes. Increased expression of IFNα, IP-10 and other cytokines were also observed in the absence of on-target flu-like symptoms. These data are shown in FIG. 8.

Figure 8:
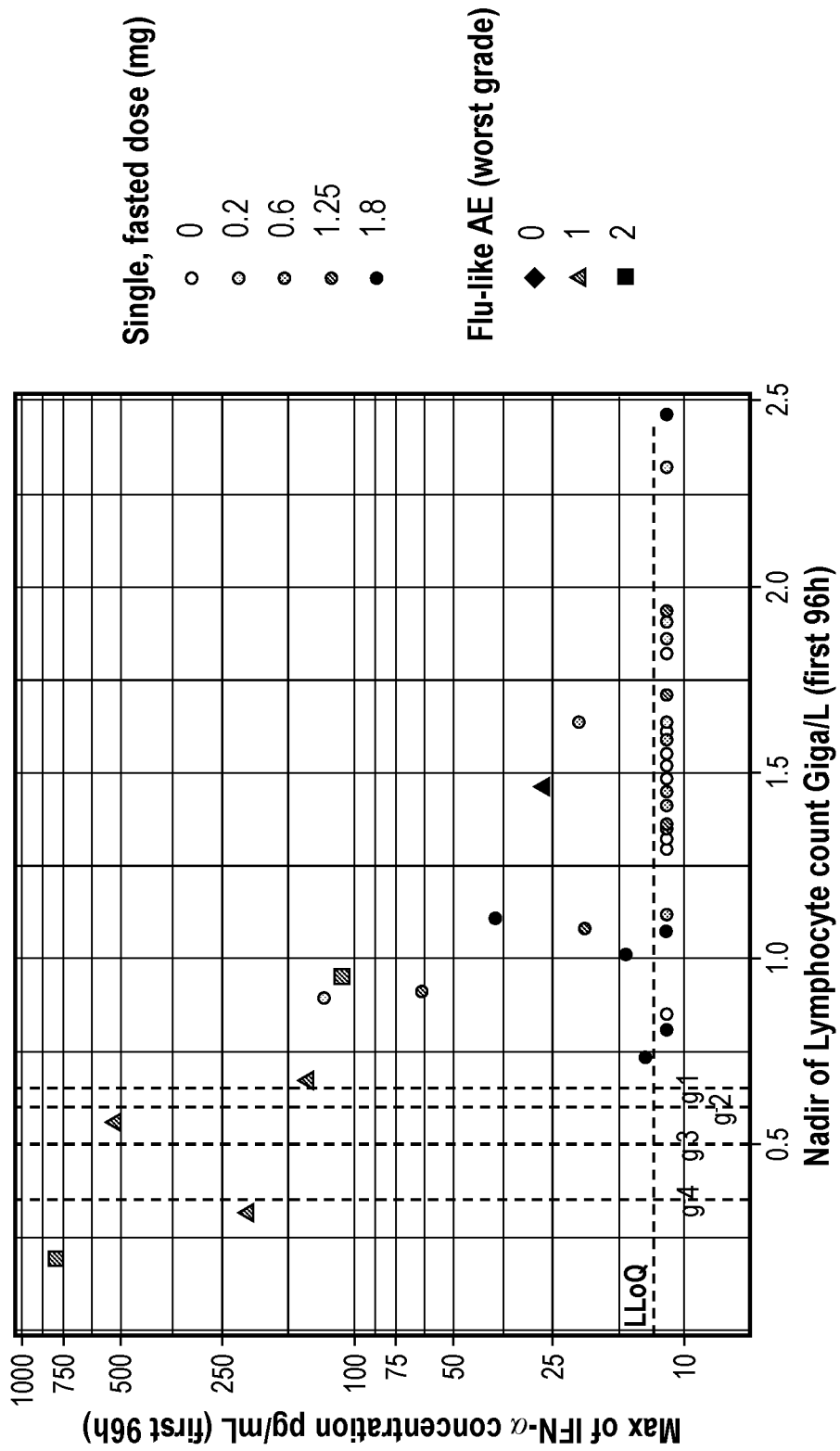
FIG. 8 depicts the Dose-dependent Absolute Expression Levels of systemic IFNα and the presence of on-target flu-like symptoms and lymphopenia. AE: adverse event, g: grade, LLOQ: lower limit of quantification.

IFN-α levels 100 pg/mL, observed in the 2 highest fasted dose groups (3 of 8 subjects for 1.25 mg and 2 of 6 subjects for 1.8 mg), coincided with a transient appearance of on-target, flu-like AEs (≤grade 2) and a low number of lymphocytes (FIG. 8). Increases in the levels of IFN-α, the appearance of flu-like symptoms (such as pyrexia, myalgia, and headache) and the nadir of lymphocyte count were observed approximately between 24 to 48 hours after dosing, with a return to baseline approximately 96 hours after dosing. Increased expression of IFNα, IP-10, and other cytokines was also observed in the absence of on-target flu-like symptoms in some subjects.

For the subject who experienced the cotton wool spots (PT: retinal exudates; observed during a scheduled ophthalmoscopy exam), IFN-α levels were <100 pg/mL at each timepoint, with a maximum of 97 pg/mL (8.4-fold increase) at 12 hours after the second administration. In addition, the subject did experience flu-like AEs (i.e., nausea and headache).

15. Safety and Tolerability

Nature and Frequency of Adverse Events
Single Dose

At least 1 AE was observed in 3 (37.5%) subjects in the pooled placebo group, (66.7%) subjects with 0.2 mg Compound 4, 3 (50.0%) subjects with 0.6 mg Compound 4, 5 (83.3%) subjects with 1.8 mg Compound 4, 8 (100%) subjects with 1.25 mg Compound 4 in fasted state and 6 (85.7%) subjects with 1.25 mg Compound 4 in fed state (Table 11).

TABLE 11

Summary of Adverse Events During the Study, Full Analysis Set - Part 1

|  | Screening | Pooled Placebo | 0.2 mg Compound 4 (Fasted) | 0.6 mg Compound 4 (Fasted) | 1.8 mg Compound 4 (Fasted) | 1.25 mg Compound 4 (Fasted) | 1.25 mg Compound 4 (Fed) |
| --- | --- | --- | --- | --- | --- | --- | --- |
| Full Analysis Set, N Number (%) of subjects with | 34 | 8 | 6 | 6 | 6 | 8 | 7 |
| At least one AE | 10 (29.4%) | 3 (37.5%) | 4 (66.7%) | 3 (50.0%) | 5 (83.3%) | 8 (100%) | 6 (85.7%) |
| At least one SAE | 0 | 0 | 0 | 0 | 0 | 0 | 0 |

TABLE 11-continued

Summary of Adverse Events During the Study, Full Analysis Set - Part 1

| | Screening | Pooled Placebo | 0.2 mg Compound 4 (Fasted) | 0.6 mg Compound 4 (Fasted) | 1.8 mg Compound 4 (Fasted) | 1.25 mg Compound 4 (Fasted) | 1.25 mg Compound 4 (Fed) |
|---|---|---|---|---|---|---|---|
| At least one fatal AE | 0 | 0 | 0 | 0 | 0 | 0 | 0 |
| At least one grade 1 AE | 10 (29.4%) | 3 (37.5%) | 4 (66.7%) | 3 (50.0%) | 3 (50.0%) | 7 (87.5%) | 6 (85.7%) |
| At least one grade 2 AE | 0 | 0 | 0 | 0 | 2 (33.3%) | 1 (12.5%) | 0 |
| At least one grade 3 or 4 AE | 0 | 0 | 0 | 0 | 0 | 0 | 0 |
| At least one AE for which any study drug or study was permanently stopped | 0 | 0 | 0 | 0 | 0 | 1 (12.5%) | 0 |
| At least one AE for which any study drug or study was temporarily stopped | 0 | 0 | 0 | 0 | 0 | 0 | 0 |
| At least one AE possibly related to any study drug | 0 | 0 | 0 | 1 (16.7%) | 1 (16.7%) | 5 (62.5%) | 1 (14.3%) |
| At least one AE probably related to any study drug | 0 | 0 | 0 | 0 | 2 (33.3%) | 3 (37.5%) | 0 |
| At least one AE very likely related to any study drug | 0 | 0 | 0 | 0 | 1 (16.7%) | 0 | 0 |
| At least one AE that is thought to be possibly, probably or very likely related to any study drug | 0 | 0 | 0 | 1 (16.7%) | 2 (33.3%) | 6 (75.0%) | 1 (14.3%) |

All AEs (no higher than grade 2) were observed in at most 2 subjects per dose group, apart from headache which was observed in 4 (50.0%) subjects, myalgia in 3 (37.5%) subjects and pyrexia in 3 (37.5%) subjects, all in the 1.25 mg Compound 4 dose group, and contact dermatitis in 3 (50.0%) subjects of the 1.8 mg Compound 4 dose group.

At least possibly treatment-related AEs included lymphadenopathy, palpitations, nausea, vomiting, chills, fatigue, pyrexia, back pain, myalgia, dizziness, headache, paraesthesia, cough, oropharyngeal pain and hypertension. Overall, pyrexia and headache were the most common treatment-related AEs each observed in 5 subjects, all occurring in the highest dose groups (1.8 mg and 1.25 mg, fasted) (Table 12). One (16.7%) subject receiving 1.8 mg Compound 4 had AEs (grade 1 pyrexia and chills) that were considered very likely related to the study drug.

TABLE 12

Treatment-related Adverse Events in at Least 2 Subjects per Treatment Arm, Full Analysis Set - Part 1

| | Screening | Pooled Placebo | 0.2 mg Compound 4 (Fasted) | 0.6 mg Compound 4 (Fasted) | 1.8 mg Compound 4 (Fasted) | 1.25 mg Compound 4 (Fasted) | 1.25 mg Compound 4 (Fed) |
|---|---|---|---|---|---|---|---|
| Full Analysis Set, N | 34 | 8 | 6 | 6 | 6 | 8 | 7 |
| Any AE, n (%) | 0 | 0 | 0 | 1 (16.7%) | 2 (33.3%) | 6 (75.0%) | 1 (14.3%) |
| General disorders and administration site conditions | 0 | 0 | 0 | 0 | 2 (33.3%) | 3 (37.5%) | 0 |
| Chills | 0 | 0 | 0 | 0 | 2 (33.3%) | 0 | 0 |
| Pyrexia | 0 | 0 | 0 | 0 | 2 (33.3%) | 3 (37.5%) | 0 |
| Musculoskeletal and connective tissue disorders | 0 | 0 | 0 | 0 | 1 (16.7%) | 4 (50.0%) | 0 |
| Myalgia | 0 | 0 | 0 | 0 | 1 (16.7%) | 3 (37.5%) | 0 |
| Nervous system disorders | 0 | 0 | 0 | 0 | 2 (33.3%) | 4 (50.0%) | 0 |
| Dizziness | 0 | 0 | 0 | 0 | 2 (33.3%) | 0 | 0 |
| Headache | 0 | 0 | 0 | 0 | 1 (16.7%) | 4 (50.0%) | 0 |
| Respiratory, thoracic and mediastinal disorders | 0 | 0 | 0 | 1 (16.7%) | 1 (16.7%) | 2 (25.0%) | 1 (14.3%) |

TABLE 12-continued

Treatment-related Adverse Events in at Least 2 Subjects per Treatment Arm, Full Analysis Set - Part 1

| | Screening | Pooled Placebo | 0.2 mg Compound 4 (Fasted) | 0.6 mg Compound 4 (Fasted) | 1.8 mg Compound 4 (Fasted) | 1.25 mg Compound 4 (Fasted) | 1.25 mg Compound 4 (Fed) |
|---|---|---|---|---|---|---|---|
| Oropharyngeal pain | 0 | 0 | 0 | 0 | 1 (16.7%) | 2 (25.0%) | 1 (14.3%) |
| Vascular disorder | 0 | 0 | 0 | 0 | 2 (33.3%) | 0 | 0 |
| Hypertension | 0 | 0 | 0 | 0 | 2 (33.3%) | 0 | 0 |

The denominator for the percentage calculations is the total number of subjects per treatment in the full analysis set.

No grade 3 or grade 4 AEs were observed in Part 1. Grade 2 treatment-related AEs were observed in 2 (33.3%) subjects of the 1.8 mg Compound 4 dose group (pyrexia, headache and hypertension) and in 1 (12.5%) subject of the fasted 1.25 mg Compound 4 dose group (pyrexia).

Multiple Dose

Eight (100%) subjects had at least 1 AE: 2 (100%) subjects in the placebo group and 6 (100%) subjects with 1.25 mg Compound 4 qw in fasted state (Table 13).

TABLE 13

Summary of Adverse Events During the Study, Full Analysis Set - Part 2

| | Screening | Pooled Placebo qw | 1.25 mg Compound 4 qw (Fasted) |
|---|---|---|---|
| Full Analysis Set, N | 8 | 2 | 6 |
| Number (%) of subjects with | | | |
| At least one AE | 3 (37.5%) | 2 (100%) | 6 (100%) |
| At least one SAE | 0 | 0 | 0 |
| At least one fatal AE | 0 | 0 | 0 |
| At least one grade 1 AE | 2 (25.0%) | 2 (100%) | 5 (83.3%) |
| At least one grade 2 AE | 1 (12.5%) | 0 | 1 (16.7%) |
| At least one grade 3 or 4 AE | 0 | 0 | 0 |
| At least one AE for which any study drug or study was permanently stopped | 0 | 0 | 1 (16.7%) |
| At least one AE for which any study drug or study was temporarily stopped | 0 | 0 | 0 |
| At least one AE possibly related to any study drug | 0 | 2 (100%) | 2 (33.3%) |
| At least one AE probably related to any study drug | 0 | 0 | 1 (16.7%) |
| At least one AE very likely related to any study drug | 0 | 0 | 1 (16.7%) |
| At least one AE that is thought to be possibly, probably or very likely related to any study drug | 0 | 2 (100%) | 3 (50.0%) |

All AEs were observed in at most 3 subjects per dose group. Most common AEs included headache (3 [50.0%] subjects) nasal congestion (3 [50.0%] subjects) and oropharyngeal pain (3 [50.0%] subjects), all observed in the active treatment group. Adverse events were observed in at most 1 subject in the placebo group.

Five (62.5%) subjects had an AE at least possibly treatment-related (2 [100%] subjects in the placebo group and 3 [50.0%] subjects receiving Compound 4), including abdominal pain and headache in the placebo group and single events of retinal exudates, nausea, retching, arthralgia, headache, dyspnea, and dry skin in the active treatment group. The retching observed in 1 (16.7%) of the 6 subjects on active treatment was considered very likely related to the study drug.

Worthy of note is the AE of bilateral retinal exudates (also referred to as cotton wool spots), observed (during a scheduled ophthalmoscopy exam) in 1 subject after receiving 4-weekly administrations of a single dose of 1.25 mg Compound 4, which was considered clinically significant by the Sponsor and investigator.

TABLE 14

Treatment-related Adverse Events, Full Analysis Set - Part 2

| | Screening | Pooled Placebo qw | 1.25 mg Compound 4 qw (Fasted) |
|---|---|---|---|
| Full Analysis Set, N | 8 | 2 | 6 |
| Any AE, n (%) | 0 | 2 (100%) | 3 (50.0%) |
| Eye disorders | 0 | 0 | 1 (16.7%) |
| Retinal exudates | 0 | 0 | 1 (16.7%) |
| Gastrointestinal disorders | 0 | 1 (50.0%) | 1 (16.7%) |
| Abdominal pain | 0 | 1 (50.0%) | 0 |
| Nausea | 0 | 0 | 1 (16.7%) |
| Retching | 0 | 0 | 1 (16.7%) |
| Musculoskeletal and connective tissue disorders | 0 | 0 | 1 (16.7%) |
| Arthralgia | 0 | 0 | 1 (16.7%) |
| Nervous system disorders | 0 | 1 (50.0%) | 1 (16.7%) |
| Headache | 0 | 1 (50.0%) | 1 (16.7%) |
| Respiratory, thoracic and mediastinal disorders | 0 | 0 | 1 (16.7%) |
| Dyspnoea | 0 | 0 | 1 (16.7%) |
| Skin and subcutaneous tissue disorders | 0 | 0 | 1 (16.7%) |
| Dry skin | 0 | 0 | 1 (16.7%) |

The denominator for the percentage calculations is the total number of subjects per treatment in the full analysis set.

Each treatment-related AEs occurred in at most 1 subject who received active treatment (Table 14).

No grade 3 or grade 4 AEs were observed in Part 2. None of the grade 2 AEs were considered treatment-related.

16. Deaths, Serious Adverse Events, and Other Significant Adverse Events

In the study, no deaths, other SAEs, or AEs of at least grade 3 occurred. In both Part 1 and Part 2, 1 subject discontinued due to an AE that was considered unrelated to the study drug.

Single Dose

One subject discontinued the study due to an AE of seasonal allergy. The subject was allocated to the 1.25 mg Compound 4 dose group.

The AE of seasonal allergy occurred 17 days after dosing with 1.25 mg Compound 4 in fasted state in Cohort 4 and was of grade 2 severity. The AE started on 9 Jun. 2018 and lasted more than 18 days. The relation to the study drug was considered doubtful by the investigator and cetirizine treatment was started to treat the seasonal allergy. However, study drug was withdrawn (ie, the subject chose not to roll-over to Cohort 6) and the subject discontinued on 26 Jun. 2018. The AE was considered not resolved by the end of the study.

Multiple Dose

One subject of the active treatment group (1.25 mg Compound 4 qw) discontinued the study due to an AE of ecchymosis.

The subject experienced ecchymosis on both forearms after having received the third dose of 1.25 mg of Compound 4 in fasted state (study drug administrations on 27 Aug., 3 Sep., and 10 Sep. 2018). The AE was grade 1 in severity and occurred on 16 Sep. 2018. The ecchymosis was considered resolved 13 days later on 29 Sep. 2018 and was not related to the study drug in the investigator's opinion. The study drug was withdrawn for this subject after the third administration of Compound 4 and the subject discontinued on 15 Oct. 2018.

17. Other Safety Observations

Single Dose

Treatment-related pyrexia was the most common flu-like AE in Part 1, observed in 3 subjects with grade 1 and 2 subjects with grade 2.

Multiple Dose

One subject had an AE of bilateral retinal exudates (cotton wool spots) that was considered of clinical significance by the Sponsor and investigator. The retinal exudates were observed in 1 (16.7%) subject of the active treatment group on 3 Oct. 2018 during a scheduled, routine ophthalmoscopy 2 weeks after the last of 4 administrations of 1.25 mg Compound 4. The subject was unblinded from the study after detection of the AE. There was no history of hypertension, vasculitis or diabetes reported for this subject. The retinal exudates were considered non-vision threatening by the ophthalmologist and other ocular abnormalities were not detected. The AE was classified as grade 1, was considered probably related to the study drug, and was resolved 6 weeks after first observation (during follow-up ophthalmologic exam).

18. Clinical Laboratory Tests

Single Dose

An overview of treatment-emergent graded abnormalities is presented in Table 15.

TABLE 15

Laboratory Safety Tabulation of Treatment-emergent Toxicities in >2 Subjects per Treatment Arm, Full Analysis Set - Part 1

|  | Pooled Placebo | 0.2 mg Compound 4 (Fasted) | 0.6 mg Compound 4 (Fasted) | 1.8 mg Compound 4 (Fasted) | 1.25 mg Compound 4 (Fasted) | 1.25 mg Compound 4 (Fed) |
|---|---|---|---|---|---|---|
| Full Analysis Set, N | 8 | 6 | 6 | 6 | 8 | 7 |
| Chemistry |  |  |  |  |  |  |
| Amylase (U/L), upwards, n | 8 | 6 | 6 | 6 | 8 | 7 |
| Grade 1 | 2 (25.0%) | 0 | 0 | 1 (16.7%) | 1 (12.5%) | 1 (14.3%) |
| Grade 2 | 1 (12.5%) | 1 (16.7%) | 0 | 0 | 0 | 0 |
| Cholesterol (mmol/L), upwards, n | 8 | 6 | 6 | 6 | 8 | 7 |
| Grade 1 | 0 | 0 | 2 (33.3%) | 1 (16.7%) | 1 (12.5%) | 0 |
| Grade 2 | 0 | 1 (16.7%) | 0 | 0 | 0 | 0 |
| Creatine kinase (U/L), upwards, n | 8 | 6 | 6 | 6 | 8 | 7 |
| Grade 1 | 0 | 3 (50.0%) | 0 | 0 | 0 | 0 |
| Grade 2 | 0 | 0 | 1 (16.7%) | 1 (16.7%) | 0 | 0 |
| Grade 4 | 1 (12.5%) | 0 | 0 | 0 | 0 | 0 |
| GFR from creatinine adjusted for BSA (mL/s/1.73m$^2$), downwards, n | 1 | — | — | 1 | 7 | — |
| Grade 2 | 0 | — | — | 0 | 3 (42.9%) | — |
| Glucose (mmol/L), upwards, n | 8 | 6 | 6 | 6 | 8 | 7 |
| Grade 1 | 3 (37.5%) | 1 (16.7%) | 1 (16.7%) | 0 | 3 (37.5%) | 2 (28.6%) |
| Grade 2 | 0 | 0 | 1 (16.7%) | 0 | 1 (12.5%) | 0 |
| LDL cholesterol (mmol/L, calculated), upwards, n | 8 | 6 | 6 | 6 | 8 | 7 |
| Grade 1 | 1 (12.5%) | 1 (16.7%) | 2 (33.3%) | 0 | 0 | 1 (14.3%) |
| Grade 2 | 0 | 1 (16.7%) | 1 (16.7%) | 0 | 0 | 0 |
| Grade 3 | 0 | 0 | 0 | 0 | 1 (12.5%) | 0 |
| Sodium (mmol/L), upwards, n | 8 | 6 | 6 | 6 | 8 | 7 |

TABLE 15-continued

Laboratory Safety Tabulation of Treatment-emergent Toxicities in >2 Subjects per Treatment Arm, Full Analysis Set - Part 1

|  | Pooled Placebo | 0.2 mg Compound 4 (Fasted) | 0.6 mg Compound 4 (Fasted) | 1.8 mg Compound 4 (Fasted) | 1.25 mg Compound 4 (Fasted) | 1.25 mg Compound 4 (Fed) |
|---|---|---|---|---|---|---|
| Grade 1 | 3 (37.5%) | 0 | 2 (33.3%) | 2 (33.3%) | 2 (25.0%) | 3 (42.9%) |
| Grade 2 | 1 (12.5%) | 0 | 1 (16.7%) | 1 (16.7%) | 1 (12.5%) | 0 |
| Triglycerides (mmol/L), upwards, n | 8 | 6 | 6 | 6 | 8 | 7 |
| Grade 1 | 4 (50.0%) | 1 (16.7%) | 4 (66.7%) | 5 (83.3%) | 3 (37.5%) | 3 (42.9%) |
| Grade 2 | 1 (12.5%) | 2 (33.3%) | 0 | 0 | 4 (50.0%) | 1 (14.3%) |
| Grade 3 | 0 | 0 | 0 | 1 (16.7%) | 0 | 0 |
| Urate (μmol/L), upwards, n | 8 | 6 | 6 | 6 | 8 | 7 |
| Grade 1 | 1 (12.5%) | 2 (33.3%) | 0 | 1 (16.7%) | 0 | 0 |
| Hematology |  |  |  |  |  |  |
| Lymphocytes (giga/L), downwards, n | 8 | 6 | 6 | 6 | 8 | 7 |
| Grade 2 | 0 | 0 | 0 | 0 | 1 (12.5%) | 0 |
| Grade 4 | 0 | 0 | 0 | 2 (33.3%) | 0 | 0 |
| Neutrophils, segmented (giga/L), downwards, n | 8 | 6 | 6 | 6 | 8 | 7 |
| Grade 1 | 0 | 0 | 0 | 0 | 2 (25.0%) | 0 |
| Grade 2 | 0 | 0 | 0 | 1 (16.7%) | 0 | 0 |
| Platelets (giga/L), downwards, n | 8 | 6 | 6 | 6 | 8 | 7 |
| Grade 1 | 0 | 0 | 0 | 2 (33.3%) | 1 (12.5%) | 0 |

Three grade 4 treatment-emergent laboratory abnormalities were observed: 1 (12.5%) subject in the placebo group had elevated creatine kinase levels and 2 (33.3%) subjects with 1.8 mg Compound 4 had low lymphocyte counts.

Overall, 3 subjects had a low lymphocyte count of at least grade 1: 1 (12.5%) subject had a treatment-emergent grade 2 low lymphocyte count after receiving 1.25 mg Compound 4 fasted and 2 (33.3%) subjects had a treatment-emergent grade 4 low lymphocyte count after receiving 1.8 mg Compound 4. The low lymphocyte count was observed proximal to dosing (within 24 hours) and was resolved within 72 hours in all cases. No cases of low lymphocyte count were reported in the 1.25 mg Compound 4 fed dose group.

Grade 3 abnormalities were observed in 1 (12.5%) subject of the placebo group with increase in AST levels, 1 (16.7%) subject of the 1.8 mg Compound 4 group experiencing an increase in triglycerides and in 1 (12.5%) subject of the 1.25 mg Compound 4 (fasted) group who had an increase in LDL cholesterol levels. The AST and LDL cholesterol grade 3 abnormalities were observed in the follow-up period (the subject with the LDL cholesterol abnormality also had a grade 3 abnormality at screening). The grade 3 increase in triglycerides was observed on Day 1 (8 and 12 hours post-dose), and improved to a grade 1 abnormality on Day 2.

Three (42.9%) subjects with 1.25 mg Compound 4 (fasted) had a grade 2 decrease in GFR. However, data from other dose groups were lacking so no conclusive conclusion could be made.

The most prevalent non-graded laboratory abnormalities were VLDL cholesterol increase, hematocrit decrease, segmented neutrophils/leukocytes increase, and erythrocytes decrease. All 4 abnormalities were observed in maximum 4 to 5 subjects per treatment arm with 5 (83.3%) subjects with low hematocrit levels in the 0.2 mg Compound 4 (fasted) group, 4 (50.0%) subjects in the placebo group and 4 (66.7%) subjects in the 1.8 mg Compound 4 (fasted) group with high VLDL cholesterol levels, 4 (66.7%) subjects with high values for segmented neutrophils/leukocytes in the 1.8 mg Compound 4 (fasted) group and 4 (50.0%) subjects with low erythrocytes levels in the placebo group. However, no clear or apparent dose effect or differences between the active treatments or placebo were visible.

None of the observed treatment-emergent laboratory abnormalities were reported as an AE.

Multiple Dose

An overview of treatment-emergent graded laboratory abnormalities is presented in Table 16.

TABLE 16

Laboratory Safety Tabulation of Treatment-emergent Toxicities, Full Analysis Set - Part 2

|  | Pooled Placebo qw | 1.25 mg Compound 4 qw (Fasted) |
|---|---|---|
| Full Analysis Set, N | 2 | 6 |
| Chemistry |  |  |
| Amylase (U/L), upwards, n | 2 | 6 |
| Grade 1 | 0 | 2 (33.3%) |
| Grade 2 | 1 (50.0%) | 0 |
| Pancreatic amylase (U/L), upwards, n | 1 | 2 |
| Grade 1 | 0 | 1 (50.0%) |
| Aspartate aminotransferase (U/L), upwards, n | 2 | 6 |
| Grade 1 | 0 | 1 (16.7%) |
| Grade 2 | 0 | 1 (16.7%) |
| Cholesterol (mmol/L), upwards, n | 2 | 6 |

TABLE 16-continued

Laboratory Safety Tabulation of Treatment-emergent Toxicities, Full Analysis Set - Part 2

| | Pooled Placebo qw | 1.25 mg Compound 4 qw (Fasted) |
|---|---|---|
| Grade 1 | 0 | 1 (16.7%) |
| Creatine kinase (U/L), upwards, n | 2 | 6 |
| Grade 3 | 0 | 1 (16.7%) |
| Grade 4 | 0 | 1 (16.7%) |
| GFR from creatinine adjusted for BSA (mL/s/1.73 m$^2$), downwards, n | 2 | 6 |
| Grade 2 | 0 | 1 (16.7%) |
| Glucose (mmol/L), upwards, n | 2 | 6 |
| Grade 1 | 2 (100.0%) | 4 (66.7%) |
| Grade 2 | 0 | 2 (33.3%) |
| Potassium (mmol/L), upwards, n | 2 | 6 |
| Grade 1 | 0 | 1 (16.7%) |
| LDL cholesterol (mmol/L, direct), upwards, n | — | 1 |
| Grade 1 | — | 1 (100.0%) |
| Sodium (mmol/L), upwards, n | 2 | 6 |
| Grade 1 | 1 (50.0%) | 0 |
| Triglycerides (mmol/L), upwards, n | 2 | 6 |
| Grade 1 | 1 (50.0%) | 1 (16.7%) |
| Grade 2 | 0 | 2 (33.3%) |

Grade 3 and 4 creatine kinase abnormalities (increases) were observed, each in 1 (16.7%) subject with 1.25 mg Compound 4 qw. These were isolated increases occurring during the follow-up period, after recent physical activity. Overall, 3 quarters of the subjects had a grade 1 increase in glucose levels but there was no distinction between the placebo group and active treatment.

All treatment-emergent non-graded abnormalities in laboratory safety were observed in 2 subjects per treatment arm at most, with the exception of 3 (50.0%) subjects in the active treatment group who had low erythrocyte count and 4 (66.7%) subjects in the active treatment group who had high values for the monocytes/leukocytes ratio. For other abnormalities, no clear or apparent differences were visible between the treatments.

None of the observed treatment-emergent laboratory abnormalities were reported as an AE.

19. Electrocardiogram and Vital Signs

Single Dose

A summary of the incidence of treatment-emergent abnormalities in ECG parameters is provided in Table 17.

TABLE 17

ECG Tabulation of Treatment-emergent Worst Case Abnormalities, Full Analysis Set - Part 1

| | Pooled Placebo | 0.2 mg Compound 4 (Fasted) | 0.6 mg Compound 4 (Fasted) | 1.8 mg Compound 4 (Fasted) | 1.25 mg Compound 4 (Fasted) | 1.25 mg Compound 4 (Fed) |
|---|---|---|---|---|---|---|
| Full Analysis Set, N | 8 | 6 | 6 | 6 | 8 | 7 |
| Actual values | | | | | | |
| Heart rate (bpm) | | | | | | |
| Low | 0 | 1 (16.7%) | 0 | 0 | 0 | 0 |
| QRS (ms) | | | | | | |
| High | 0 | 0 | 0 | 0 | 1 (12.5%) | 0 |
| QTcB (ms) | | | | | | |
| ]450; 480] | 0 | 0 | 0 | 0 | 1 (12.5%) | 0 |
| QTcF (ms) | | | | | | |
| ]450; 480] | 0 | 0 | 0 | 0 | 1 (12.5%) | 0 |
| Change from reference | | | | | | |
| QTcB (ms) | | | | | | |
| [30; 60] | 3 (37.5%) | 0 | 3 (50.0%) | 1 (16.7%) | 3 (37.5%)[a] | 2 (28.6%) |
| QTcF (ms) | | | | | | |
| [30; 60] | 1 (12.5%) | 0 | 0 | 0 | 1 (12.5%)[a] | 1 (14.3%) | bpm = beats per minute
[a] For 1 subject, the corresponding actual value was ]450; 480 ms].

Electrocardiogram abnormalities were infrequent, with no clear or apparent differences between the treatments.

Noteworthy changes in QTcB values compared to baseline (with increases between 30 and 60 ms) were reported in 3 (37.5%) subjects in the placebo group, 3 (50.0%) subjects with 0.6 mg Compound 4, 1 (16.7%) subject with 1.8 mg Compound 4 treatment arm, 3 (37.5%) subjects with 1.25 mg Compound 4 fasted and 2 (28.6%) subjects with 1.25 mg Compound 4 fed. Increases between 30 and 60 ms in QTcF values were observed in 1 (1.25%) subject in the placebo group, 1 (12.5%) subject with 1.25 mg Compound 4 fasted and 1 (14.3%) subject with 1.25 mg Compound 4 under fed condition.

None of the ECG abnormalities were reported as an AE.

A summary of incidence of treatment-emergent vital signs abnormalities (for each treatment) is provided in Table 18.

TABLE 18

Vital Signs Tabulation of Treatment-emergent Worst Case Abnormalities; Full Analysis Set - Part 1

| | Pooled Placebo | 0.2 mg Compound 4 (Fasted) | 0.6 mg Compound 4 (Fasted) | 1.8 mg Compound 4 (Fasted) | 1.25 mg Compound 4 (Fasted) | 1.25 mg Compound 4 (Fed) |
|---|---|---|---|---|---|---|
| Full Analysis Set, N | 8 | 6 | 6 | 6 | 8 | 7 |
| Supine pulse (bpm) | | | | | | |
| Low | 0 | 2 (33.3%) | 1 (16.7%) | 1 (16.7%) | 0 | 0 |
| Standing pulse (bpm) | | | | | | |
| Low | 1 (12.5%) | 0 | 0 | 0 | 0 | 0 |
| High | 1 (12.5%) | 3 (50.0%) | 0 | 0 | 1 (12.5%) | 1 (14.3%) |
| Supine SBP (mmHg) | | | | | | |
| Low | 0 | 1 (16.7%) | 0 | 0 | 1 (12.5%) | 0 |
| Grade 1 | 0 | 0 | 1 (16.7%) | 1 (16.7%) | 1 (12.5%) | 0 |
| Grade 2 | 0 | 0 | 0 | 1 (16.7%) | 0 | 0 |
| Standing SBP (mmHg) | | | | | | |
| Low | 0 | 0 | 0 | 0 | 1 (12.5%) | 0 |
| Grade 1 | 1 (12.5%) | 3 (50.0%) | 1 (16.7%) | 1 (16.7%) | 1 (12.5%) | 3 (42.9%) |
| Supine DBP (mmHg) | | | | | | |
| Low | 0 | 0 | 1 (16.7%) | 0 | 0 | 0 |
| Grade 1 | 0 | 0 | 0 | 1 (16.7%) | 1 (12.5%) | 1 (14.3%) |
| Standing DBP (mmHg) | | | | | | |
| Low | 1 (12.5%) | 0 | 0 | 0 | 0 | 0 |
| Grade 1 | 3 (37.5%) | 2 (33.3%) | 0 | 3 (50.0%) | 1 (12.5%) | 1 (14.3%) |
| Grade 2 | 1 (12.5%) | 0 | 0 | 1 (16.7%) | 2 (25.0%) | 2 (28.6%) |
| Grade 3 | 0 | 0 | 0 | 1 (16.7%) | 0 | 1 (14.3%) |
| Respiratory rate (brpm) | | | | | | |
| Grade 1 | 6 (75.0%) | 3 (50.0%) | 3 (50.0%) | 2 (33.3%) | 7 (87.5%) | 3 (42.9%) |
| Grade 2 | 0 | 0 | 0 | 1 (16.7%) | 0 | 0 |
| SaO$_2$ (%) | | | | | | |
| 95% to <98% | 2 (25.0%) | 4 (66.7%) | 4 (66.7%) | 2 (33.3%) | 3 (37.5%) | 3 (42.9%) |
| 90% to <95% | 2 (25.0%) | 1 (16.7%) | 0 | 0 | 3 (37.5%) | 1 (14.3%) | bpm = beats per minute;

brpm = breaths per minute

There were no clear or apparent differences between treatments in the incidence of treatment-emergent vital signs abnormalities. A grade 3 abnormality in standing DBP was seen in 2 subjects: in 1 (16.7%) subject with 1.8 mg Compound 4 and in 1 (14.3%) subject with 1.25 mg Compound 4 under fed condition. For the subject who received 1.8 mg Compound 4, the grade 3 abnormality was observed at follow-up Week 3. For the subject who received 1.25 mg Compound 4 under fed condition, the grade 3 abnormality was observed 1.5 hours after study drug administration. The abnormality had improved to a grade 2 abnormality at 4 hours after study drug administration. All subsequent standing DBP measurements performed for this subject within 24 hours post-dose were within normal range.

Two subjects who received 1.8 mg Compound 4 had a grade 1 increase in temperature around 12 hours after dosing. Values went above 38° C. and returned to baseline 24 hours after dosing. This was also reported as a treatment-related AE (pyrexia). Concomitant medication to lower the temperature (paracetamol, 1 g) was first administered within 12 hours after dosing, proximal to the first occurrence of pyrexia. Additional doses of either paracetamol (0.5 g) or ibuprofen (at most 400 mg) were given with at least 4 hours in between, until the pyrexia was resolved.

Multiple Dose

A summary of the incidence of treatment-emergent abnormalities in ECG parameters is provided in Table 19 Table.

TABLE 19

ECG Tabulation of Treatment-emergent Worst Case Abnormalities, Full Analysis Set - Part 2

|  | Pooled Placebo qw | 1.25 mg Compound 4 qw (Fasted) |
|---|---|---|
| Full Analysis Set, N | 2 | 6 |
| Actual values | | |
| Heart rate (bpm) | | |
| Low | 1 (50.0%) | 0 |
| QTcB (ms) | | |
| ]450; 480] | 0 | 1 (16.7%) |
| Change from reference | | |
| QTcB (ms) | | |
| [30; 60] | 0 | 1 (16.7%) |
| >60 | 0 | 1 (16.7%) |
| QTcF (ms) | | |
| [30; 60] | 0 | 1 (16.7%) | bpm = beats per minute

Electrocardiogram abnormalities were infrequent, with no clear or apparent differences between placebo and 1.25 mg Compound 4 qw.

None of the ECG abnormalities were reported as an AE.

A summary of incidence of treatment-emergent vital signs abnormalities (for each treatment) is provided in Table 20.

TABLE 20

Vital Signs Tabulation of Treatment-emergent Worst Case Abnormalities; Full Analysis Set - Part 2

|  | Pooled Placebo qw | 1.25 mg Compound 4 qw (Fasted) |
|---|---|---|
| Full Analysis Set, N | 2 | 6 |
| Supine pulse (bpm) | | |
| Low | 1 (50.0%) | 1 (16.7%) |
| Standing pulse (bpm) | | |
| High | 1 (50.0%) | 3 (50.0%) |
| Supine SBP (mmHg) | | |
| Low | 1 (50.0%) | 0 |
| Grade 1 | 1 (50.0%) | 1 (16.7%) |
| Standing SBP (mmHg) | | |
| Low | 2 (100.0%) | 2 (33.3%) |
| Grade 1 | 1 (50.0%) | 3 (50.0%) |
| Grade 2 | 1 (50.0%) | 0 |
| Supine DBP (mmHg) | | |
| Grade 1 | 0 | 2 (33.3%) |
| Standing DBP (mmHg) | | |
| Grade 1 | 1 (50.0%) | 2 (33.3%) |
| Grade 2 | 0 | 2 (33.3%) |
| Grade 3 | 1 (50.0%) | 2 (33.3%) |
| Respiratory rate (brpm) | | |
| Grade 1 | 1 (50.0%) | 4 (66.7%) |
| SaO$_2$ (%) | | |
| 95% to <98% | 1 (50.0%) | 5 (83.3%) | bpm = beats per minute;
brpm = breaths per minute

There were no clear or apparent differences between treatments in the incidence of treatment-emergent vital signs abnormalities. A grade 1 abnormality in respiratory rate was observed in 5 (62.5%) subjects overall, but there was no clear distinction between placebo or active treatment. A grade 3 abnormality in standing DBP was seen in 3 subjects: in 1 (50.0%) subject of the placebo group and in 2 (33.3%) subjects treated with 1.25 mg Compound 4 qw. For one of the subjects who were treated with 1.25 mg Compound 4 qw, the grade 3 abnormality was observed during an unscheduled measurement at the follow-up Week 1 visit. For the other subject who was treated with 1.25 mg Compound 4, grade 3 abnormalities in standing DBP were observed 4 hours after the first and after the second administration of study drug (Days 1 and 8, respectively) and on Day 12. This subject already had a grade 2 abnormality at screening and had at least a grade 1 abnormality at all but 3 of the scheduled measurements.

No abnormalities related to temperature were observed in Part 2.

20. Physical Examination

Single Dose

Twenty-four events of physical examination abnormalities were observed over a total of 13 subjects. Most of the events were skin-related. Two out of 24 events were considered clinically significant and were observed in the same subject who received 1.8 mg Compound 4. On Day 4 as well as on Day 5, the subject experienced erythema at the throat and cervical lymphadenopathy. Both were reported as a grade 1 AEs that were probably related to the study drug.

This was also one of the subjects who had a treatment-emergent grade 4 low lymphocyte count.

Multiple Dose

Fifteen events of physical examination abnormalities were observed over a total of 4 subjects. One event was considered clinically significant: the subject had an abnormality to the eyes at follow-up Week 2. Visual impairment and bilateral cotton wool spots on the retina (preferred term: retinal exudates; observed during a scheduled ophthalmoscopy exam) were reported as a grade 1 AE for this subject and were considered, respectively, doubtfully and probably related to the study drug by the investigator.

21. Conclusions

In healthy volunteers, the evaluated single oral doses of 0.2-1.8 mg Compound 4 were generally considered safe and well tolerated. Flu-like AEs Grade 2) and lymphopenia was observed for the two highest fasted dose levels assessed, 3/8 for 1.25 mg and 2/6 for 1.8 mg within 24-48 hours of dosing, with a rapid return to baseline. In fasted condition, Compound 4 exhibited dose-proportional pharmacokinetics over the dose range evaluated. Administration with food resulted in a significant decrease (~17%) in exposure to Compound 4 compared with fasted conditions. Oral Compound 4 administered under fasted conditions dose-dependently and transiently induced IFNα and/or IP-10, MCP-1 or IL-1 RA and ISGs in serum. Target engagement: Dose-dependent and transient systemic induction of absolute levels of IFNα (and IP-10) were associated with dose-dependent and transient appearance of flu-like symptoms and reduction in lymphocytes. These data support the continued development of Compound 4 as a potential treatment for chronic HBV.

LEC for Compound 4-induced cytokine release in vitro was determined to be 2 nM. For most cytokines and chemokines tested, Compound 4 is more potent on human whole blood cells compared to monkey whole blood cells.

Compound 4-stimulated human whole blood and PBMC supernatant showed potent antiviral activity in HBV-infected PHHs with a pronounced reduction in HBV DNA, HBeAg levels, and intracellular HBV RNA levels, and a less pronounced reduction in HBsAg, resulting in a maximum decline compared to DMSO controls of 1.5 log 10 for HBV DNA, 1.3 log 10 for HBeAg, 1.1 log 10 for HBV RNA, and 0.4 log 10 for HBsAg achieved at 3.3 nM. Based on these data, 3.3 nM might be identified as the anti-HBV activity target concentration in vitro.

The disclosed subject matter is not to be limited in scope by the specific embodiments and examples described herein. Indeed, various modifications of the disclosure in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

The invention claimed is:

1. A method of treating an HBV infection in a human subject in need thereof, comprising administering to the subject a pharmaceutical composition comprising at least one TLR-7 agonist and at least one pharmaceutically acceptable excipient;

wherein the TLR-7 agonist is a compound of Formula I:

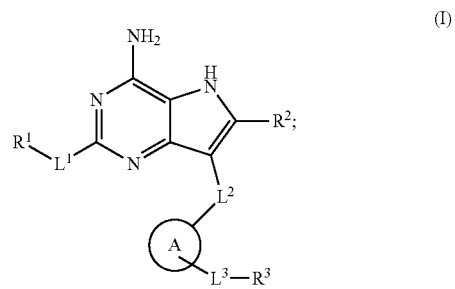

or a pharmaceutically acceptable salt thereof;

wherein:
  $L^1$ is —O—;
  $L^2$ is —CH$_2$—;
  $R^1$ is selected from the group consisting of —H and —C$_1$-C$_{10}$ alkyl; wherein the alkyl is optionally substituted by one or more $R^4$ groups;
  $R^2$ is selected from the group consisting of —H, —N, —COOH, and —CONH$_2$;
  ring A is selected from the group consisting of aryl and heteroaryl;
  $L^3$ is selected from the group consisting of C$_0$-C$_6$ alkylene and imino; wherein alkylene and imino are optionally substituted by one or more $R^4$ groups;
  $R^3$ is selected from the group consisting of —H, amino, C$_1$-C$_{10}$ alkyl, C$_3$-C$_{10}$ cycloalkyl, and 3-10 membered heterocycloalkyl; wherein amino, alkyl, cycloalkyl, and heterocycloalkyl are optionally substituted by one or more $R^4$ groups;
  or wherein $R^3$ and $L^3$, together with the atom to which $L^3$ is attached and the adjacent atom in ring A, form a saturated or unsaturated 5-8 membered ring, which is optionally substituted by one or more $R^4$ groups;
  $R^4$ is, independently at each occurrence, selected from the group consisting of —R, —OR, and =O; and
  R is, independently at each occurrence, selected from the group consisting of H and C$_1$-C$_8$ alkyl;
  wherein the compound of Formula I is administrated at a dose of 0.2 to 1.8 mg each time.

2. The method of claim 1, wherein the compound of Formula I is selected from the group consisting of:

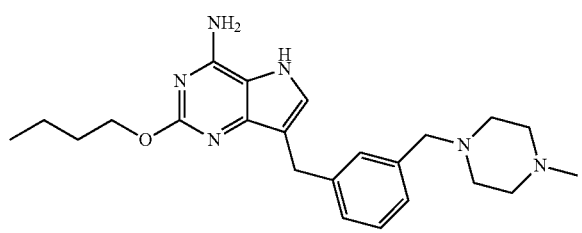

-continued
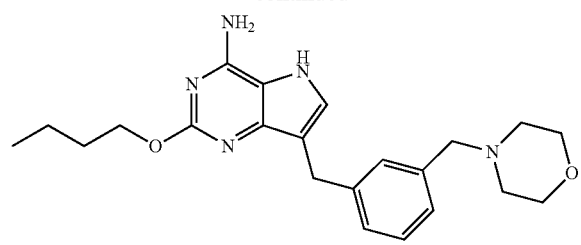
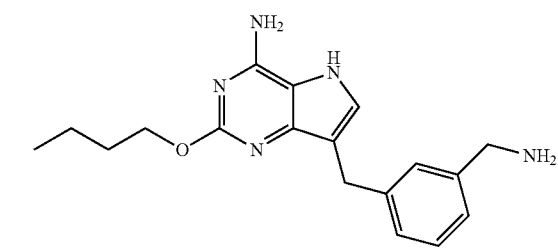
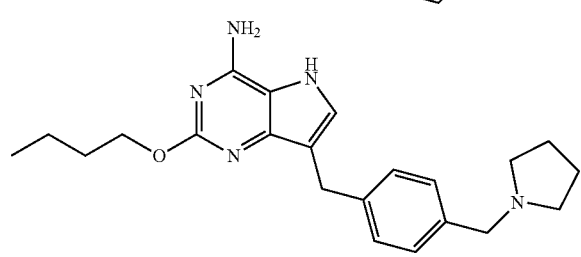
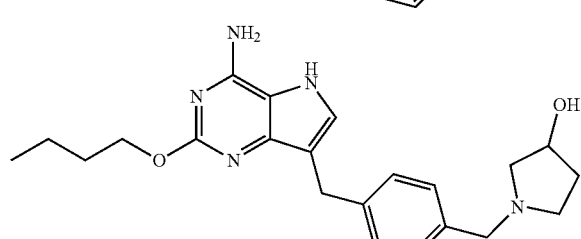
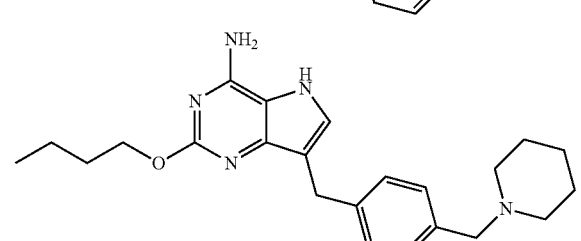
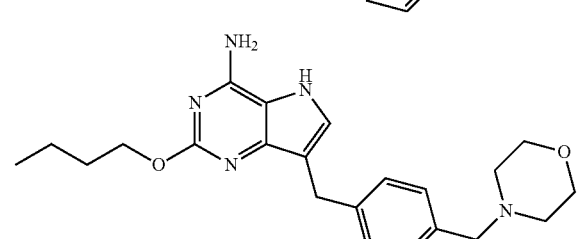
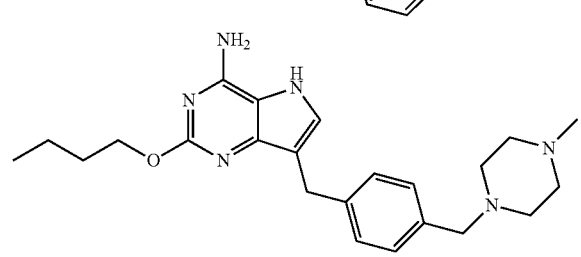
-continued
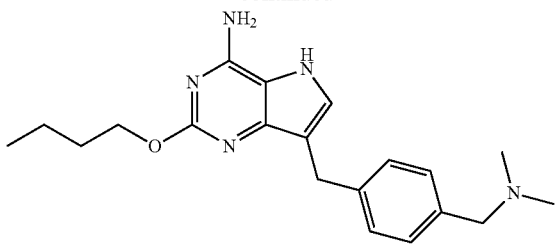
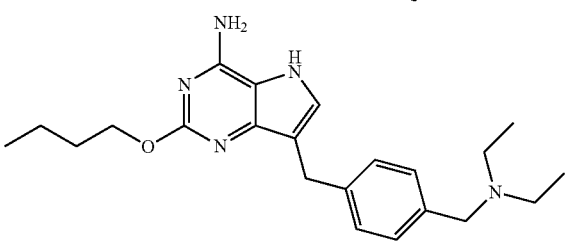
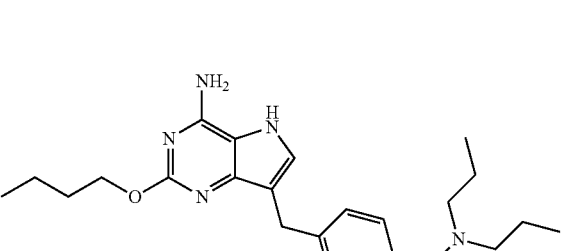
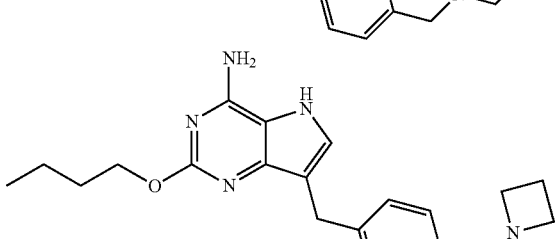
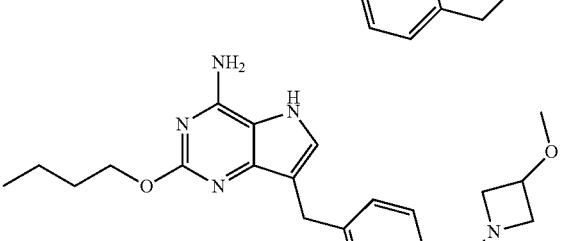
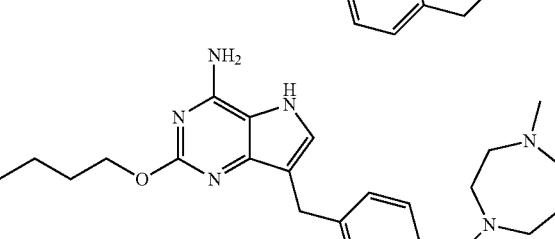
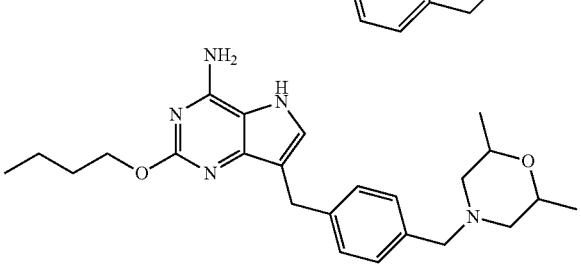

105
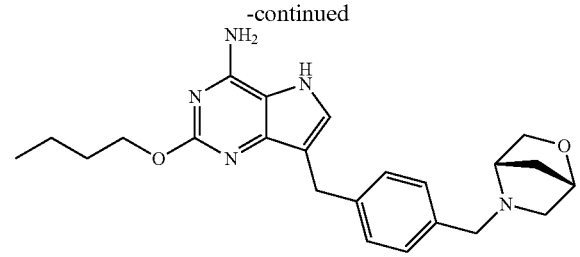
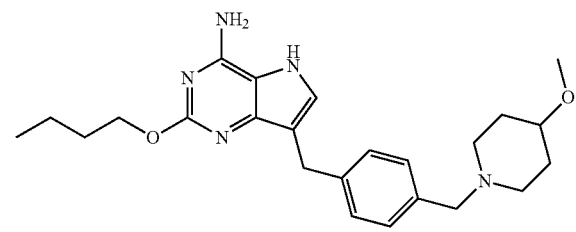
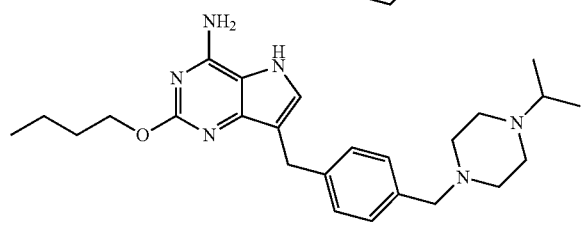
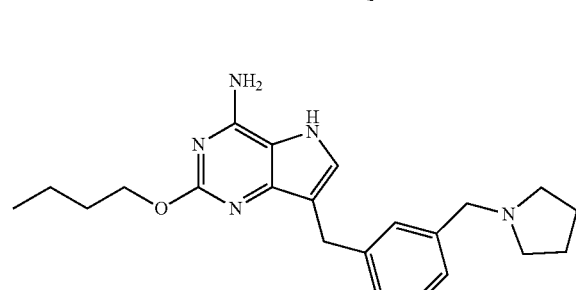
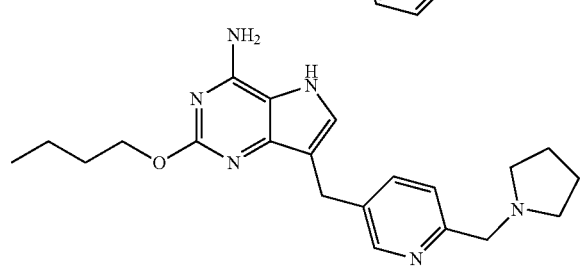
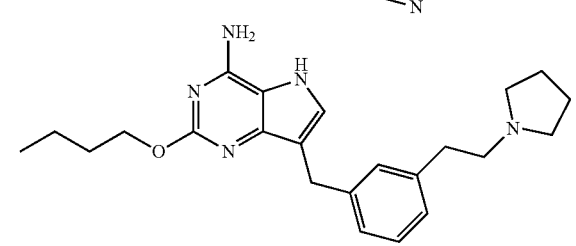
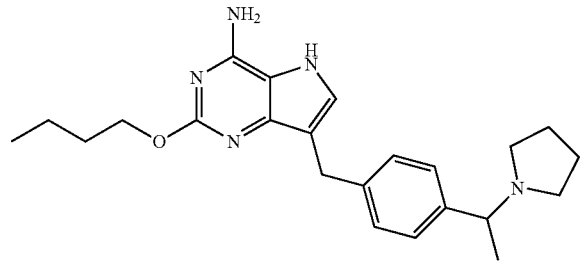
106
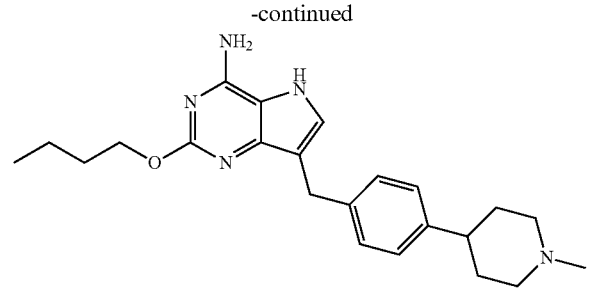
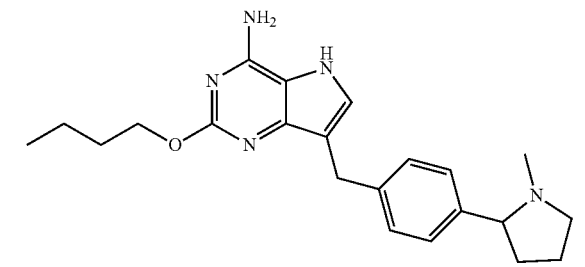
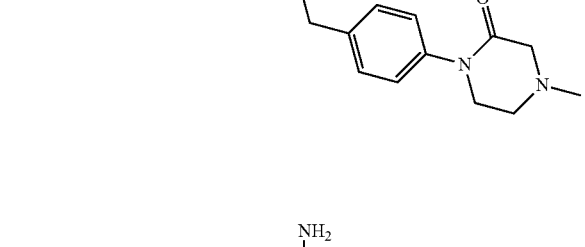
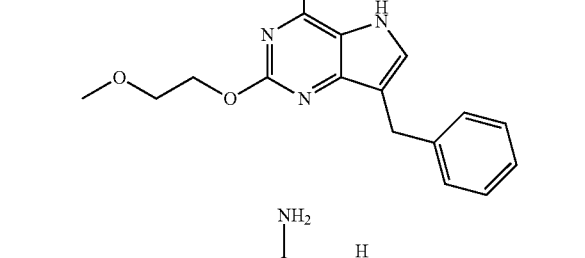
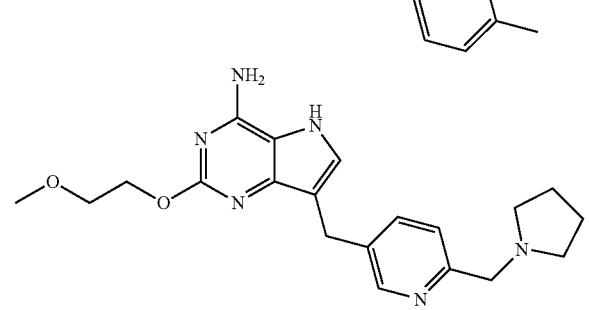

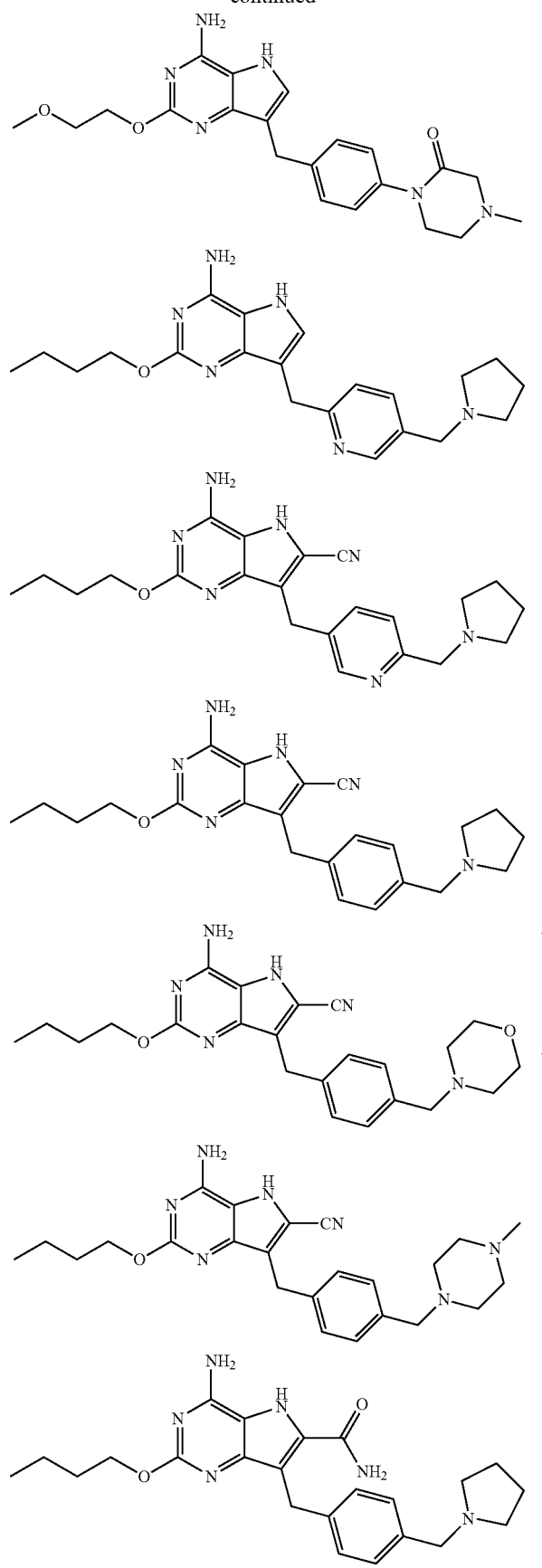
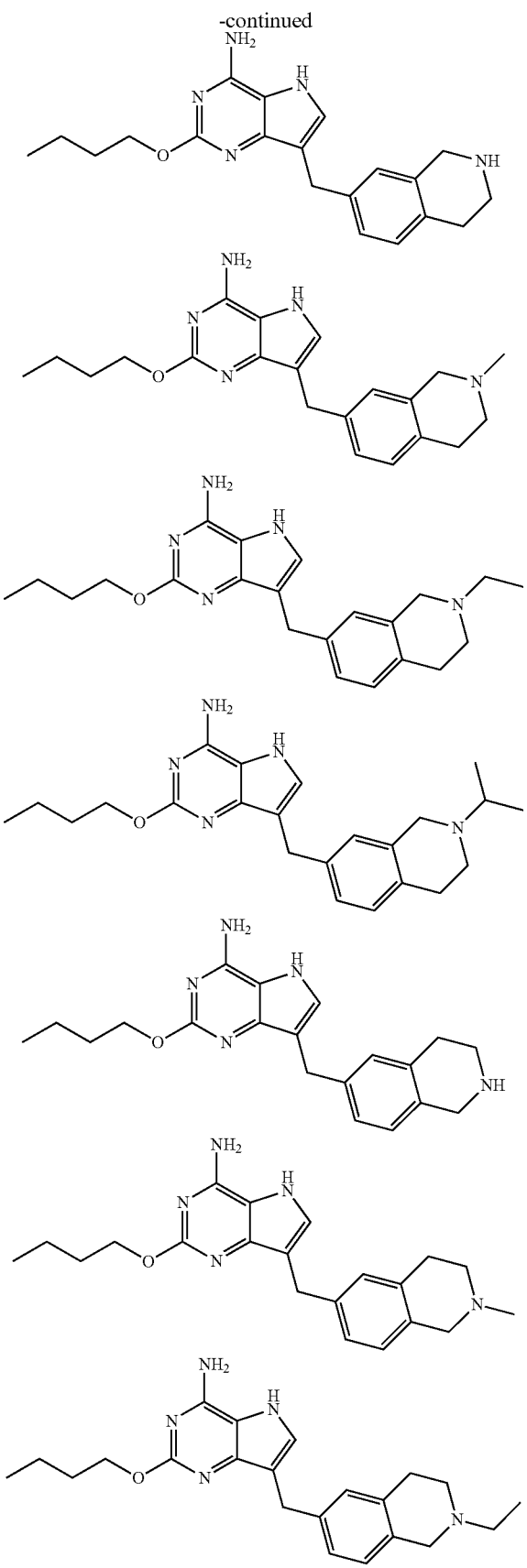
or a pharmaceutically acceptable salt thereof.

3. The method of claim 1, wherein the compound of Formula I is administered once daily (qd), once weekly (qw), or once every two weeks (q2w).

4. The method of claim 1, wherein the composition is formulated as an oral solution.

5. The method of claim 1, wherein the composition is formulated as an aqueous solution in citrate buffer.

6. The method of claim 5, wherein the concentration of the citrate buffer is 50 mM.

7. The method of claim 5, wherein the pH of the citrate buffer is 4-5.

8. The method of claim 1, wherein the composition comprises:
a compound of Formula I;
citric acid monohydrate;
sodium hydroxide solution; and
water.

9. The method of claim 1, wherein the composition comprises:
0.1 mg/mL of a compound of Formula I;
50 mM citric acid monohydrate;
sodium hydroxide solution; and
water.

10. The method of claim 1, wherein the composition comprises:
1.0 mg/mL of a compound of Formula I;
50 mM citric acid monohydrate;
sodium hydroxide solution; and
water.

11. The method of claim 1, wherein the composition is a tablet.

12. The method of claim 1, wherein the composition is a solid, oral tablet that comprises:
a compound of Formula I;
silicified microcrystalline cellulose;
croscarmellose sodium; and
magnesium stearate.

13. The method of claim 1, wherein the composition is a solid, oral tablet that comprises:
a compound of Formula I;
silicified microcrystalline cellulose;
croscarmellose sodium;
magnesium stearate;
polyvinyl alcohol;
polyethylene glycol;
titanium dioxide;
and talc.

14. The method of claim 1, wherein the compound of Formula I is administered at a dose of 0.2 mg, 0.5 mg, 0.6 mg, 1.0 mg, 1.25 mg, or 1.8 mg.

15. The method of claim 1, wherein the compound of Formula I is administered once daily (qd) in an amount selected from the group consisting of 0.2 mg, 0.5 mg, 0.6 mg, 1.0 mg, 1.25 mg, and 1.8 mg.

16. The method of claim 1, wherein the compound of Formula I is administered once weekly (qw) in an amount selected from the group consisting of 0.2 mg, 0.5 mg, 0.6 mg, 1.0 mg, 1.25 mg, and 1.8 mg.

17. The method of claim 1, wherein the compound of Formula I is administered once every two weeks (q2w) in an amount selected from the group consisting of 0.2 mg, 0.5 mg, 0.6 mg, 1.0 mg, 1.25 mg, and 1.8 mg.

18. The method of claim 1, wherein treating the HBV infection includes reducing the viral load associated with an HBV infection, reducing reoccurrence of an HBV infection, reducing an adverse physiological impact of an HBV infection, inducing remission of hepatic injury from an HBV infection, or prophylactically treating an HBV infection.

19. The method of claim 1, wherein the pharmaceutical composition is administered in combination with at least one additional therapeutic agent selected from the group consisting of a HBV polymerase inhibitor, interferon, viral entry inhibitor, viral maturation inhibitor, capsid assembly modulator, reverse transcriptase inhibitor, a TLR-agonist, and a combination thereof.

20. A method of improving safety of a dosing regimen in a human subject having an HBV infection, comprising administering to the subject a pharmaceutical composition comprising at least one TLR-7 agonist and at least one pharmaceutically acceptable excipient;
wherein the TLR-7 agonist is a compound of Formula I:

(I)

[Chemical structure of Formula I]

or a pharmaceutically acceptable salt thereof;
wherein:
$L^1$ is —O—;
$L^2$ is —CH$_2$—;
$R^1$ is selected from the group consisting of —H and —C$_1$-C$_{10}$ alkyl; wherein the alkyl is optionally substituted by one or more $R^4$ groups;
$R^2$ is selected from the group consisting of —H, —N, COOH, and —CONH$_2$;
ring A is selected from the group consisting of aryl and heteroaryl;
$L^3$ is selected from the group consisting of C$_0$-C$_6$ alkylene and imino; wherein alkylene and imino are optionally substituted by one or more $R^4$ groups;
$R^3$ is selected from the group consisting of —H, amino, C$_1$-C$_{10}$ alkyl, C$_3$-C$_{10}$ cycloalkyl, and 3-10 membered heterocycloalkyl; wherein amino, alkyl, cycloalkyl, and heterocycloalkyl are optionally substituted by one or more $R^4$ groups;
or wherein $R^3$ and $L^3$, together with the atom to which $L^3$ is attached and the adjacent atom in ring A, form a saturated or unsaturated 5-8 membered ring, which is optionally substituted by one or more $R^4$ groups;
$R^4$ is, independently at each occurrence, selected from the group consisting of —R, —OR, and =O; and
R is, independently at each occurrence, selected from the group consisting of H and C$_1$-C$_8$ alkyl;
wherein the compound of Formula I is administered at a dose of 0.2 to 1.8 mg each time.

* * * * *

UNITED STATES PATENT AND TRADEMARK OFFICE
CERTIFICATE OF CORRECTION

| | | |
|---|---|---|
| PATENT NO. | : 12,263,172 B2 | Page 1 of 1 |
| APPLICATION NO. | : 17/439280 | |
| DATED | : April 1, 2025 | |
| INVENTOR(S) | : Peter Jozef M Van Remoortere et al. | |

It is certified that error appears in the above-identified patent and that said Letters Patent is hereby corrected as shown below:

In the Claims

Column 102, Line 29 (Claim 1):
Delete:
"$R^2$ is selected from the group consisting of —H, —N, —COOH, and —$CONH_2$;"
And insert therefor:
--$R^2$ is selected from the group consisting of –H, –CN, –COOH, and –$CONH_2$;--

Column 110, Line 40 (Claim 20):
Delete:
"$R^2$ is selected from the group consisting of —H, —N, —COOH, and —$CONH_2$;"
And insert therefor:
--$R^2$ is selected from the group consisting of –H, –CN, –COOH, and –$CONH_2$;--

Signed and Sealed this
Tenth Day of June, 2025

Coke Morgan Stewart
*Acting Director of the United States Patent and Trademark Office*